United States Patent
Chen et al.

(10) Patent No.: US 12,116,367 B2
(45) Date of Patent: Oct. 15, 2024

(54) RING-MODIFIED PROLINE SHORT PEPTIDE COMPOUND AND USE THEREOF

(71) Applicant: FUJIAN AKEYLINK BIOTECHNOLOGY CO., LTD., Fujian (CN)

(72) Inventors: Shuhui Chen, Shanghai (CN); Yaxun Yang, Shanghai (CN); Jianchen Zhang, Shanghai (CN); Peng Li, Shanghai (CN); Haiying He, Shanghai (CN); Zheng Wang, Shanghai (CN); Jian Li, Shanghai (CN)

(73) Assignee: FUJIAN AKEYLINK BIOTECHNOLOGY CO., LTD., Fujian (CN)

( * ) Notice: Subject to any disclaimer, the term of this patent is extended or adjusted under 35 U.S.C. 154(b) by 0 days.

(21) Appl. No.: 18/306,236

(22) Filed: Apr. 25, 2023

(65) Prior Publication Data

US 2023/0312571 A1 Oct. 5, 2023

Related U.S. Application Data

(63) Continuation of application No. PCT/CN2022/087511, filed on Apr. 18, 2022.

(30) Foreign Application Priority Data

| Apr. 16, 2021 | (CN) | 202110413867.X |
| May 12, 2021 | (CN) | 202110517743.6 |
| Jun. 8, 2021 | (CN) | 202110637580.5 |
| Jun. 11, 2021 | (CN) | 202110659242.1 |
| Jul. 30, 2021 | (CN) | 202110879570.2 |
| Sep. 6, 2021 | (CN) | 202111040878.4 |
| Sep. 16, 2021 | (CN) | 202111088812.2 |
| Nov. 5, 2021 | (CN) | 202111307043.0 |
| Nov. 12, 2021 | (CN) | 202111343012.0 |
| Nov. 29, 2021 | (CN) | 202111433962.2 |
| Dec. 20, 2021 | (CN) | 202111567163.4 |
| Jan. 12, 2022 | (CN) | 202210029887.1 |
| Feb. 23, 2022 | (CN) | 202210170046.2 |

(51) Int. Cl.
C07D 403/12 (2006.01)
A61P 31/14 (2006.01)
C07D 471/08 (2006.01)
C07D 487/04 (2006.01)
C07D 491/048 (2006.01)
C07D 495/04 (2006.01)

(52) U.S. Cl.
CPC ............ C07D 471/08 (2013.01); A61P 31/14 (2018.01); C07D 403/12 (2013.01); C07D 487/04 (2013.01); C07D 491/048 (2013.01); C07D 495/04 (2013.01)

(58) Field of Classification Search
CPC .................................................. C07D 403/12
See application file for complete search history.

(56) References Cited

U.S. PATENT DOCUMENTS

| 7,012,066 B2 | 3/2006 | Saksena et al. |
| 2023/0140238 A1* | 5/2023 | Bardiot ............... C07D 405/14 514/340 |

FOREIGN PATENT DOCUMENTS

| CN | 102206247 A | 10/2011 |
| WO | 2005113580 A1 | 12/2005 |
| WO | 2011094426 A1 | 8/2011 |
| WO | 2018042343 A2 | 3/2018 |
| WO | 2021250648 A1 | 12/2021 |
| WO | 2021252644 A1 | 12/2021 |
| WO | 2022020242 A1 | 1/2022 |
| WO | 2022021841 A1 | 2/2022 |
| WO | 2023043816 A1 | 3/2023 |

OTHER PUBLICATIONS

Jul. 15, 2022 International Search Report issued in International Patent Application No. PCT/CN2022/087511.
Jul. 15, 2022 Written Opinion of the International Searching Authority issued in International Patent Application No. PCT/CN2022/087511.
Westberg,M.et al.,."Rational design of a new class of protease inhibitors for the potentia treatment of coronavirus diseases." BioRxiv, Sep. 15, 2020(Sep. 15, 2020)pp. 1-19.
Halford. B . . . "Pfizer unveils its oral SARS-COV-2 inhibitor." ACS Meeting News vol. 99,No. 13,Apr. 7, 2021 (Apr. 7, 2021)pp. 1-2, particularly p. 1, text.
Jul. 6, 2023 Canadian Office Action issued in Canadian Patent Application No. 3,201,360.
English Translation of Chinese Priority Application No. 202111433962. 2.
English Translation of Chinese Priority Application No. 202110413867. X.

(Continued)

*Primary Examiner* — Brian E McDowell
(74) *Attorney, Agent, or Firm* — Houston Beshining Law Office PLLC; Liangang Ye

(57) ABSTRACT

Disclosed are a ring-modified proline short peptide compound and the use thereof, and specifically disclosed is a compound represented by formula (X) or a pharmaceutically acceptable salt thereof.

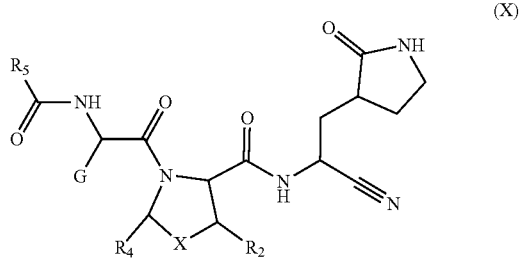

8 Claims, 7 Drawing Sheets

Specification includes a Sequence Listing.

(56) References Cited

OTHER PUBLICATIONS

English Translation of Chinese Priority Application No. 202110517743.6.
English Translation of Chinese Priority Application No. 202110637580.5.
English Translation of Chinese Priority Application No. 202110659242.1.
English Translation of Chinese Priority Application No. 202110879570.2.
English Translation of Chinese Priority Application No. 202111040878.4.
English Translation of Chinese Priority Application No. 202111088812.2.
English Translation of Chinese Priority Application No. 202111307043.0.
English Translation of Chinese Priority Application No. 202111343012.0.
English Translation of Chinese Priority Application No. 202111567163.4.
English Translation of Chinese Priority Application No. 202210029887.1.
English Translation of Chinese Priority Application No. 202210170046.2.
Sep. 1, 2023 European Supplementary Search Report issued in European Patent Application No. 22787664.6.
Sep. 11, 2023 Korean Office Action issued in Korean Patent Application No. 10-2023-7018146.
Oct. 13, 2023 Australian Office Action issued in Australian Patent Application No. 2022258377.
Nov. 1, 2023 Eurasian Office Action issued in Eurasian Patent Application No. 202390695.
Nov. 3, 2023 Singapore Office Action issued in Singapore Patent Application No. 11202302290Q.
John O. Link extrinsic 23 people. "Discovery of ledipasvir (GS-5885):a potent, the once-daily oral NS5A inhibitor for the treatment of hepatitis C virus infection", the Journal of Medicinal Chemistry, 2014, 57, 5, the pp. 2033-2046 (Dec. 9, 2013 And hereinafter, referred to as 'cited invention 2').
Nov. 23, 2023 Canadian Second Office Action issued in Canadian Patent Application No. 3,201,360.
Dec. 5, 2023 Japanese First Office Action issued in Japanese Patent Application No. 2023-518312.
Jan. 16, 2024 Chinese First Office Action issued in Chinese Patent Application No. 202310972706.3.
Jun. 4, 2024 Brazilian First Office Action issued in Brazilian Patent Application No. BR 1120230067618.
May 17, 2024 Korean Notice of Allowance issued in Korean Patent Application No. 10-2023-7018146.
Apr. 26, 2024 European Notice of Allowance issued in European Patent Application No. 22787664.6.

* cited by examiner

RING-MODIFIED PROLINE SHORT PEPTIDE COMPOUND AND USE THEREOF

CROSS-REFERENCE TO RELATED APPLICATIONS

The present application is a Continuation Application of International Application No. PCT/CN2022/087511, filed on Apr. 18, 2022, which claims priorities of the Chinese Patent Application No. CN202110413867X, filed on Apr. 16, 2021, the Chinese Patent Application No. CN2021105177436, filed on May 12, 2021, the Chinese Patent Application No. CN2021106375805, filed on Jun. 8, 2021, the Chinese Patent Application No. CN2021106592421, filed on Jun. 11, 2021, the Chinese Patent Application No. CN2021108795702, filed on Jul. 30, 2021, the Chinese Patent Application No. CN2021110408784, filed on Sep. 6, 2021, the Chinese Patent Application No. CN2021110888122, filed on Sep. 16, 2021, the Chinese Patent Application No. CN2021113070430, filed on Nov. 5, 2021, the Chinese Patent Application No. CN2021113430120, filed on Nov. 12, 2021, the Chinese Patent Application No. CN2021114339622, filed on Nov. 29, 2021, the Chinese Patent Application No. CN2021115671634, filed on Dec. 20, 2021, the Chinese Patent Application No. CN2022100298871, filed on Jan. 12, 2022 and the Chinese Patent Application No. CN2022101700462, filed on Feb. 23, 2022, the contents of which are incorporated herein by reference in their entireties.

REFERENCE TO SEQUENCE LISTING

The Sequence Listing is submitted concurrently with the specification as an XML formatted file via EFS-Web, with a file name of "P23410186US-2-SEQ", a creation date of Apr. 20, 2023, and a size of 2,670 bytes. The Sequence Listing filed via EFS-Web is part of the specification and is incorporated in its entirety by reference herein.

TECHNICAL FIELD

The present disclosure relates to the technical field of medical chemistry, in particular to a ring-modified proline short peptide compound and a use thereof.

BACKGROUND

At present, there are seven kinds of coronaviruses that can infect humans, namely HCoV-229E, HCoV-OC43, HCoV-NL63, HCoV-HKU1, SARS-CoV (SARS), MERS-CoV (MERS) and COVID-19 which is first discovered in December 2019, and COVID-19 is changing from Alpha, Beta to Delta . . . and then to Omicron, and is still spreading rapidly and changing constantly. In 2022, human ushered in the third year of COVID-19 pandemic, with the cumulative number of confirmed cases exceeding 500 million and the cumulative number of deaths exceeding 6 million, and with the number of confirmed cases of COVID-19 exceeding 1 million in about 50 countries. The transmission mode of epidemiology, spreading trend and pandemic level far exceed those of H1N1 influenza A in 2009. SARS-CoV-2 is a single positive-strand RNA virus and has high homology with SARS-CoV and MERS-CoV. After the virus infects and enters the host cell, with the help of the host cell, the genetic material RNA first translates and expresses two polyprotein precursors (pp1a and pp1ab), and the polyprotein precursors undergo intramolecular cleavage under the action of 3CL protease and PL protease to produce multiple unstructured proteins. Because 3CL protease is responsible for the cleavage of at least 11 sites, the 3CL protease is also called main protease (Mpro). Unstructured proteins are involved in the production of virus subgene RNA and four structural proteins (E protein, M protein, S protein and N protein), thus completing the reproduction and release of virus offspring; 3CL protease belongs to cysteine protease, and the active form of 3CL protease is homodimer. 3CL protease is relatively conservative in coronavirus, and the substrates of 3CL protease from different coronaviruses have common characteristics. Because there is no protease homologous to 3CL protease in human body, 3CL protease has become one of the ideal targets against coronavirus.

BRIEF SUMMARY OF THE INVENTION

The present disclosure provides a compound represented by formula (X) or a pharmaceutically acceptable salt thereof,

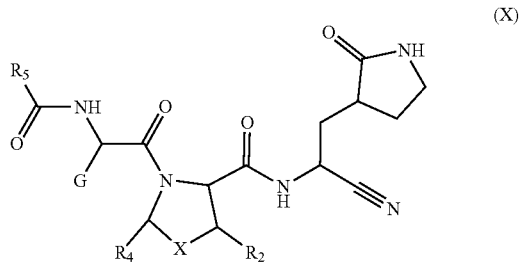

(X)

wherein,
G is selected from

and

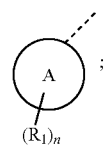

ring A is selected from $C_{3-10}$ cycloalkyl, 3- to 10-membered heterocycloalkyl, $C_{6-10}$ aryl and 5- to 10-membered heteroaryl;

$R_1$ is each independently selected from halogen, $OR_{11}$, CN, $CH_3S(O)_m$—, —$NH(R_{12})$, $C_{1-3}$ alkyl and $C_{1-3}$ haloalkyl;

$R_{11}$ is selected from H, $C_{1-3}$ alkyl, $C_{1-3}$ haloalkyl, $CH_3(OCH_2CH_2)_p$— and $H(OCH_2CH_2)_q$—;

$R_{12}$ is selected from $C_{1-3}$ alkyl, $C_{1-3}$ haloalkyl, $CH_3CO$— and $CH_3SO_2$—;

m is selected from 0, 1 and 2;

p and q are selected from 1, 2, 3, 4, 5 and 6;

n is selected from 0, 1, 2, 3 and 4;

X is selected from —$CH(R_3)$—, —$CH_2CH_2$—, O, S, Se, $SO_2$ and —$N(R_3)$—, and the —$CH_2CH_2$— is optionally substituted by 1, 2, 3 or 4 R;

R is each independently selected from halogen, OH, NH$_2$, CN, C$_{1-3}$ alkyl and C$_{1-3}$ haloalkyl;

R$_3$ is each independently selected from H, C$_{1-3}$ alkyl, C$_{1-3}$ alkoxy, C$_{1-3}$ haloalkyl, C$_{1-3}$ haloalkoxy, C$_{6-10}$ aryl and 5- to 10-membered heteroaryl, and the C$_{6-10}$ aryl and 5- to 10-membered heteroaryl are optionally substituted by 1, 2 or 3 R$_{31}$;

R$_2$ and R$_4$ are each independently selected from H, C$_{1-3}$ alkyl, C$_{1-3}$ alkoxy, C$_{1-3}$ haloalkyl, C$_{1-3}$ haloalkoxy, C$_{6-10}$ aryl and 5- to 10-membered heteroaryl, and the C$_{6-10}$ aryl and 5- to 10-membered heteroaryl are optionally substituted by 1, 2 or 3 R$_{21}$;

or,

R$_2$ and R$_4$ together with the atoms to which they are attached form C$_{5-8}$ cycloalkyl, 5- to 6-membered heterocycloalkyl and 5- to 6-membered heterocycloalkenyl, and the C$_{5-8}$ cycloalkyl, 5- to 6-membered heterocycloalkyl and 5- to 6-membered heterocycloalkenyl are optionally and independently substituted by 1 or 2 R$_a$;

R$_a$ is each independently selected from H, halogen, C$_{1-3}$ alkyl, C$_{1-3}$ alkoxy, C$_{1-3}$ haloalkoxy, C$_{3-6}$ cycloalkyl, C$_{6-10}$ aryl and 5- to 10-membered heteroaryl, and the C$_{3-6}$ cycloalkyl, C$_{6-10}$ aryl and 5- to 10-membered heteroaryl are optionally substituted by 1, 2 or 3 R$_{41}$;

R$_{21}$, R$_{31}$ and R$_{41}$ are each independently selected from halogen, OH, NH$_2$, CN, C$_{1-3}$ alkyl, C$_{1-3}$ alkoxy, C$_{1-3}$ haloalkyl and C$_{1-3}$ haloalkoxy;

R$_5$ is selected from C$_{1-3}$ alkyl, C$_{1-3}$ haloalkyl, C$_{1-3}$ alkoxy, C$_{1-3}$ haloalkoxy, —CH$_2$—R$_6$ and —CH$_2$—O—R$_6$;

R$_6$ is selected from phenyl, and the phenyl is optionally substituted by 1, 2 or 3 R$_{61}$;

R$_{61}$ is selected from halogen, C$_{1-3}$ alkyl, C$_{1-3}$ haloalkyl, C$_{1-3}$ alkoxy and C$_{1-3}$ haloalkoxy.

The present disclosure also provides a compound represented by formulas (X-1) and (X-2) or a pharmaceutically acceptable salt thereof,

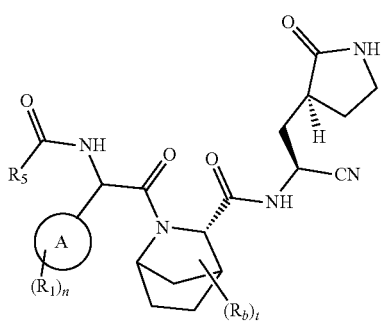

(X-1)

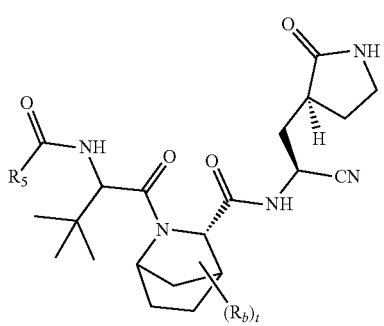

(X-2)

wherein,

R$_b$ is each independently selected from H, halogen, C$_{1-3}$ alkyl, C$_{1-3}$ alkoxy, C$_{1-3}$ haloalkoxy and C$_{3-6}$ cycloalkyl;

or, two R$_b$ on adjacent carbon atoms or the same carbon atom together with the atoms to which they are attached form cyclopropyl or cyclobutyl;

t is selected from 1 and 2;

R$_1$, R$_5$, n and ring A are as defined herein.

The present disclosure also provides a compound represented by formula (IV) or a pharmaceutically acceptable salt thereof,

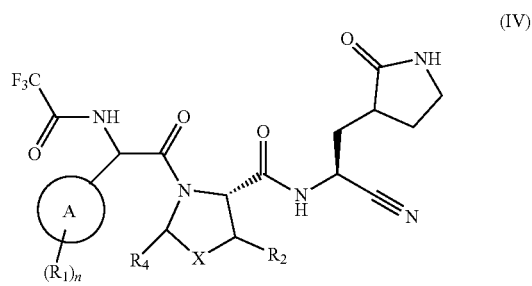

(IV)

wherein, ring A is selected from C$_{3-10}$ cycloalkyl, 3- to 10-membered heterocycloalkyl, C$_{6-10}$ aryl and 5- to 10-membered heteroaryl;

R$_1$ is each independently selected from halogen, OR$_{11}$, CN, CH$_3$S(O)$_m$—, —NH(R$_{12}$), C$_{1-3}$ alkyl and C$_{1-3}$ haloalkyl;

R$_{11}$ is selected from H, C$_{1-3}$ alkyl, C$_{1-3}$ haloalkyl, CH$_3$(OCH$_2$CH$_2$)$_p$— and H(OCH$_2$CH$_2$)$_q$—;

R$_{12}$ is selected from C$_{1-3}$ alkyl, C$_{1-3}$ haloalkyl, CH$_3$CO— and CH$_3$SO$_2$—;

m is selected from 0, 1 and 2;

p and q are selected from 1, 2, 3, 4, 5 and 6;

n is selected from 0, 1, 2, 3 and 4;

X is selected from —CH(R$_3$)—, —CH$_2$CH$_2$—, O, S, Se, SO$_2$ and —N(R$_3$)—, and the —CH$_2$CH$_2$— is optionally substituted by 1, 2, 3 or 4 R;

R is each independently selected from halogen, OH, NH$_2$, CN, C$_{1-3}$ alkyl and C$_{1-3}$ haloalkyl;

R$_3$ is each independently selected from H, C$_{1-3}$ alkyl, C$_{1-3}$ alkoxy, C$_{1-3}$ haloalkyl, C$_{1-3}$ haloalkoxy, C$_{6-10}$ aryl and 5- to 10-membered heteroaryl, and the C$_{6-10}$ aryl and 5- to 10-membered heteroaryl are optionally substituted by 1, 2 or 3 R$_{31}$;

R$_2$ and R$_4$ are each independently selected from H, C$_{1-3}$ alkyl, C$_{1-3}$ alkoxy, C$_{1-3}$ haloalkyl, C$_{1-3}$ haloalkoxy, C$_{6-10}$ aryl and 5- to 10-membered heteroaryl, and the C$_{6-10}$ aryl and 5- to 10-membered heteroaryl are optionally substituted by 1, 2 or 3 R$_{21}$;

or,

R$_2$ and R$_4$ together with the atoms to which they are attached form C$_{5-8}$ cycloalkyl, 5- to 6-membered heterocycloalkyl and 5- to 6-membered heterocycloalkenyl, and the C$_{5-8}$ cycloalkyl, 5- to 6-membered heterocycloalkyl and 5- to 6-membered heterocycloalkenyl are optionally substituted by 1 or 2 R$_a$;

R$_a$ is each independently selected from H, halogen, C$_{1-3}$ alkyl, C$_{1-3}$ alkoxy, C$_{1-3}$ haloalkoxy, C$_{6-10}$ aryl and 5- to 10-membered heteroaryl, and the C$_{6-10}$ aryl and 5- to 10-membered heteroaryl are optionally substituted by 1, 2 or 3 R$_{41}$;

$R_{21}$, $R_{31}$ and $R_{41}$ are each independently selected from halogen, OH, $NH_2$, CN, $C_{1-3}$ alkyl, $C_{1-3}$ alkoxy, $C_{1-3}$ haloalkyl and $C_{1-3}$ haloalkoxy;

the "heterocycloalkyl", "heterocycloalkenyl" and "heteroaryl" contain 1, 2 or 3 heteroatoms or heteroatom groups independently selected from O, S, $SO_2$, N, P and Se.

In some embodiments of the present disclosure, the $R_1$ is selected from F, Cl, Br, I, methyl, OH, CN, $CH_3O-$, $CH_3S-$, $CH_3S(O)-$, $CH_3SO_2-$, $CH_3NH-$, $CH_3CONH-$, $CH_3SO_2NH-$, $CH_3OCH_2CH_2O-$, $CH_3(OCH_2CH_2)_2O-$, $CH_3(OCH_2CH_2)_4O-$, $HOCH_2CH_2O-$, $H(OCH_2CH_2)_2O-$ and $H(OCH_2CH_2)_4O-$, and the other variables are as defined herein.

In some embodiments of the present disclosure, the ring A is selected from $C_{5-9}$ cycloalkyl, 5- to 8-membered heterocycloalkyl, adamantyl and phenyl, and the other variables are as defined herein.

In some embodiments of the present disclosure, the ring A is selected from

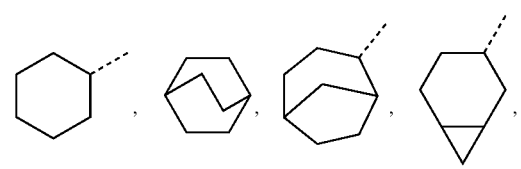
,
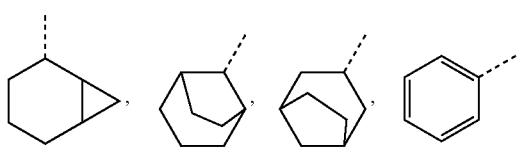
,
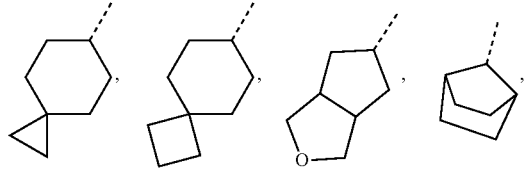
,
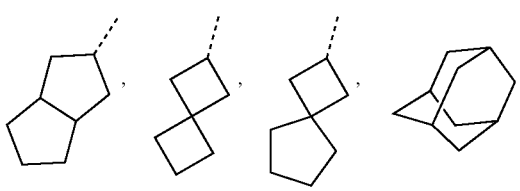
,
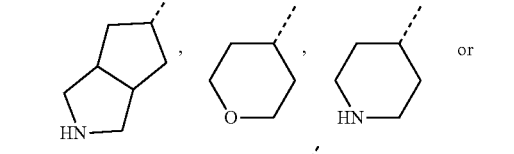
,
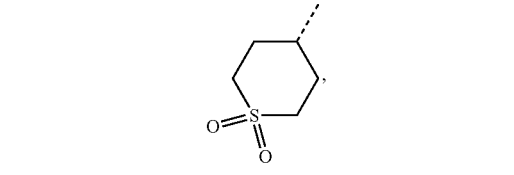
, 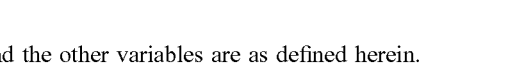 or 

and the other variables are as defined herein.

In some embodiments of the present disclosure, the structural moiety

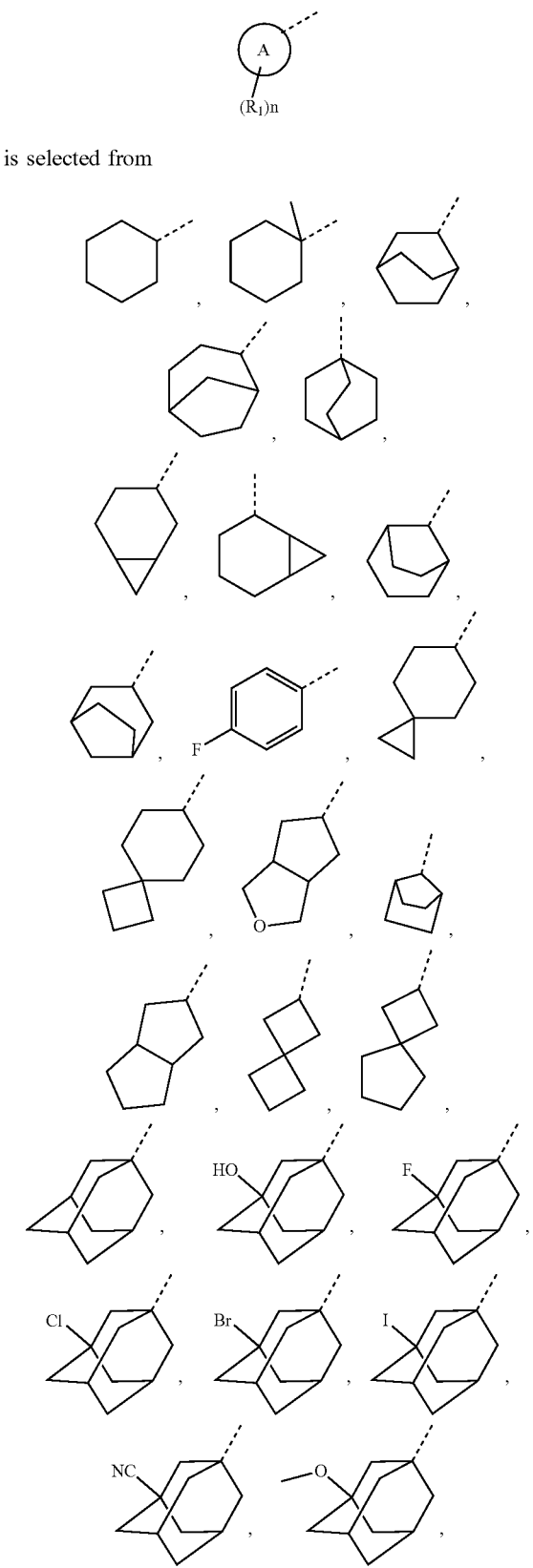

is selected from

-continued

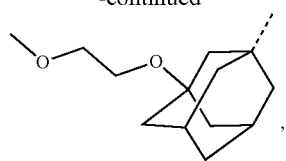
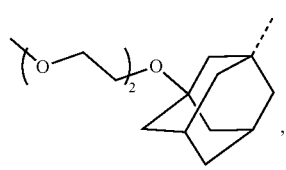
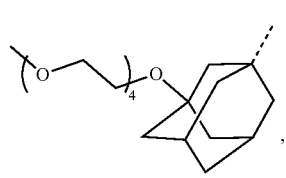
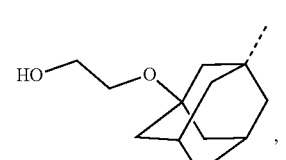
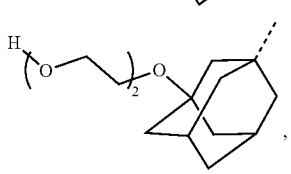
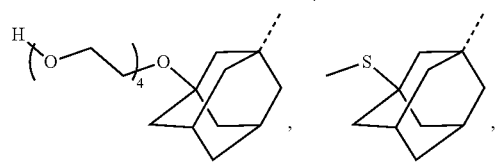
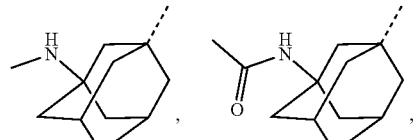
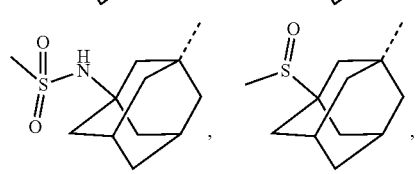
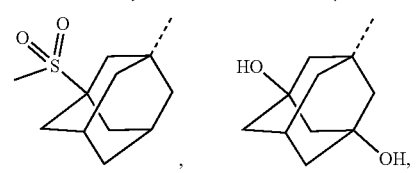
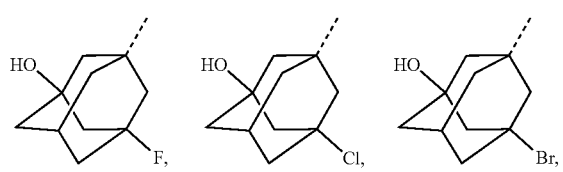

-continued

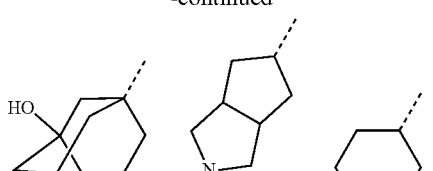

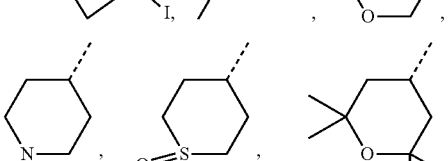

and the other variables are as defined herein.

In some embodiments of the present disclosure, the $R_a$ is selected from H and methyl, and the other variables are as defined herein.

In some embodiments of the present disclosure, the structural moiety

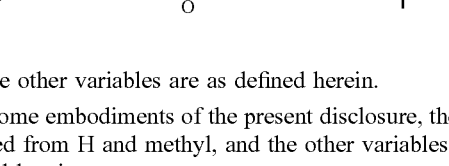

is selected from

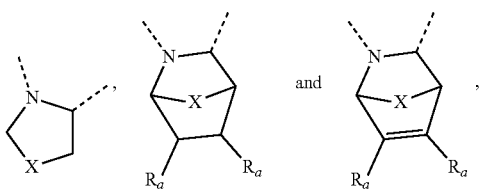

and the other variables are as defined herein.

In some embodiments of the present disclosure, the structural moiety

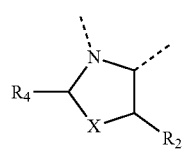

is selected from

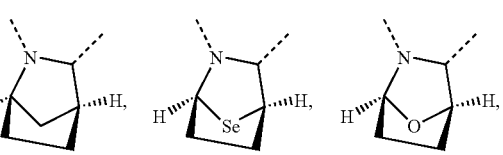

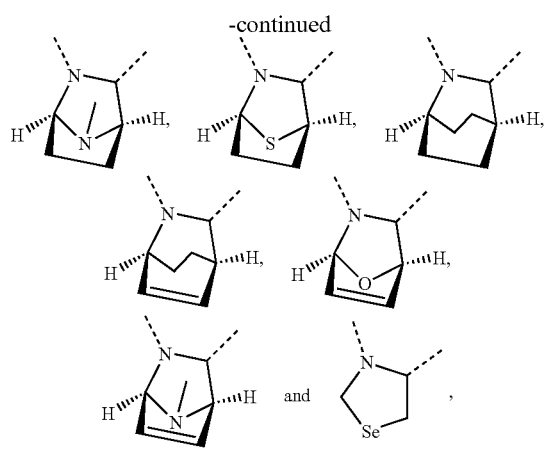

and the other variables are as defined herein.

The present disclosure also provides the compound or the pharmaceutically acceptable salt thereof, and the compound is selected from:

(IV-1)

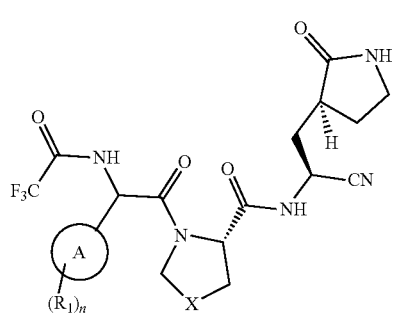

(IV-2)

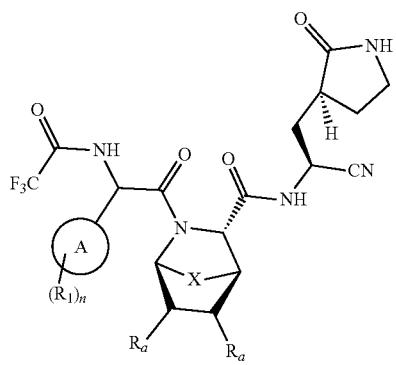

(IV-3)

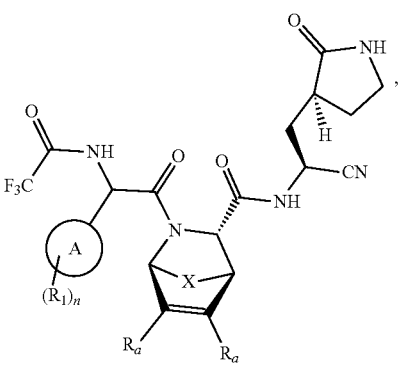

wherein, $R_1$, $R_a$, n, X and ring A are as defined herein.

The present disclosure also provides the compound or the pharmaceutically acceptable salt thereof, and the compound is selected from:

(IV-1a)

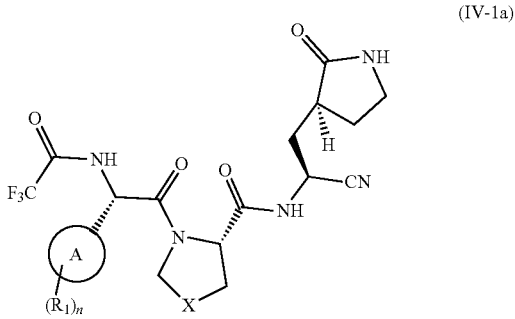

(IV-1b)

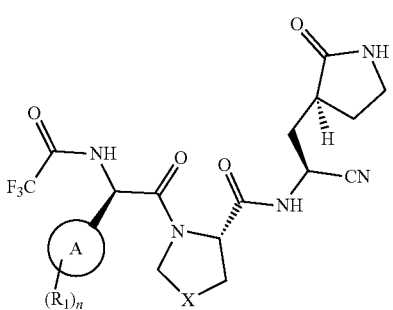

(IV-2a)

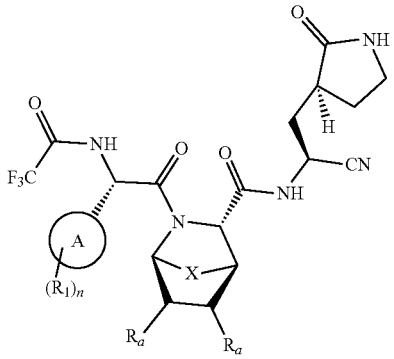

(IV-2b)

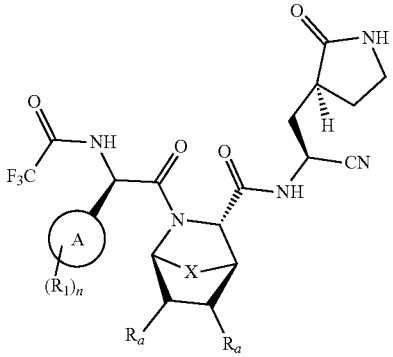

-continued

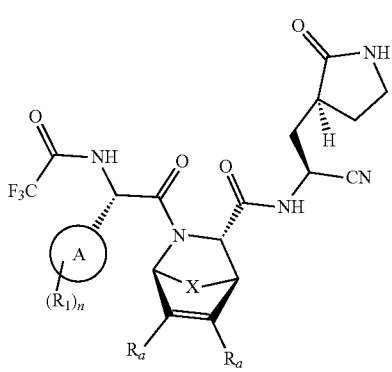
(IV-3a)

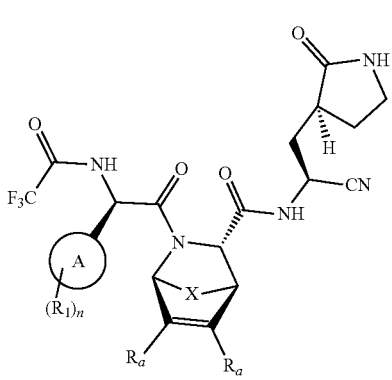
(IV-3b)

wherein, $R_1$, $R_a$, n, X and ring A are as defined herein.

The present disclosure provides a compound represented by formula (VIII) or a pharmaceutically acceptable salt thereof,

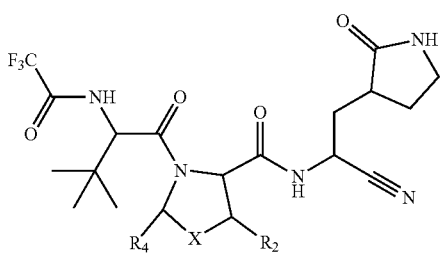
(VIII)

wherein,

X is selected from —CH($R_3$)—, —CH$_2$CH$_2$—, O, S, Se, SO$_2$ and —N($R_3$)—, and the —CH$_2$CH$_2$— is optionally substituted by 1, 2, 3 or 4 R;

R is each independently selected from halogen, OH, NH$_2$, CN, $C_{1-3}$ alkyl and $C_{1-3}$ haloalkyl;

$R_3$ is each independently selected from H, $C_{1-3}$ alkyl, $C_{1-3}$ alkoxy, $C_{1-3}$ haloalkyl, $C_{1-3}$ haloalkoxy, $C_{6-10}$ aryl and 5- to 10-membered heteroaryl, and the $C_{6-10}$ aryl and 5- to 10-membered heteroaryl are optionally substituted by 1, 2 or 3 $R_{31}$;

$R_2$ and $R_4$ are each independently selected from H, $C_{1-3}$ alkyl, $C_{1-3}$ alkoxy, $C_{1-3}$ haloalkyl, $C_{1-3}$ haloalkoxy, $C_{6-10}$ aryl and 5- to 10-membered heteroaryl, and the $C_{6-10}$ aryl and 5- to 10-membered heteroaryl are optionally substituted by 1, 2 or 3 $R_{21}$;

or, $R_2$ and $R_4$ together with the atoms to which they are attached form $C_{5-8}$ cycloalkyl, 5- to 6-membered heterocycloalkyl and 5- to 6-membered heterocycloalkenyl, and the $C_{5-8}$ cycloalkyl, 5- to 6-membered heterocycloalkyl and 5- to 6-membered heterocycloalkenyl are optionally and independently substituted by 1 or 2 $R_a$;

$R_a$ is each independently selected from H, halogen, $C_{1-3}$ alkyl, $C_{1-3}$ alkoxy, $C_{1-3}$ haloalkoxy, $C_{6-10}$ aryl and 5- to 10-membered heteroaryl, and the $C_{6-10}$ aryl and 5- to 10-membered heteroaryl are optionally substituted by 1, 2 or 3 $R_{41}$;

$R_{21}$, $R_{31}$ and $R_{41}$ are each independently selected from halogen, OH, NH$_2$, CN, $C_{1-3}$ alkyl, $C_{1-3}$ alkoxy, $C_{1-3}$ haloalkyl and $C_{1-3}$ haloalkoxy;

the "heterocycloalkyl", "heterocycloalkenyl" and "heteroaryl" contain 1, 2 or 3 heteroatoms or heteroatom groups independently selected from O, S, SO$_2$, N, P and Se.

In some embodiments of the present disclosure, the compound is selected from a structure represented by formula (VIII-1),

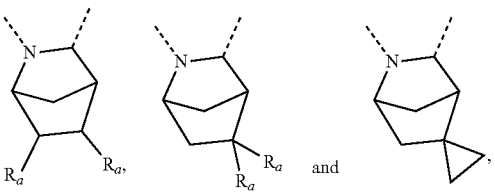
(VIII-1)

wherein, $R_2$ and $R_4$ together with the atoms to which they are attached form $C_{5-8}$ cycloalkyl, and the $C_{5-8}$ cycloalkyl is optionally substituted by 1 or 2 $R_a$;

$R_a$ is as defined herein.

In some embodiments of the present disclosure, the $R_a$ is each independently selected from H, F and CH$_3$, and the other variables are as defined herein.

In some embodiments of the present disclosure, the structural moiety is selected from and the other variables are as defined herein.

In some embodiments of the present disclosure, the structural moiety

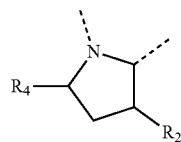

is selected from

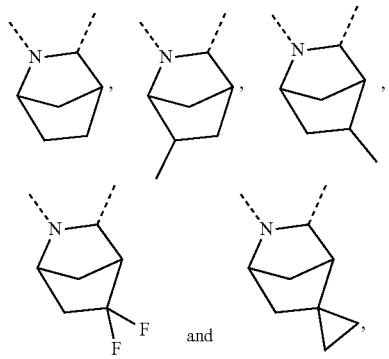

and the other variables are as defined herein.

In some embodiments of the present disclosure, the $R_b$ is each independently selected from H, F, methyl, ethyl, isopropyl, cyclopropyl and cyclobutyl, and the other variables are as defined herein.

In some embodiments of the present disclosure, the structural moiety

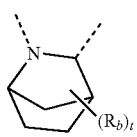

is selected from

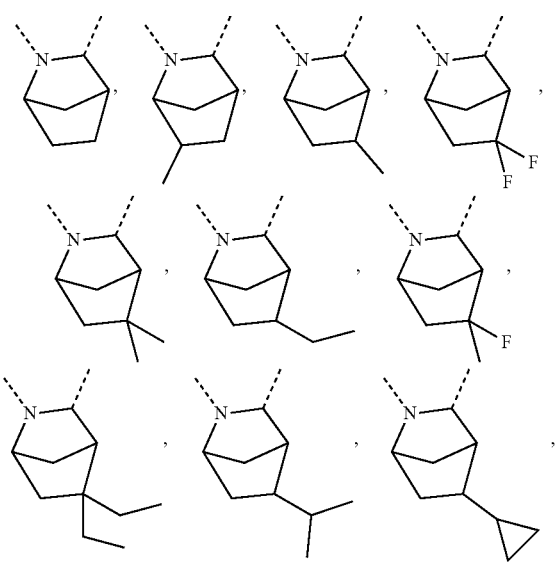

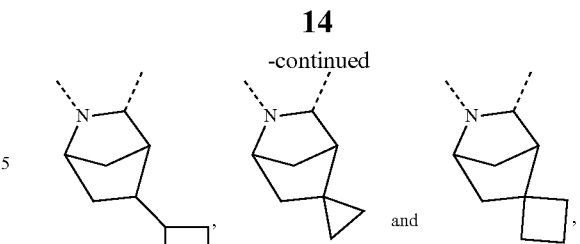

and the other variables are as defined herein.

In some embodiments of the present disclosure, the structural moiety

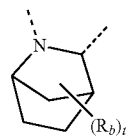

is selected from

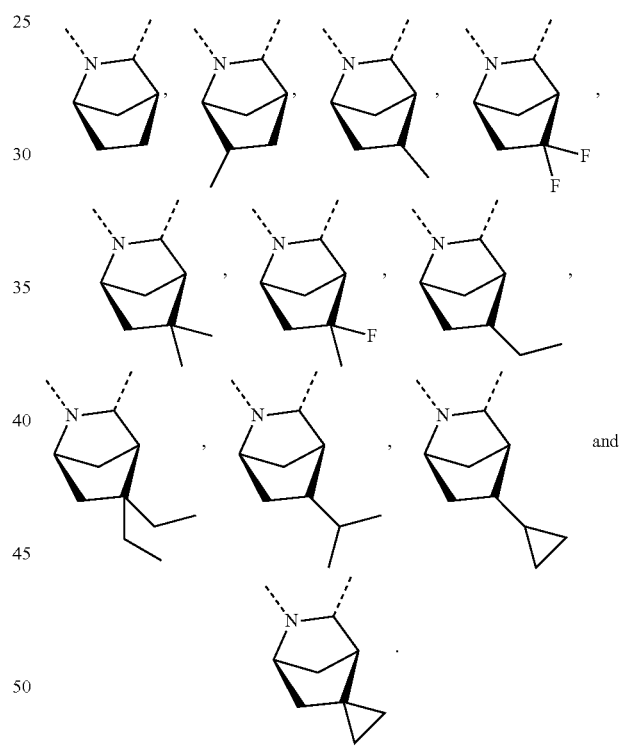

In some embodiments of the present disclosure, the $R_1$ is each independently selected from halogen, $C_{1-3}$ alkyl, $C_{1-3}$ alkoxy, $C_{1-3}$ haloalkyl and $C_{1-3}$ haloalkoxy, and the other variables are as defined herein.

In some embodiments of the present disclosure, the $R_1$ is each independently selected from F, Cl and methyl, and the other variables are as defined herein.

In some embodiments of the present disclosure, the ring A is selected from $C_{5-10}$ cycloalkyl and phenyl, and the other variables are as defined herein.

In some embodiments of the present disclosure, the ring A is selected from cyclohexyl, spiro[3.3]heptyl, bicyclo[2.2.2]octyl, adamantyl and phenyl, and the other variables are as defined herein.

In some embodiments of the present disclosure, the ring A is selected from

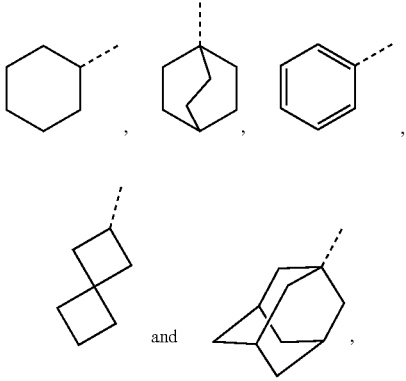

and the other variables are as defined herein.

In some embodiments of the present disclosure, the structural moiety

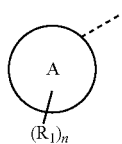

is selected from

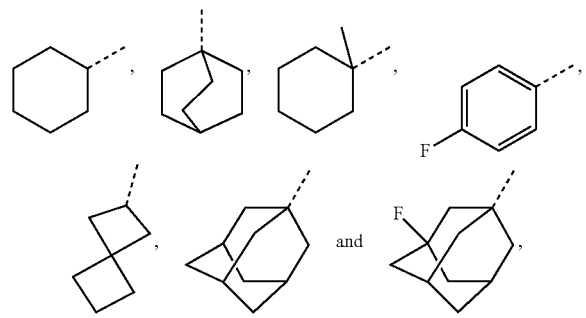

and the other variables are as defined herein.

In some embodiments of the present disclosure, the $R_5$ is selected from —$CF_3$, —$OCH_3$,

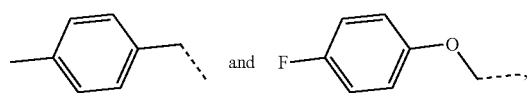

and the other variables are as defined herein.

The present disclosure provides a compound represented by the following formula or a pharmaceutically acceptable salt thereof, and the compound is selected from:

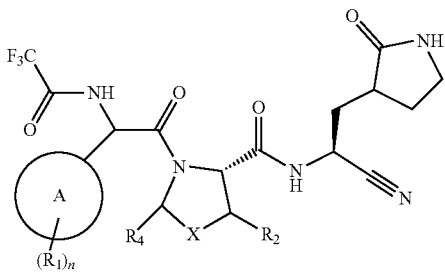

wherein, ring A is selected from $C_{3-10}$ cycloalkyl, 3- to 10-membered heterocycloalkyl, $C_{6-10}$ aryl and 5- to 10-membered heteroaryl;

$R_1$ is each independently selected from halogen, $OR_{11}$, CN, $CH_3S(O)_m$—, —$NH(R_{12})$, $C_{1-3}$ alkyl and $C_{1-3}$ haloalkyl;

$R_{11}$ is selected from H, $C_{1-3}$ alkyl, $C_{1-3}$ haloalkyl, $CH_3(OCH_2CH_2)_p$— and $H(OCH_2CH_2)_q$—;

$R_{12}$ is selected from $C_{1-3}$ alkyl, $C_{1-3}$ haloalkyl, $CH_3CO$— and $CH_3SO_2$—;

m is selected from 0, 1 and 2;

p and q are selected from 1, 2, 3, 4, 5 and 6;

n is selected from 0, 1, 2, 3 and 4;

X is selected from —$CH(R_3)$—, —$CH_2CH_2$—, O, S, Se, $SO_2$ and —$N(R_3)$—, and the —$CH_2CH_2$— is optionally substituted by 1, 2, 3 or 4 R;

R is each independently selected from halogen, OH, $NH_2$, CN, $C_{1-3}$ alkyl and $C_{1-3}$ haloalkyl;

$R_3$ is each independently selected from H, $C_{1-3}$ alkyl, $C_{1-3}$ alkoxy, $C_{1-3}$ haloalkyl, $C_{1-3}$ haloalkoxy, $C_{6-10}$ aryl and 5- to 10-membered heteroaryl, and the $C_{6-10}$ aryl and 5- to 10-membered heteroaryl are optionally substituted by 1, 2 or 3 $R_{31}$;

$R_2$ and $R_4$ are each independently selected from H, $C_{1-3}$ alkyl, $C_{1-3}$ alkoxy, $C_{1-3}$ haloalkyl, $C_{1-3}$ haloalkoxy, $C_{6-10}$ aryl and 5- to 10-membered heteroaryl, and the $C_{6-10}$ aryl and 5- to 10-membered heteroaryl are optionally substituted by 1, 2 or 3 $R_{21}$;

or, $R_2$ and $R_4$ together with the atoms to which they are attached form $C_{5-8}$ cycloalkyl, 5- to 6-membered heterocycloalkyl and 5- to 6-membered heterocycloalkenyl, and the $C_{5-8}$ cycloalkyl, 5- to 6-membered heterocycloalkyl and 5- to 6-membered heterocycloalkenyl are optionally substituted by 1 or 2 $R_a$;

$R_a$ is each independently selected from H, halogen, $C_{1-3}$ alkyl, $C_{1-3}$ alkoxy, $C_{1-3}$ haloalkoxy, $C_{6-10}$ aryl and 5- to 10-membered heteroaryl, and the $C_{6-10}$ aryl and 5- to 10-membered heteroaryl are optionally substituted by 1, 2 or 3 $R_{41}$;

$R_{21}$, $R_{31}$ and $R_{41}$ are each independently selected from halogen, OH, $NH_2$, CN, $C_{1-3}$ alkyl, $C_{1-3}$ alkoxy, $C_{1-3}$ haloalkyl and $C_{1-3}$ haloalkoxy;

the "heterocycloalkyl", "heterocycloalkenyl" and "heteroaryl" contain 1, 2 or 3 heteroatoms or heteroatom groups independently selected from O, S, $SO_2$, N, P and Se.

In some embodiments of the present disclosure, the $R_1$ is selected from F, Cl, Br, I, methyl, OH, CN, $CH_3O$—, $CH_3S$—, $CH_3S(O)$—, $CH_3SO_2$—, $CH_3NH$—, $CH_3CONH$—, $CH_3SO_2NH$—, $CH_3OCH_2CH_2O$—, $CH_3$ (OCH$_2$CH$_2$)$_2$O—, CH$_3$(OCH$_2$CH$_2$)$_4$O—, HOCH$_2$CH$_2$O—, H(OCH$_2$CH$_2$)$_2$O— and H(OCH$_2$CH$_2$)$_4$O—, and the other variables are as defined herein.

In some embodiments of the present disclosure, the ring A is selected from C$_{5-9}$ cycloalkyl, 5- to 8-membered heterocycloalkyl, adamantyl and phenyl, and the other variables are as defined herein.

In some embodiments of the present disclosure, the ring A is selected from

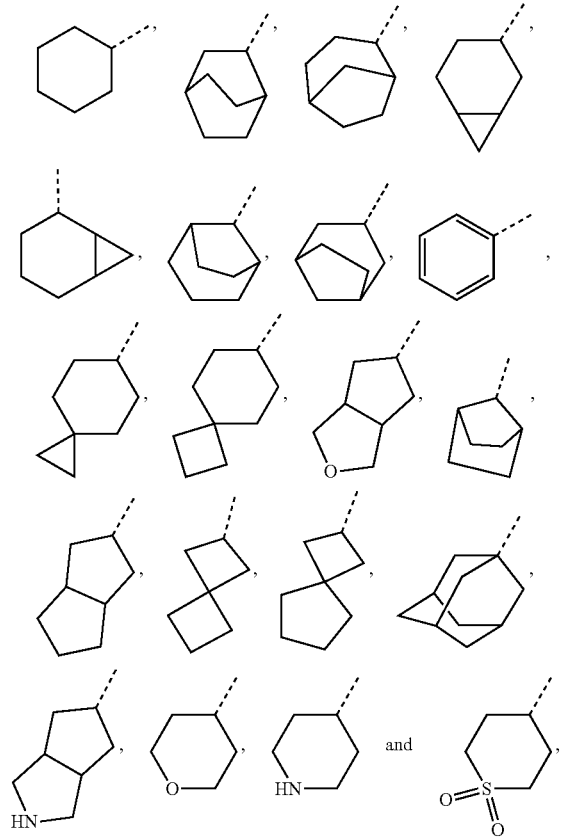

and the other variables are as defined herein.

In some embodiments of the present disclosure, the structural moiety

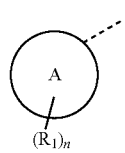

is selected from

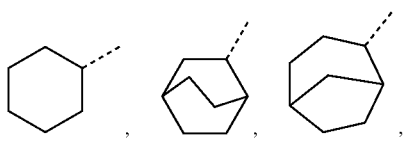

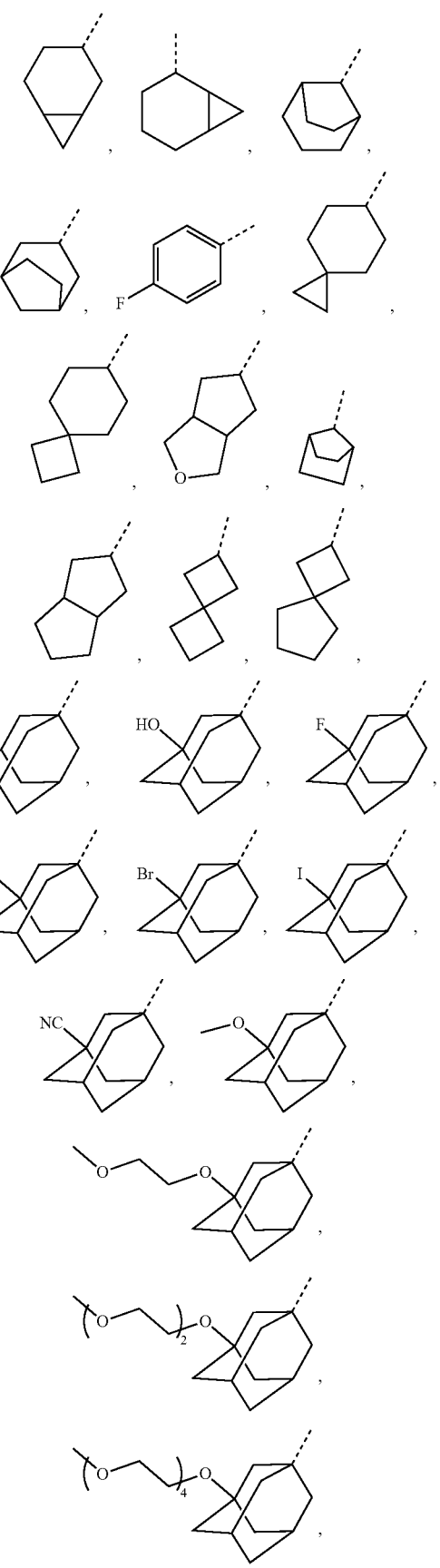

-continued

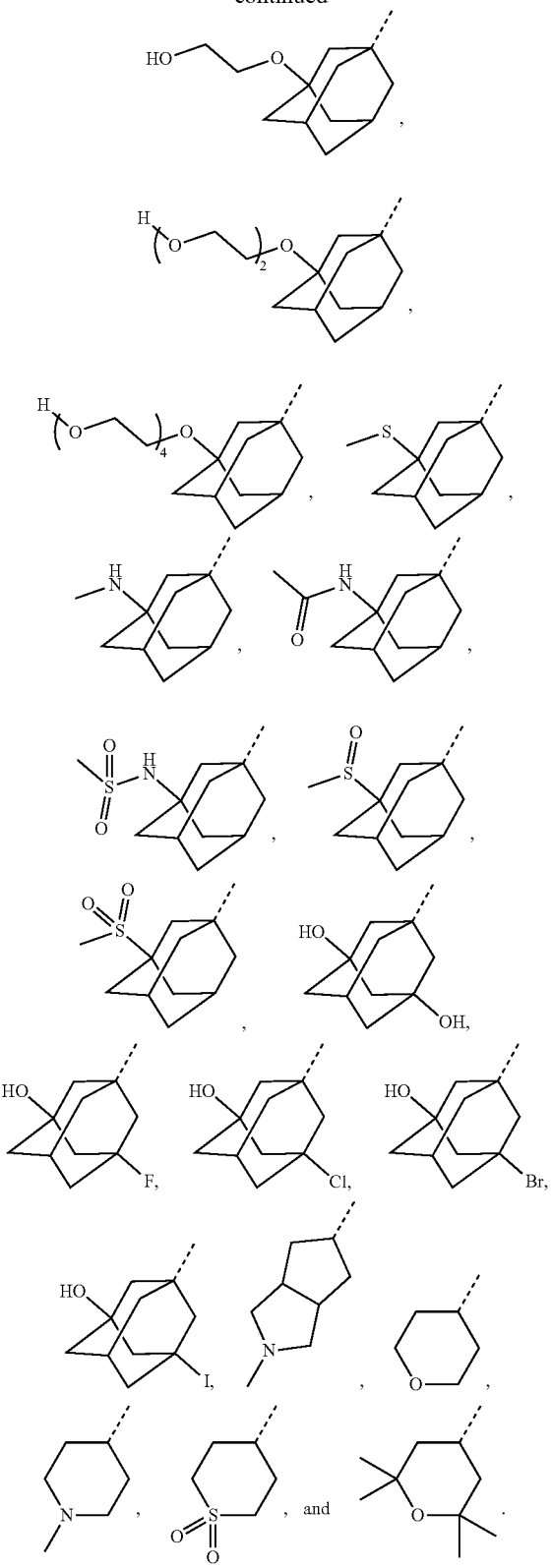

and the other variables are as defined herein.

In some embodiments of the present disclosure, the $R_a$ is selected from H and methyl, and the other variables are as defined herein.

In some embodiments of the present disclosure, the structural moiety

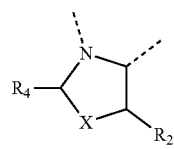

is selected from

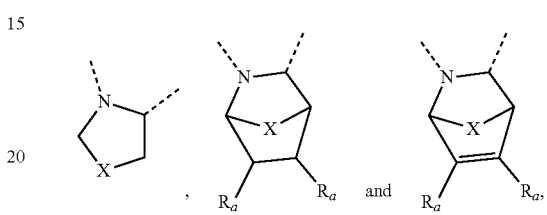

and the other variables are as defined herein.

In some embodiments of the present disclosure, the structural moiety

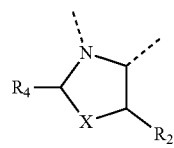

is selected from

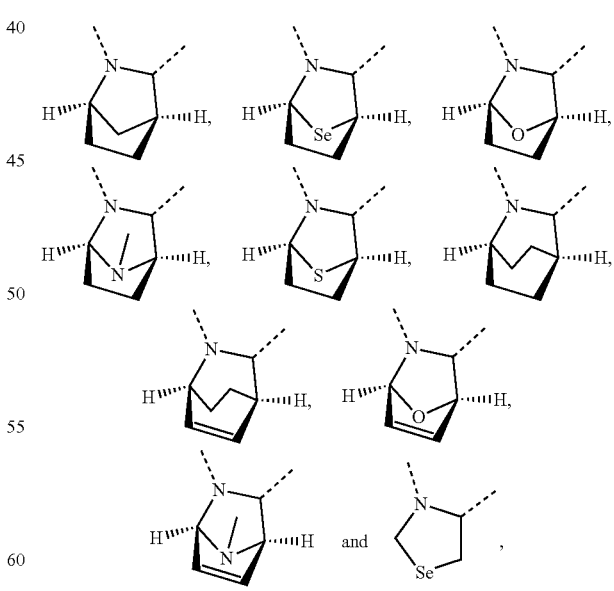

and the other variables are as defined herein.

The present disclosure provides a compound represented by the following formula or a pharmaceutically acceptable salt thereof, and the compound is selected from:

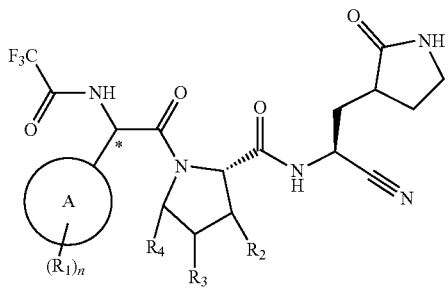

wherein,
ring A is selected from $C_{3-10}$ cycloalkyl, 3- to 10-membered heterocycloalkyl and phenyl;
$R_1$ is each independently selected from halogen and $C_{1-3}$ alkyl, and the $C_{1-3}$ alkyl is optionally substituted by 1, 2 or 3 F;
n is selected from 0, 1, 2, 3 and 4;
$R_2$ is H, $R_3$ and $R_4$ together with the carbon atoms to which they are attached form $C_{3-6}$ cycloalkyl, and the $C_{3-6}$ cycloalkyl is optionally substituted by 1 or 2 $R_a$; or,
$R_3$ is H, $R_2$ and $R_4$ together with the carbon atoms to which they are attached form $C_{5-8}$ cycloalkyl, and the $C_{5-8}$ cycloalkyl is optionally substituted by 1 or 2 $R_a$;
$R_a$ is each independently selected from H and $C_{1-3}$ alkyl;
the "heterocycloalkyl" contains 1, 2 or 3 heteroatoms independently selected from O, S, N, P and Se;
the carbon atom with "*" is a chiral carbon atom, which exists in a form of (R) or (S) single enantiomer or in a form rich in one enantiomer.

The present disclosure provides a compound represented by the following formula or a pharmaceutically acceptable salt thereof, and the compound is selected from:

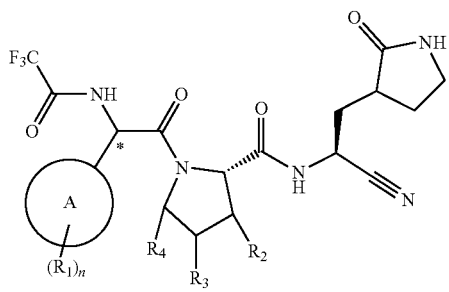

wherein,
ring A is selected from $C_{3-10}$ cycloalkyl, 3- to 10-membered heterocycloalkyl and phenyl;
$R_1$ is each independently selected from halogen, $OR_{11}$, CN, $CH_3S(O)_m$—, $NHR_{12}$ and $C_{1-3}$ alkyl, and the $C_{1-3}$ alkyl is optionally substituted by 1, 2 or 3 F;
$R_{11}$ is selected from H, $C_{1-3}$ alkyl, $CH_3(OCH_2CH_2)_p$— and $H(OCH_2CH_2)_q$—, and the $C_{1-3}$ alkyl is optionally substituted by 1, 2 or 3 halogens;
$R_{12}$ is selected from $C_{1-3}$ alkyl, $CH_3CO$— and $CH_3SO_2$—, and the $C_{1-3}$ alkyl is optionally substituted by 1, 2 or 3 halogens;
m is selected from 0, 1 and 2;
p and q are selected from 1, 2, 3, 4, 5 and 6;
n is selected from 0, 1, 2, 3 and 4;

$R_2$ is H, $R_3$ and $R_4$ together with the carbon atoms to which they are attached form $C_{3-6}$ cycloalkyl, and the $C_{3-6}$ cycloalkyl is optionally substituted by 1 or 2 $R_a$; or,
$R_3$ is H, $R_2$ and $R_4$ together with the carbon atoms to which they are attached form $C_{5-8}$ cycloalkyl, and the $C_{5-8}$ cycloalkyl is optionally substituted by 1 or 2 $R_a$;
$R_a$ is each independently selected from H and $C_{1-3}$ alkyl;
the "heterocycloalkyl" contains 1, 2 or 3 heteroatoms or heteroatom groups independently selected from O, S, $SO_2$, N, P and Se;
the carbon atom with "*" is a chiral carbon atom, which exists in a form of (R) or (S) single enantiomer or in a form rich in one enantiomer.

In some embodiments of the present disclosure, the $R_1$ is selected from F, Cl, Br, I, methyl, OH, CN, $CH_3O$—, $CH_3S$—, $CH_3S(O)$—, $CH_3SO_2$—, $CH_3NH$—, $CH_3CONH$—, $CH_3SO_2NH$—, $CH_3OCH_2CH_2O$—, $CH_3(OCH_2CH_2)_2O$—, $CH_3(OCH_2CH_2)_4O$—, $HOCH_2CH_2O$—, $H(OCH_2CH_2)_2O$— and $H(OCH_2CH_2)_4O$—, and the other variables are as defined herein.

In some embodiments of the present disclosure, the $R_1$ is selected from F and methyl, and the other variables are as defined herein.

In some embodiments of the present disclosure, the ring A is selected from $C_{5-9}$ cycloalkyl, 5- to 8-membered heterocycloalkyl, adamantyl and phenyl, and the other variables are as defined herein.

In some embodiments of the present disclosure, the ring A is selected from

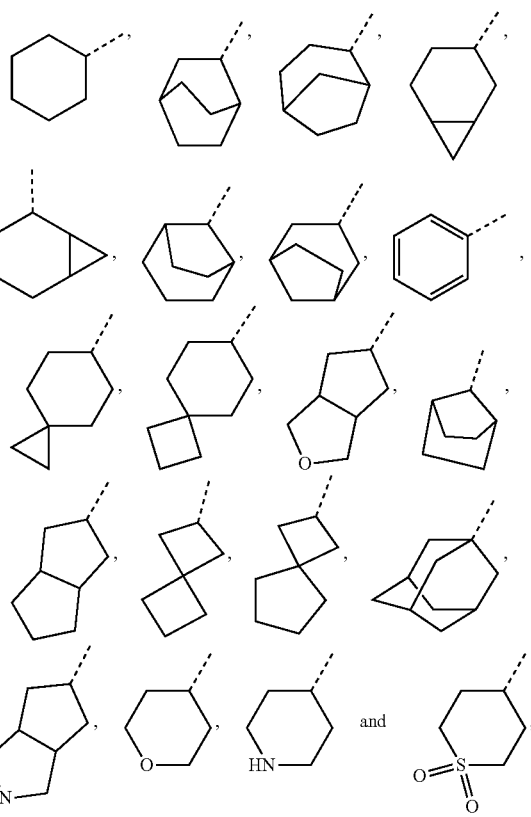

and the other variables are as defined herein.

In some embodiments of the present disclosure, the ring A is selected from $C_{5-9}$ cycloalkyl, 5- to 8-membered heterocycloalkyl and phenyl, and the other variables are as defined herein.
In some embodiments of the present disclosure, the structural moiety
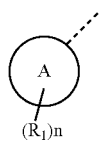
is selected from
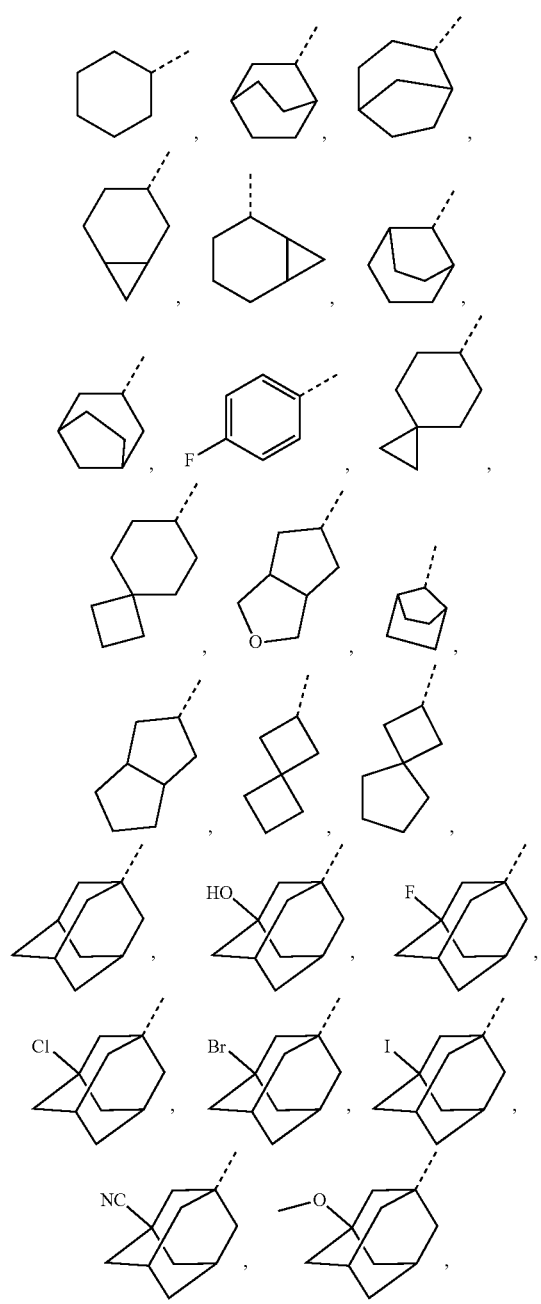
-continued
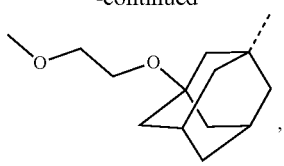
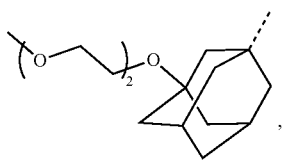
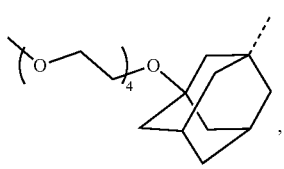
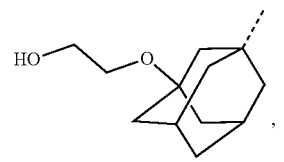
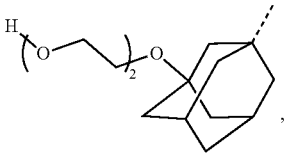
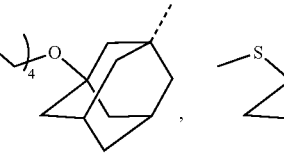
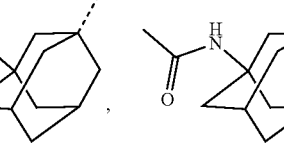
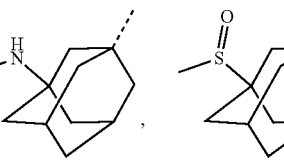
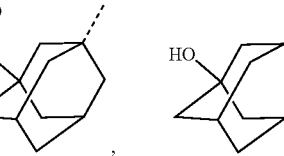
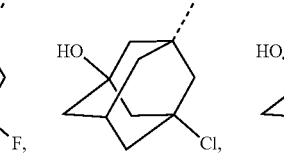

-continued

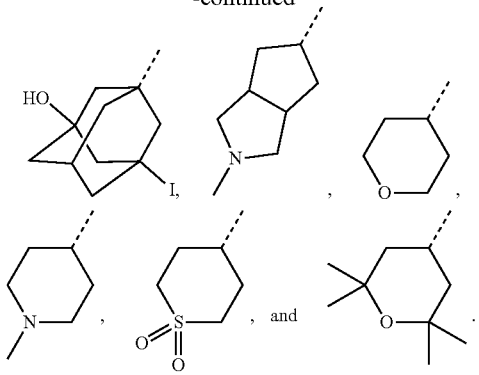

and the other variables are as defined herein.

In some embodiments of the present disclosure, the ring A is selected from

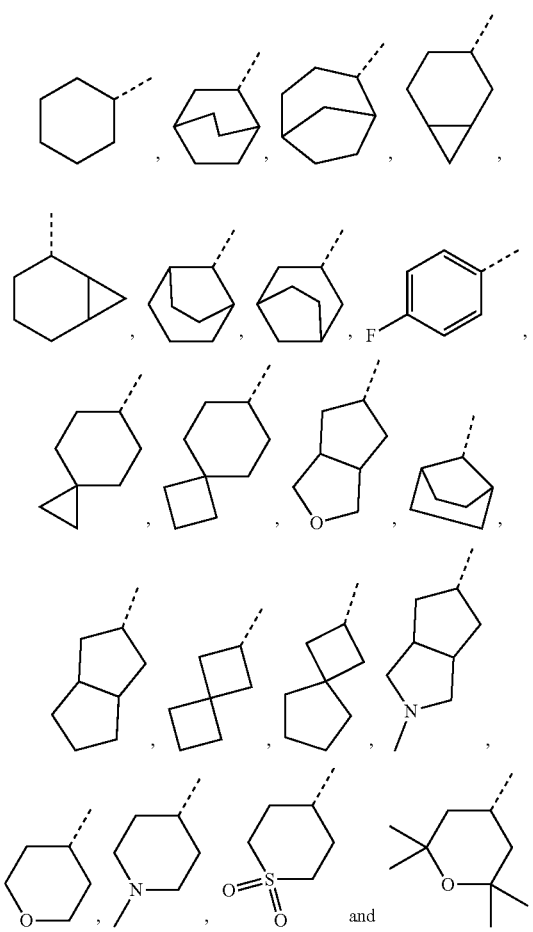

and the other variables are as defined herein.

In some embodiments of the present disclosure, the $R_a$ is selected from H and methyl, and the other variables are as defined herein.

In some embodiments of the present disclosure, the structural moiety

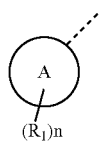

is selected from

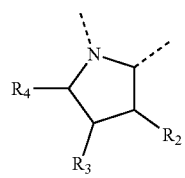

is selected from

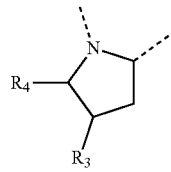

and

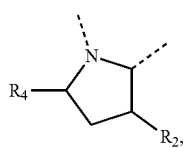

and the other variables are as defined herein.

In some embodiments of the present disclosure, the structural moiety

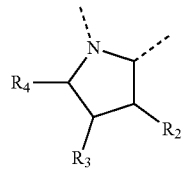

is selected from

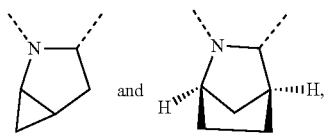

and the other variables are as defined herein.

The present disclosure also provides the compound or the pharmaceutically acceptable salt thereof, and the compound is selected from:

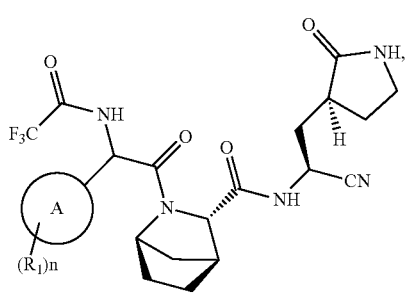
(I-1)

wherein, $R_1$, n and ring A are as defined herein.

The present disclosure provides a compound represented by the following formula or a pharmaceutically acceptable salt thereof, and the compound is selected from:

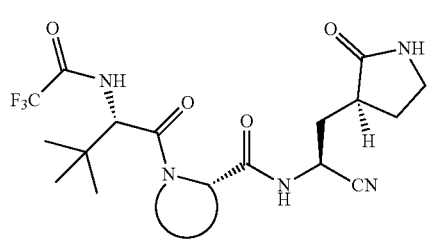
(I')

wherein,
the structural moiety

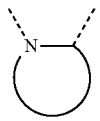

is selected from

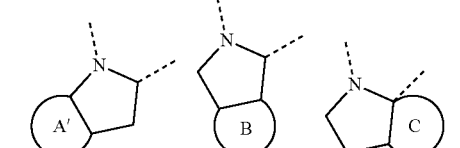

and

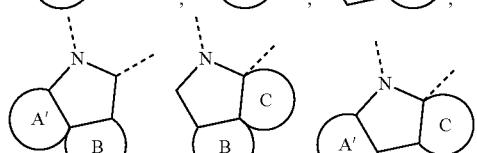

and the

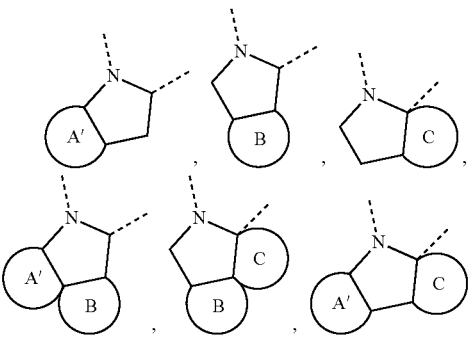

and

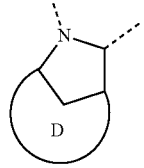

and are optionally and independently substituted by 1, 2 or 3 $R_a$;

ring A' is selected from $C_{3-6}$ cycloalkyl, and the $C_{3-6}$ cycloalkyl is optionally substituted by 1 or 2 $R_a$;

ring B is selected from $C_{4-8}$ cycloalkyl, $C_{5-8}$ cycloalkenyl, 3- to 8-membered heterocycloalkyl and 5- to 8-membered heterocycloalkenyl, and the $C_{4-8}$ cycloalkyl, $C_{5-8}$ cycloalkenyl, 3- to 8-membered heterocycloalkyl and 5- to 8-membered heterocycloalkenyl are optionally substituted by 1 or 2 $R_a$;

ring C is selected from

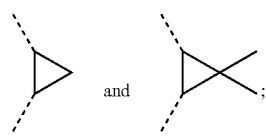

ring D is selected from $C_{4-8}$ cycloalkyl, $C_{5-8}$ cycloalkenyl and 5- to 8-membered heterocycloalkyl, and the $C_{4-8}$ cycloalkyl is optionally substituted by 1 or 2 $R_a$;

$R_{a'}$ is each independently selected from F and methyl;

the heterocycloalkyl contains 1, 2 or 3 heteroatoms or heteroatom groups independently selected from O, S, N and NH.

In some embodiments of the present disclosure, the compound is selected from formulas (I'-11), (I'-12), (I'-13), (I'-14), (I'-15), (I'-16) and (I'-17),

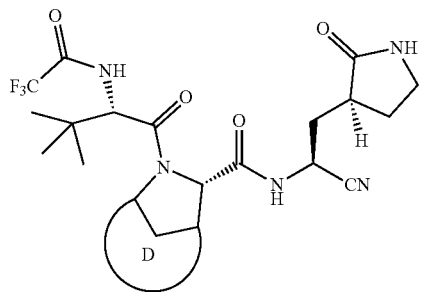

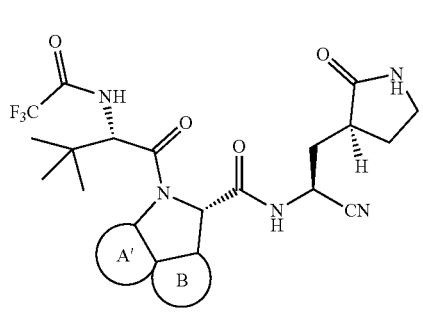

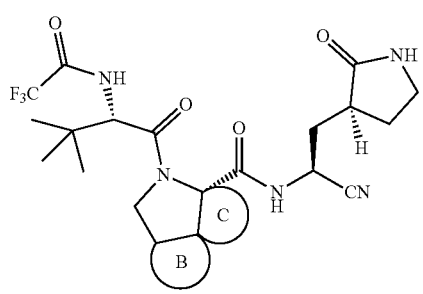

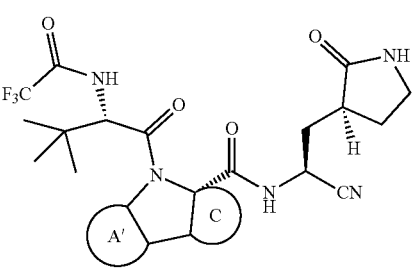

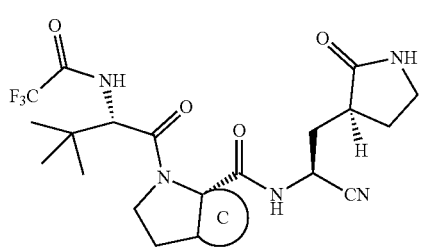

wherein, rings A', B, C and D are as defined herein.

In some embodiments of the present disclosure, the structural moiety

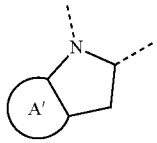

is selected from

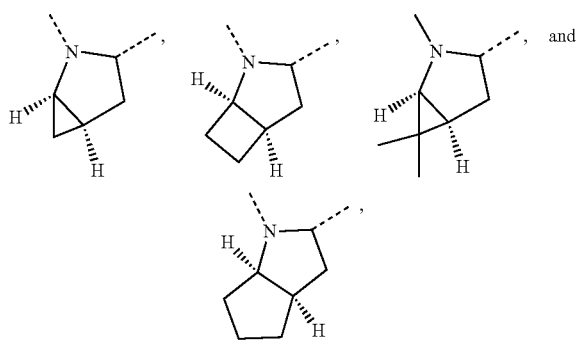

and the other variables are as defined herein.

In some embodiments of the present disclosure, the structural moiety

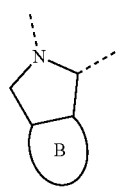

is selected from

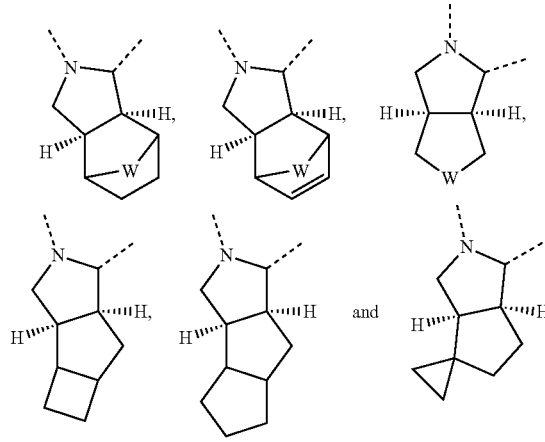

wherein W is selected from CH$_2$, NH, N(CH$_3$), O, S and SO$_2$, and the other variables are as defined herein.

In some embodiments of the present disclosure, the structural moiety

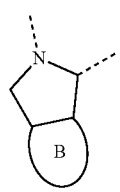

is selected from

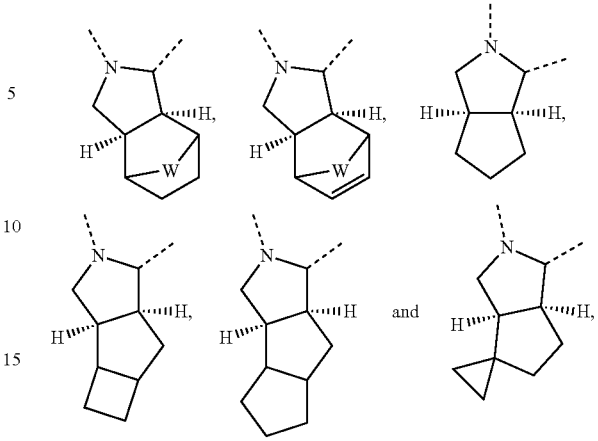

wherein W is selected from CH$_2$, NH, O and S, and the other variables are as defined herein.

In some embodiments of the present disclosure, the structural moiety

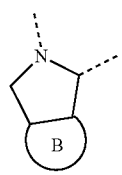

is selected from

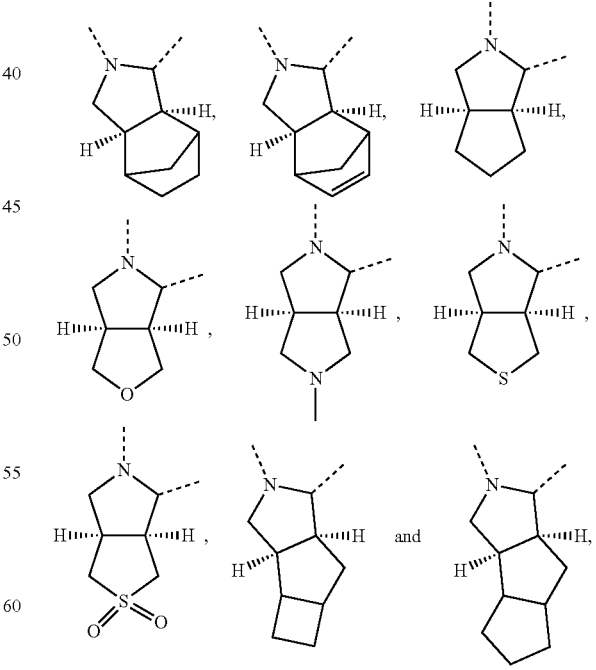

and the other variables are as defined herein.

In some embodiments of the present disclosure, the structural moiety is selected from

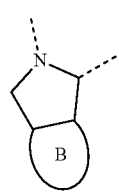

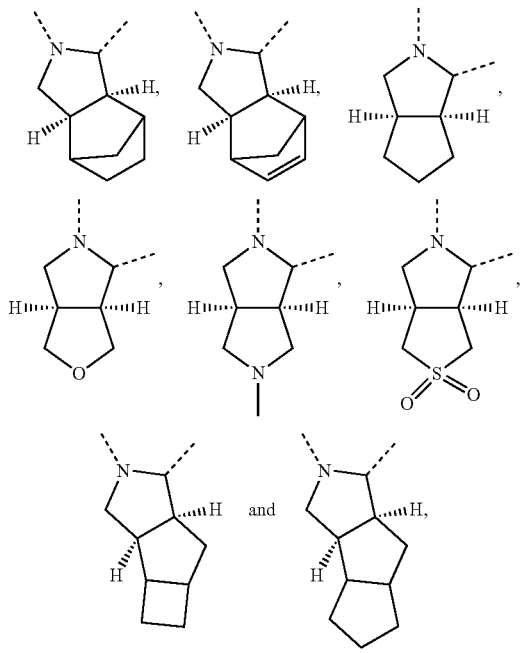

and
and the other variables are as defined herein.

In some embodiments of the present disclosure, the structural moiety

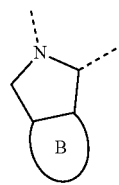

is selected from

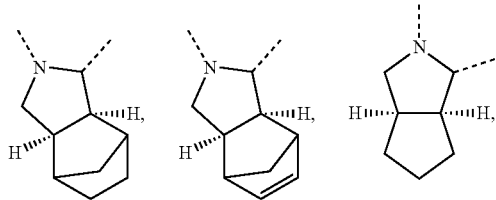

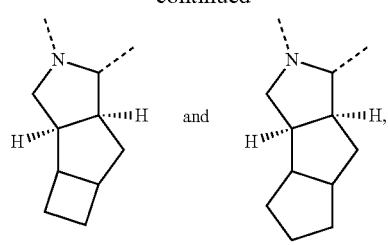

and the other variables are as defined herein.

In some embodiments of the present disclosure, the structural moiety

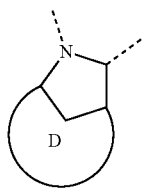

is selected from

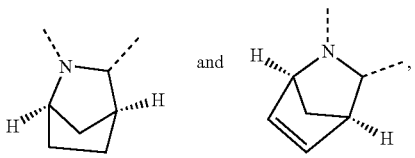

and the other variables are as defined herein.

Other embodiments of the present disclosure are derived from any combination of above variables.

The present disclosure provides a compound represented by the following formula or a pharmaceutically acceptable salt thereof, and the compound is selected from:

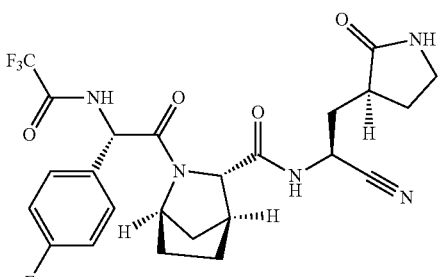

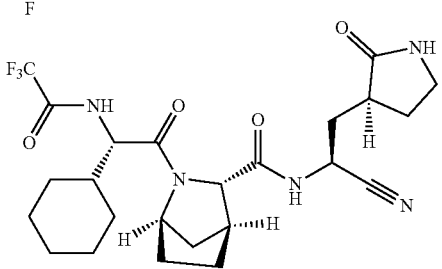

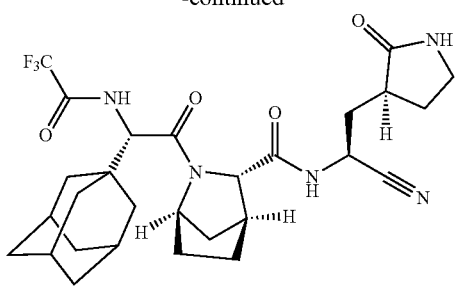
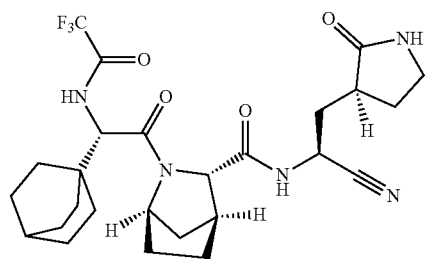
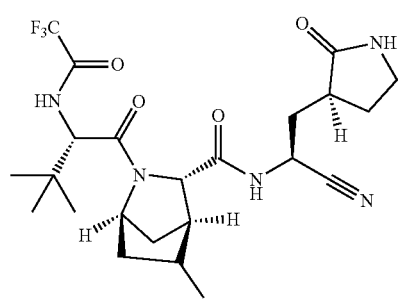
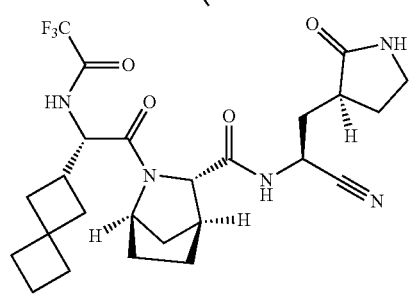
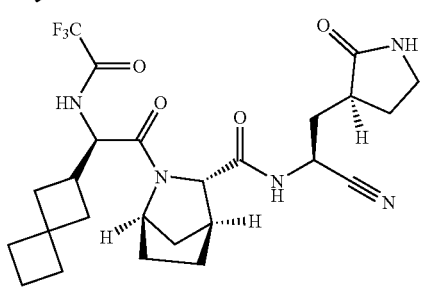
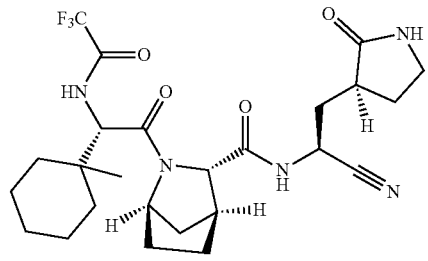
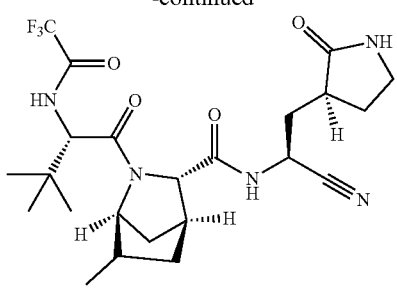
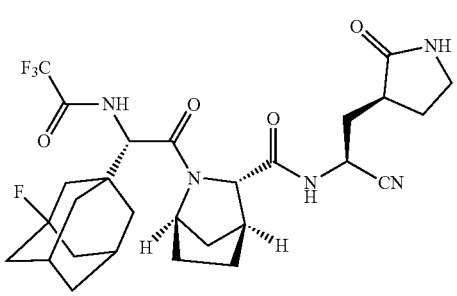
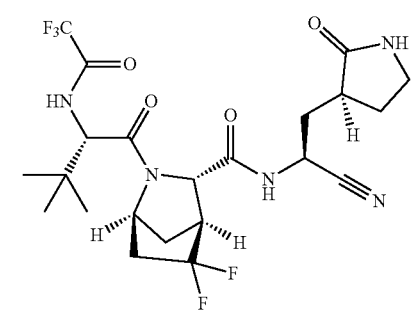
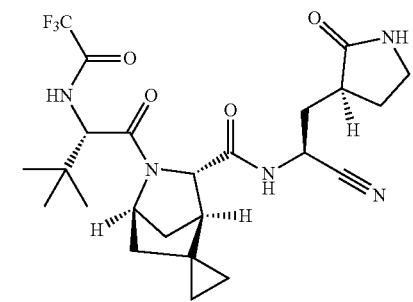
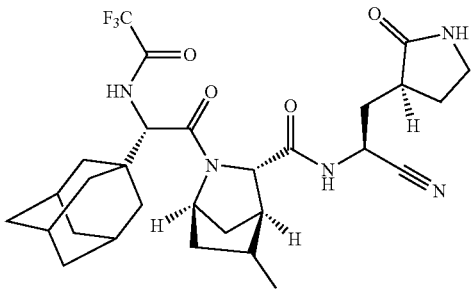

37
-continued
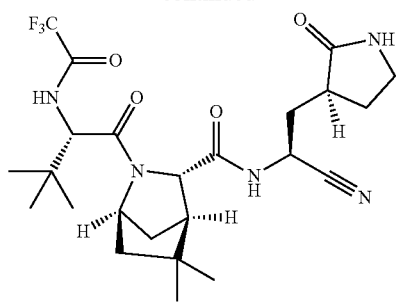
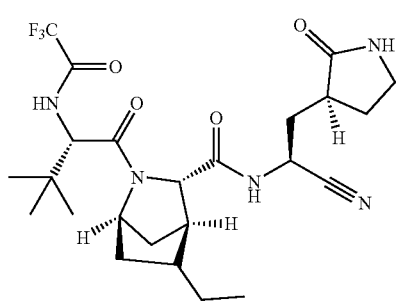
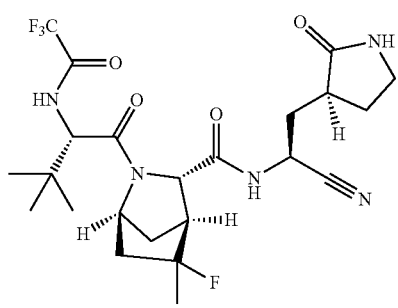
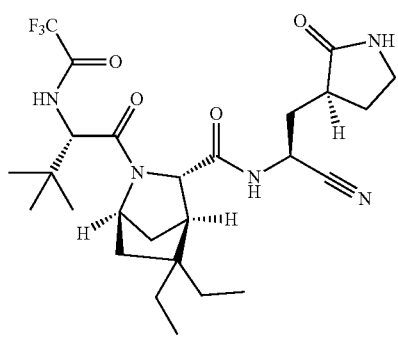
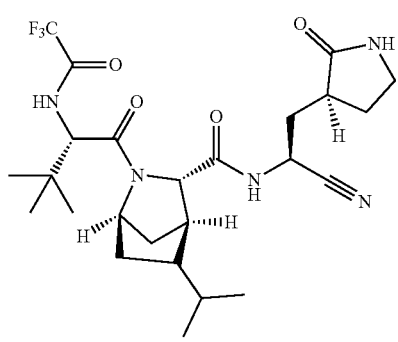
38
-continued
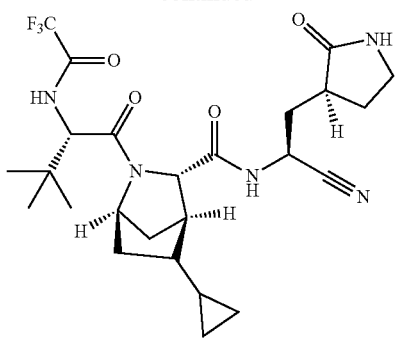
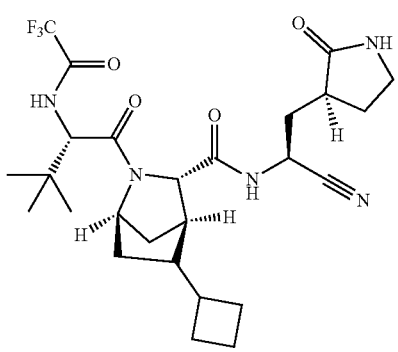
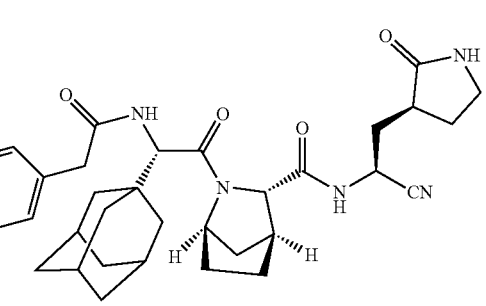
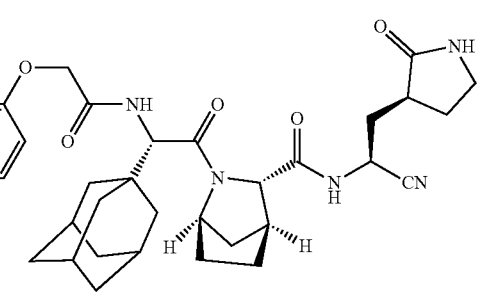
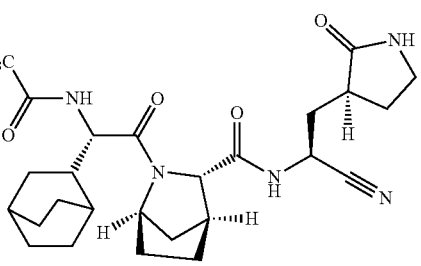

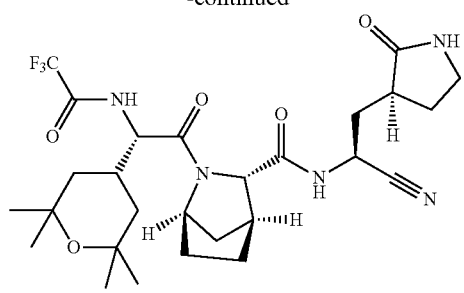
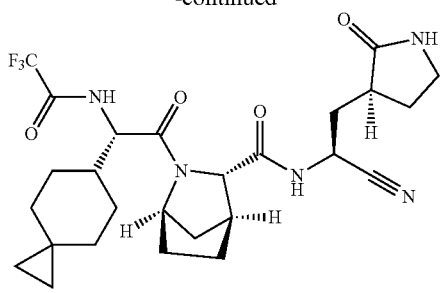
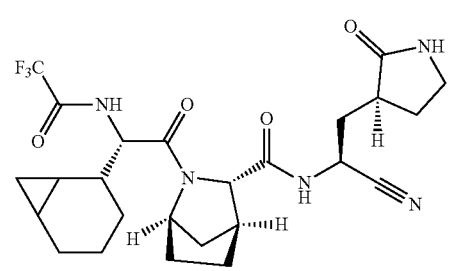 [SMILES: N#C[C@H](C[C@@H]1CCNC1=O)NC(=O)[C@@H]1[C@H]2CC[C@H](C2)N1C(=O)[C@@H](NC(=O)C(F)(F)F)C1CC2CCC1CC2]
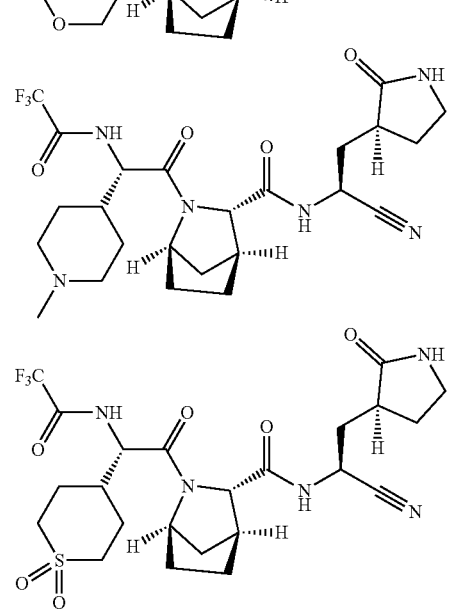
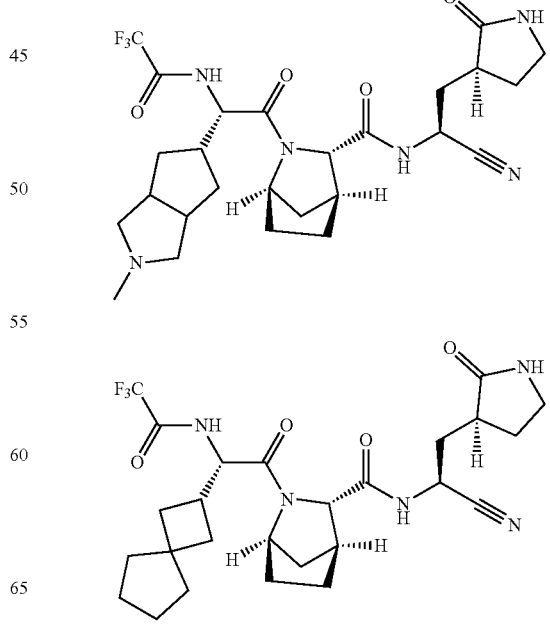

41
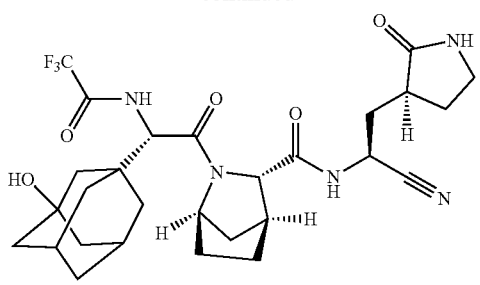
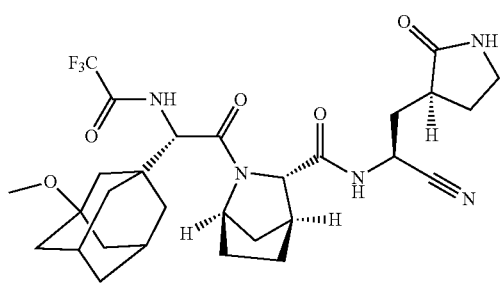
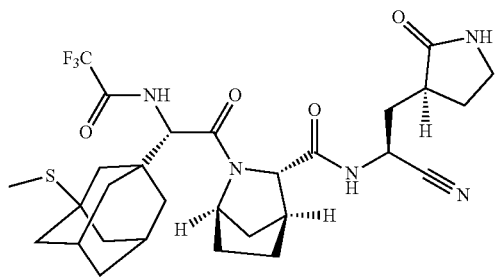
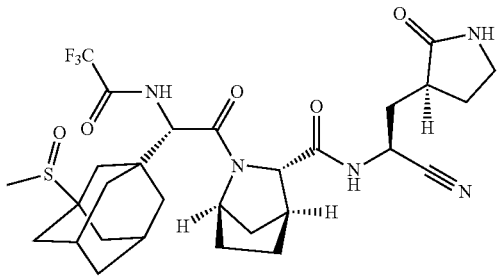
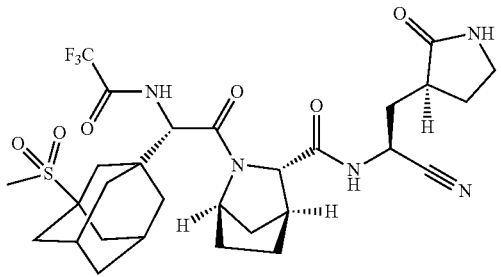
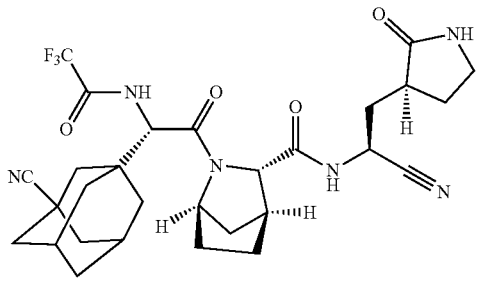
42
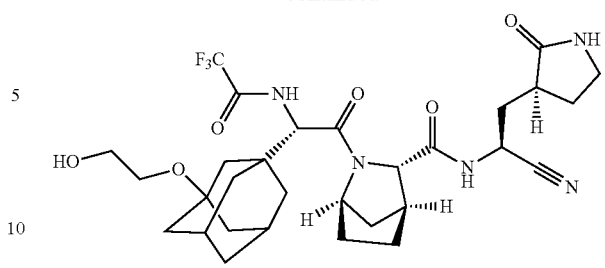
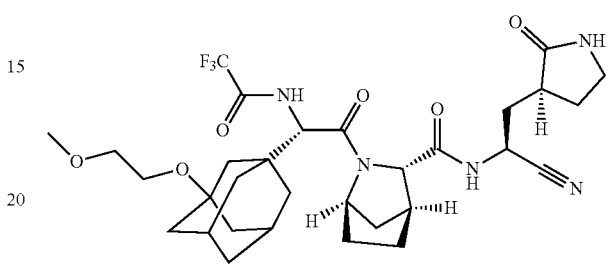
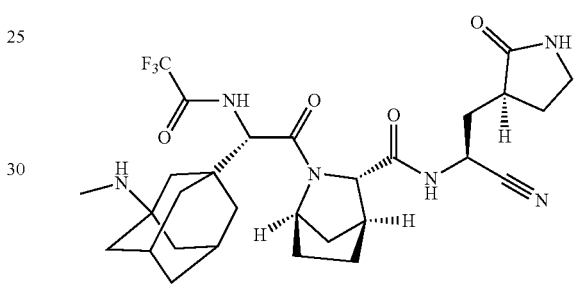
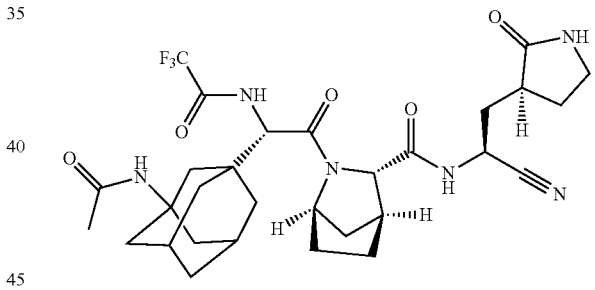
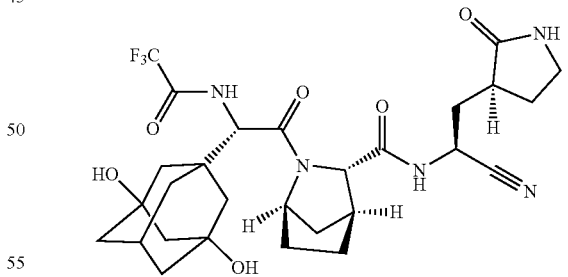
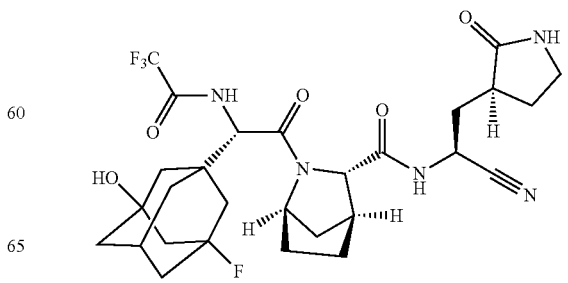

-continued
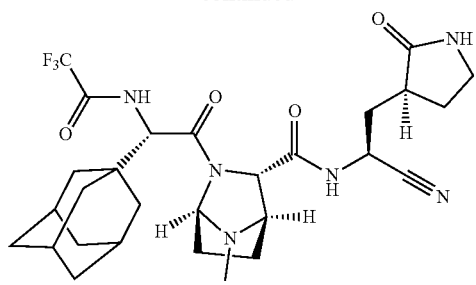
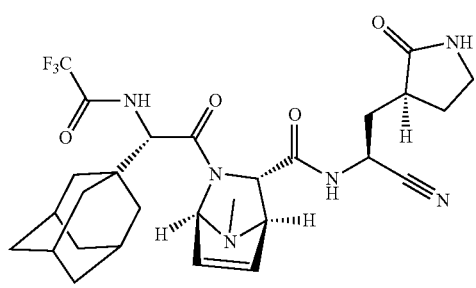
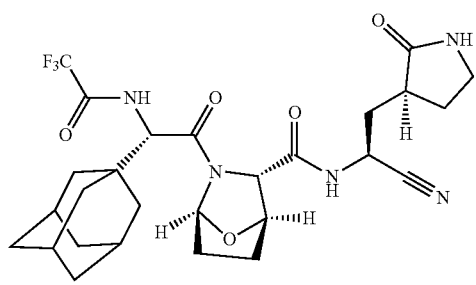
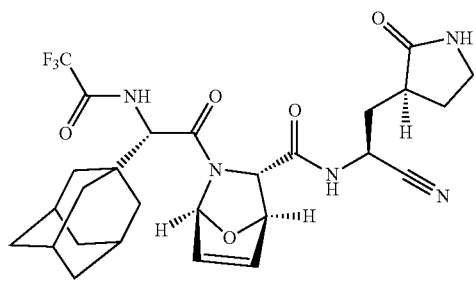
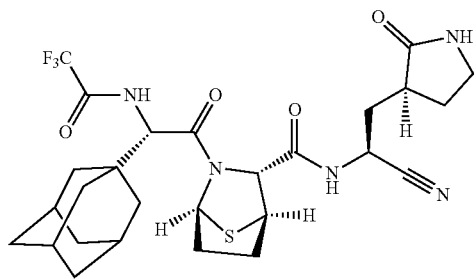
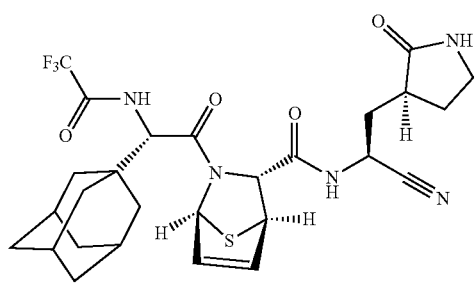
-continued
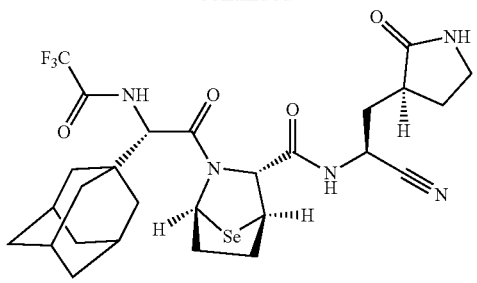
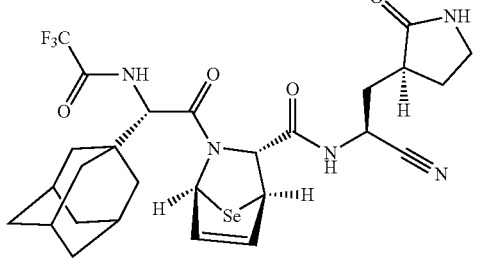
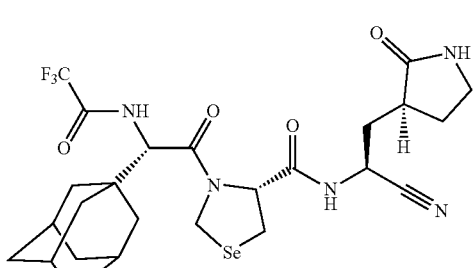
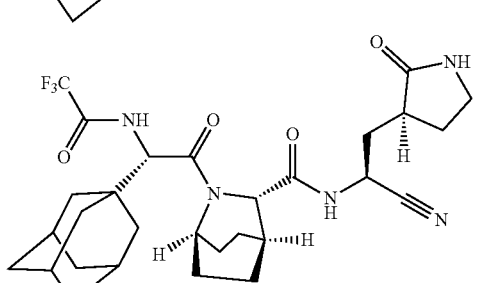
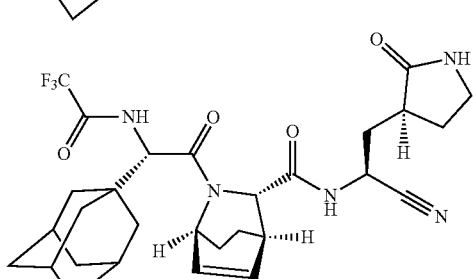
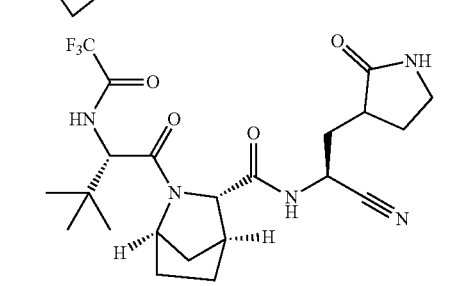

-continued
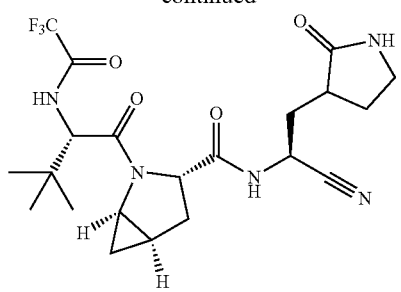
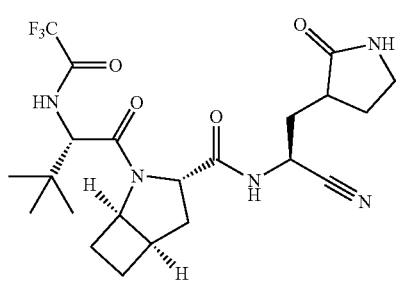
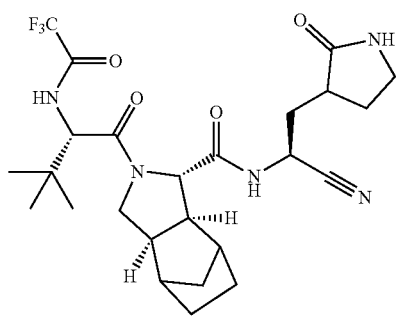
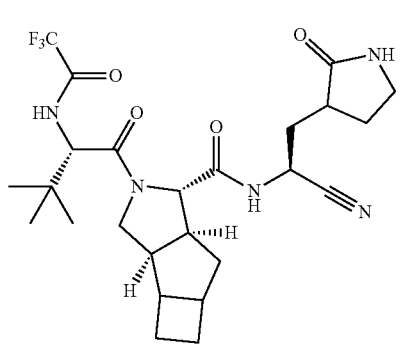
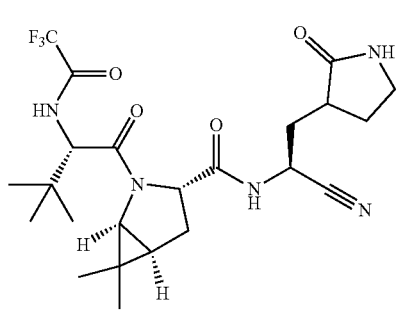 [SMILES: CC(C)(C)[C@H](NC(=O)C(F)(F)F)C(=O)N1[C@H]2[C@@H](C[C@H]1C(=O)N[C@H](C#N)CC1CCNC1=O)C2(C)C]
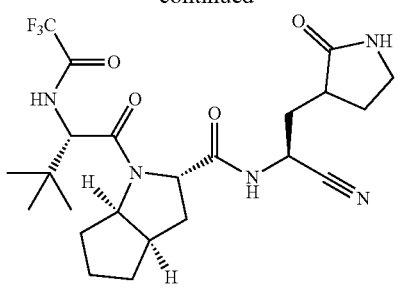
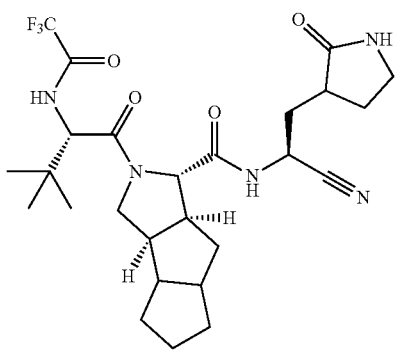
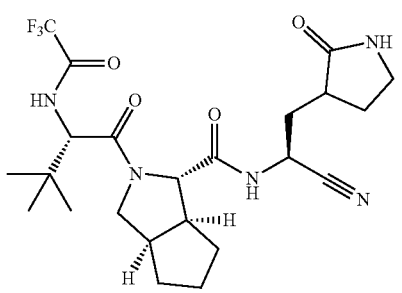
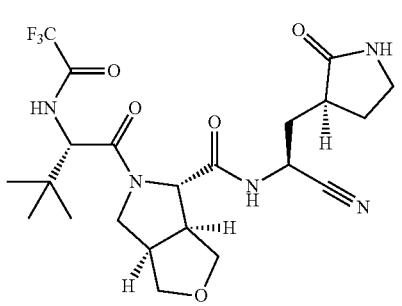
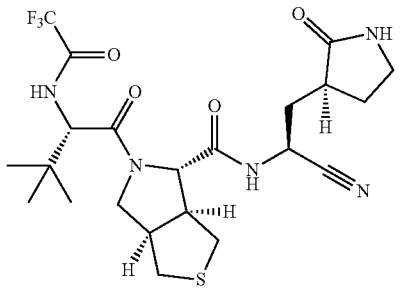

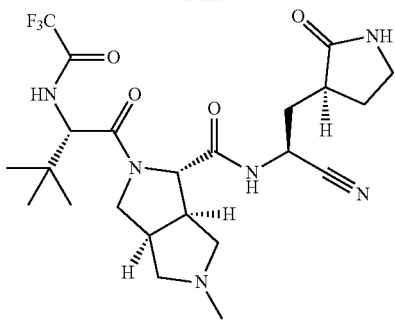

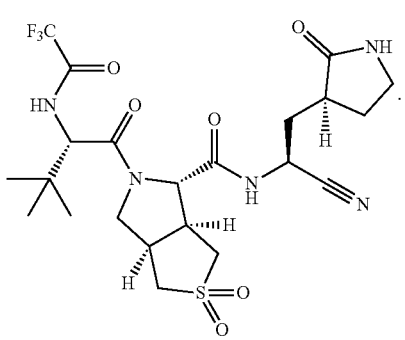

The present disclosure also provides a pharmaceutical composition, comprising the compound or the pharmaceutically acceptable salt thereof. Further, the pharmaceutical composition can also comprise a pharmaceutically acceptable excipient.

The present disclosure also provides a use of the compound or the pharmaceutically acceptable salt thereof, or the pharmaceutical composition in the manufacture of a medicament for the treatment of a disease related to 3CL protease.

In some embodiments of the present disclosure, the disease related to 3CL protease is coronavirus infection.

In some embodiments of the present disclosure, the coronavirus infection is infection with COVID-19.

The present disclosure also provides a method for treating coronavirus infection, comprising administering a therapeutically effective amount of the compound or the pharmaceutically acceptable salt thereof or the pharmaceutical composition to an individual in need thereof.

The present disclosure also provides the following synthetic routes:

Route 1

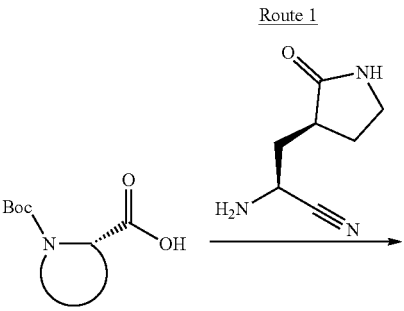

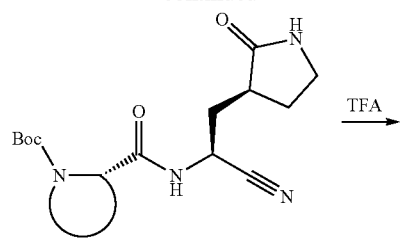

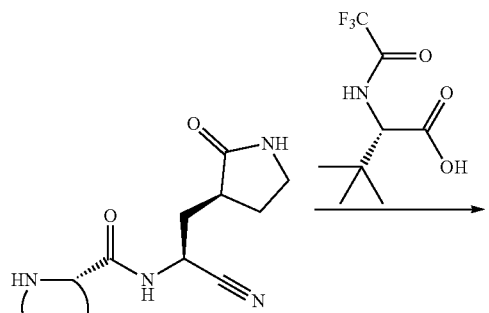

Route 2

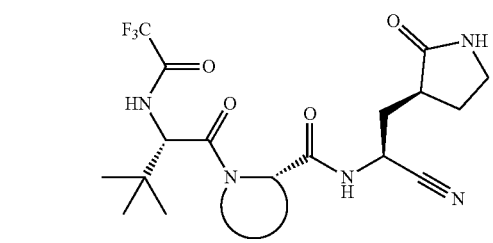

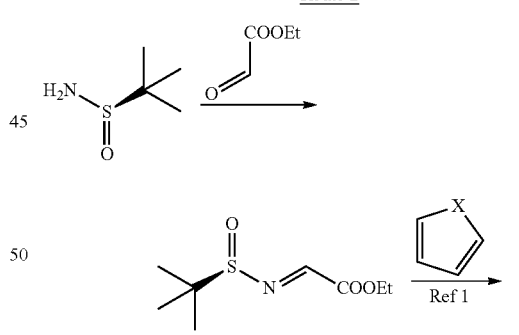

-continued
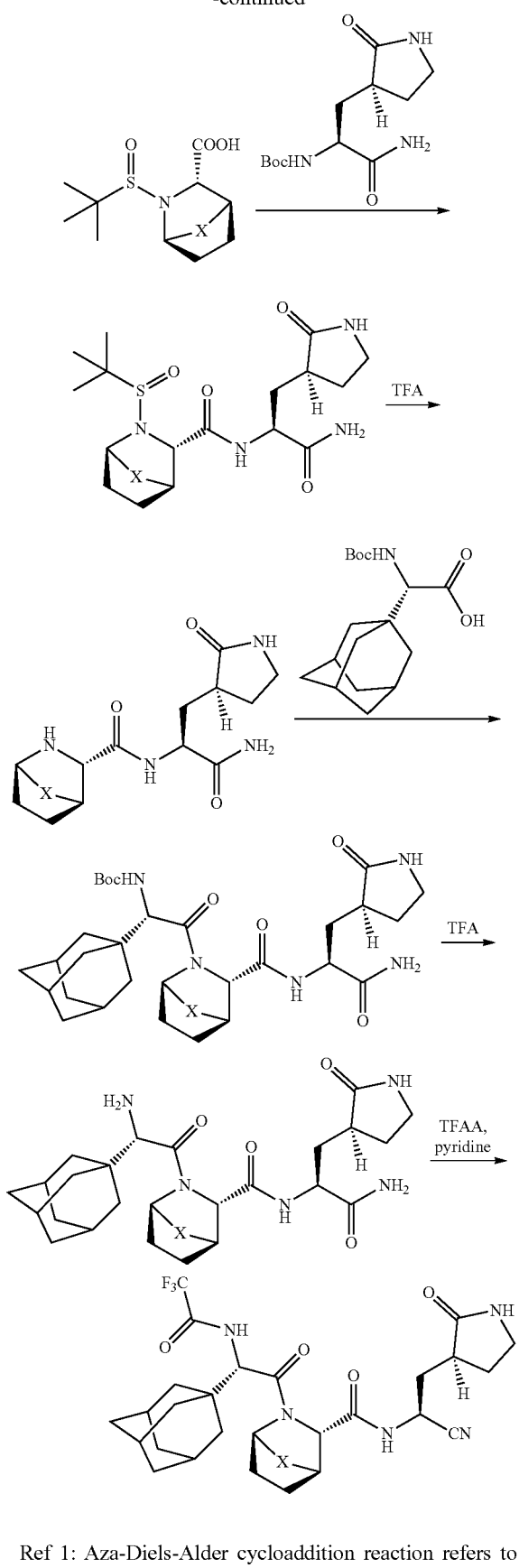
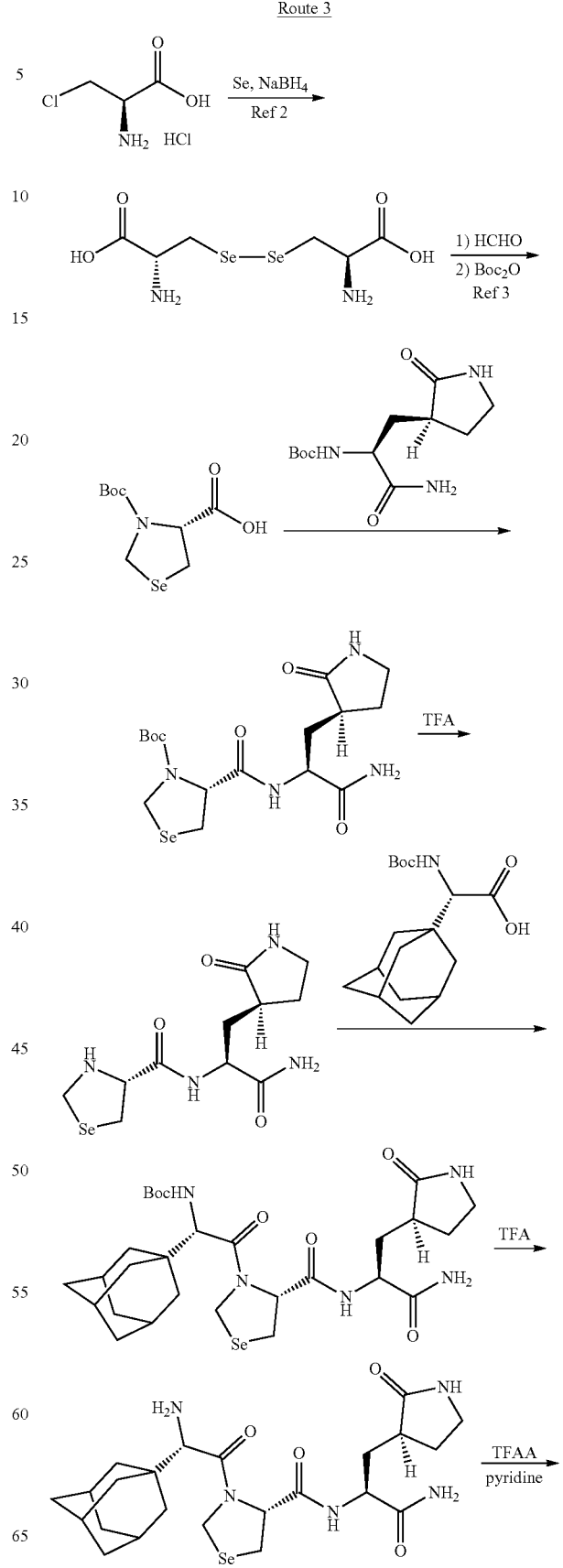
Ref 1: Aza-Diels-Alder cycloaddition reaction refers to the method in Tetrahedron, 2009, vol. 65, #14, p. 2806-2817.
Route 3

51

-continued

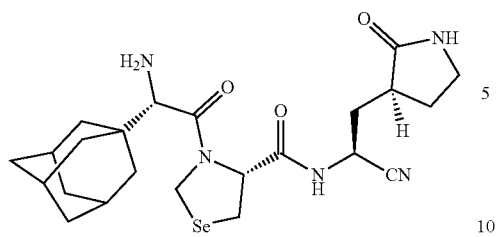

Ref 2: Bioorganic and Medicinal Chemistry Letters, 2001, vol. 11, #22, p. 2911-2915;
Ref 3: Organic Letters, 2020, vol. 22, #17, p. 6863-6867.

Route 4

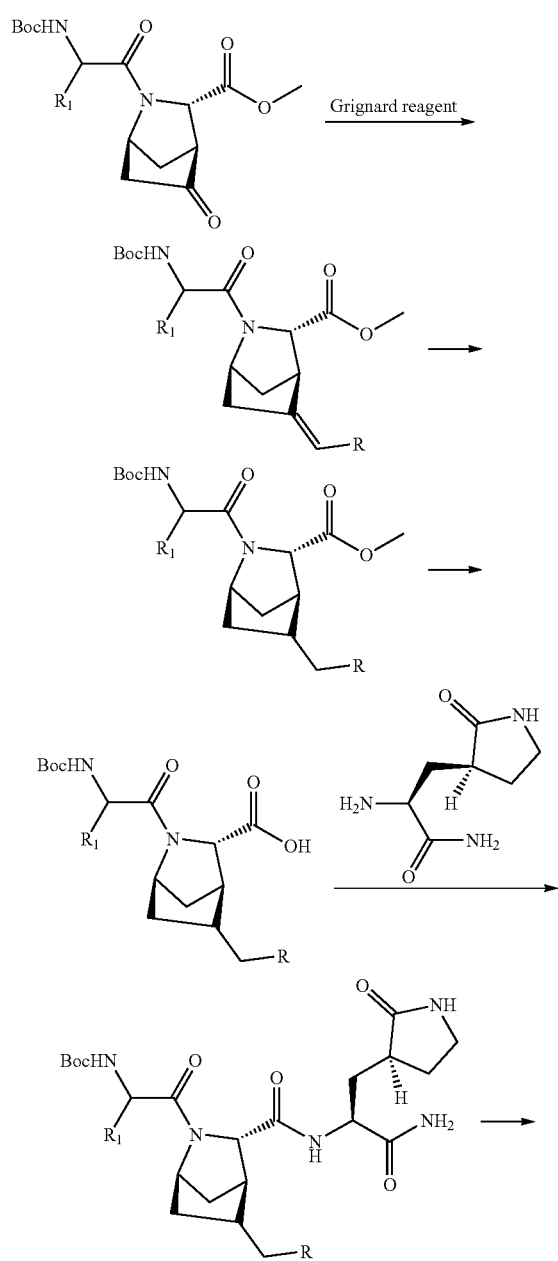

52

-continued

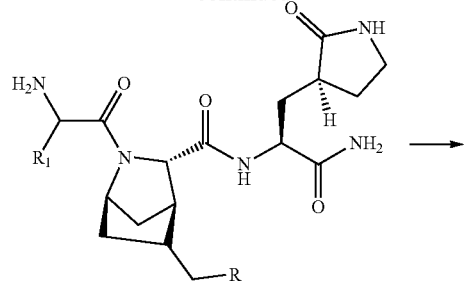

The present disclosure also provides the following test method:

1. Evaluation of the Antiviral Activity and Cytotoxicity Test of Compounds In Vitro by Novel Coronavirus Replicon System The compound is double diluted, and 0.3 μL per well is added to a 384 microwell cell plate. SARS-CoV-2 replicon RNA is electroporated into Huh7 cells, and then 60 μL of the mixture was inoculated into the microwell cell plate containing double diluted compound at a density of 4000/well. At the same time, ZPE control (cells electroporated with SARS-CoV-2 replicon without compound treatment) and HPE control (culture medium control) are set, and the final concentration of DMSO in the culture medium is 0.5%, and the cells are cultured in a 5% $CO_2$ and 37° C. incubator for 1 day. The number of cells expressing GFP in each well is detected by Acumen instrument, and the data are used for antiviral activity analysis. The conditions of cytotoxicity experiment are the same as those of antiviral experiment. After the compound is incubated with cells for 1 day, CellTiter Glo, a cell viability detection reagent, is added in the dark, and the cell viability of each well is detected by BioTek microplate reader, and the data are used for the cytotoxicity analysis of the sample. The antiviral activity and cell viability of the samples are analyzed by nonlinear fitting with GraphPad Prism software, and the half effective concentration ($EC_{50}$) and half cytotoxic concentration ($CC_{50}$) of the samples are calculated.

2. In Vitro Anti-Novel Coronavirus Activity and Toxicity Test

Nuclear viruses are obtained from African green monkey kidney (Vero) cells from the American Type Culture Collection (ATCC), Cat. No. CCL-81. Cells are cultured in Dulbecco's Modified Eagle's Medium (DMEM, WelGene) supplemented with 10% fetal bovine serum (Gibco) and 1% double antibody (Gibco). DMEM medium supplemented with 2% fetal bovine serum (Gibco) and 1% double antibody (Gibco) is used as the experimental culture medium.

Novel coronavirus βCoV/KOR/KCDC03/2020 strain is provided by Korea Centers for Disease Control and Prevention (KCDC), Serial No. NCCP43326.

Cell Plating

After the Vero cells are digested by trypsin, the Vero cells are diluted to 480,000 cells per mL with experimental culture medium. The diluted cells are added to a 384-well cell test plate with 25 μL and 12,000 cells per well using an automatic liquid separator. Cells are cultured overnight in a 5% $CO_2$ and 37° C. incubator.

Compound Treatment and Viral Infection

On the second day, the compound and CP-100356 are diluted with DMSO, and the diluted compound is added to the test cell wells using a liquid workstation. Then, 25 μL of SARS-CoV-2 virus diluted with the experimental culture medium is added to each well, with MOI=0.0125. Cell control (cells without compound treatment or virus infection) and no compound treatment control (cell infected with virus without compound treatment with 0.5% DMSO), and CP-100356 control (cell infected with virus, treated with 2 μM CP-100356) are set. The final volume of cell culture medium in each well is 50 μL. Cells are cultured in a 5% $CO_2$ and 37° C. incubator for 24 hours.

Immunofluorescence Staining
  (1) After 24 hours of virus infection, 17 μL of 16% paraformaldehyde is added to each well. Then the virus is left at room temperature for 30 minutes;
  (2) the supernatant is aspirated and the plate is washed twice with DPBS;
  (3) 25 μL of 0.25% Tritonx-100 is added to each well and left at room temperature for 20 minutes;
  (4) 0.25% TritonX-100 is aspirated, and DPBS is used to wash the plate twice;
  (5) 25 μL of diluted primary antibody (1:3000-fold diluted) is added to each well and incubated at 37° C. for 1 hour;
  (6) the primary antibody is aspirated and DPBS is used to wash the plate twice;
  (7) 25 μL of diluted secondary antibody Alexa Fluor 488-labeled sheep anti-rabbit IgG (1:2000-fold dilution) and 2.5 μg/mL (1:4000-fold dilution) of Hoechst 33342 are added to each well and incubated for 1 hour at 37° C.;
  (8) the secondary antibody and Hoechst are aspirated, and the plate is washed twice with DPBS;
  (9) high-content imaging analyzer Operetta is used to read the plate, and the instrument is set as: 488/405 emission, 20× objective, 5 fields of view per well.

3. Data Analysis:

Columbus software is used to quantitatively analyze the total number of cells (the number of cells stained by Hoechst) and the number of cells infected by the new coronavirus (the number of cells labeled with Alexa Fluor 488) in the images read by the high-content imaging analyzer. The ratio of infected cells and the total number of cells are used to analyze the antiviral activity and cytotoxicity of the compounds. The calculation formula is as follows:

Inhibition rate (%)=100−(ratio of infected cells in test wells−average ratio of infected cells in cell control wells)/(average ratio of infected cells in control wells without compound treatment−average ratio of infected cells in cell control wells)×100

Cell viability (%)=total number of cells in test wells/average total number of cells in control wells without compound treatment×100

XLfit 4 software is used for nonlinear fitting analysis of the inhibitory activity and cell viability of the compounds, and the $IC_{50}$ and $CC_{50}$ values of the compounds are calculated. The fitting method is "Sigmoidal dose-response". The calculation formula of $IC_{50}$ and $CC_{50}$ is: Y=Bottom+(Top Bottom)/(1+($IC_{50}$/X)Hillslope).

3. Pharmacokinetic Study In Vitro 3.1 Study on Hepatocyte Metabolic Stability (HMS)

1 μM compound is mixed with hepatocytes of CD-1 mice, SD rats, beagle dogs, cynomolgus monkeys and human at 37° C. and incubated at different time points (generally up to 90 min), and 7-ethoxycoumarin (7-EC, 30 μM) is used as a positive control to evaluate phase I and phase II metabolic activity in the hepatocyte incubation system. The incubation solution is removed at each time point, and the reaction is terminated by precipitating the protein with the organic phase. The supernatant is taken and LC/MS-MS is used to detect the remaining amount of the compound at each time point.

3.2 Study on Liver Microsomes Stability (MMS)

The test compounds are incubated with liver microsomes of CD-1 mice, SD rats, beagle dogs, cynomolgus monkeys and human to evaluate the stability of the compounds. The tested compounds are diluted to a sample with a concentration of 10 μM, pre-incubated with microsomes of five species for 10 minutes, and then the working solution of NADPH regeneration system is added to the incubation plate at each time point to start the reaction. Finally, at 0, 5, 10, 20, 30 and 60 minutes, the stop solution is added to the reaction plate to stop the reaction. The test compounds and control compounds are determined by LC-MS/MS method.

3.3 Study on Plasma Protein Binding Rate (PPB)

The protein binding rates of the test compounds in the plasma of CD-1 mice, Sprague-Dawley rats, beagle dogs, cynomolgus monkeys and human are determined by equilibrium dialysis method. Method: Plasma samples with the concentrations of 0.2, 2 and 25 μM are prepared from the plasma of the above five species, and placed in a 96-well balanced dialysis device, and dialyzed with phosphate buffered saline at 37±1° C. for 4 hours. Warfarin is used as the control compound in this experiment. The concentrations of test and control compounds in the samples are determined by liquid chromatography-tandem mass spectrometry (LC/MS/MS). The retention time of analyte and internal standard, chromatogram collection and chromatogram integration are processed by Analyst software (ABSCIEX, Framingham, Massachusetts, USA).

3.4. Study on CYP Enzyme Inhibition (Drug-Drug Interaction)

Pooled human liver microsomes (HLM) is used as CYP enzyme source, and probe substrates of five CYP isoenzymes are incubated with different concentrations of test compounds in the presence of cofactor NADPH, and the concentrations of metabolites of probe substrates in the incubation system are determined. According to the finally obtained dose-response curve, the IC50 values of the tested compounds for the specific probe substrate reaction catalyzed by CYP isoenzymes are calculated.

4. Study on Physicochemical Properties
4.1 Study on Membrane Permeability

The membrane permeability of the tested compounds is evaluated on MDR1-MDCK II cells. Test compounds are diluted in transport buffer to a sample with a final concentration of 2 μM and administered in both directions (A-B and B-A). After administration, the cell plates are incubated at 37° C. in an incubator containing 5% $CO_2$ and saturated humidity for 150 minutes. After the 150-minute incubation, samples are collected, and LC/MS/MS method is used to semi-quantitatively detect the concentrations of the test compounds and control compounds in the transport samples.

4.2 Study on Solubility

Kinetic solubility (KS) is measured by shake flask method

Kinetic solubility is the maximum concentration achieved by a compound after equilibration in buffer under DMSO solubilization conditions. Kinetic solubility of shake flask method is determined by high performance liquid chromatography-ultraviolet spectrophotometry. The concentration of the stock solution of the compound whose kinetic solubility is to be measured is 10 mM dimethyl sulfoxide solution, and the sample solution with 2% dimethyl sulfoxide content is obtained by diluting with buffer, and the theoretical concentration is 200 μM. The mixture is shaken at room temperature for 24 hours to reach an equilibrium state, and the equilibrium solution is filtered through a suction filter plate. The filtrate is analyzed by high performance liquid chromatography to obtain the ultraviolet absorption peak area, and the results are calculated by external standard method combined with dilution factor.

5. Study on Pharmacokinetics (PK) In Vivo

A pharmacokinetic study is performed using mice, rats, beagle dogs or cynomolgus monkeys. For PK study of single compound administration, the test compound is administered by single intravenous injection or intragastric administration according to a certain dose. For cassette-PK, the test compound is administered by intravenous injection or intragastric administration in a certain dose according to a single compound. Plasma is collected before administration (0) and 0.083, 0.25, 0.5, 1, 2, 4, 6, 8, 12 and 24 hours after administration (sampling time points or adjust according to the properties of each compound). The plasma concentration is processed using the non-compartmental model of the pharmacokinetic software, and the pharmacokinetic parameters are calculated using the linear logarithmic trapezoidal method.

6. OC43 In Vivo Efficacy:

The model of coronavirus (COV) infection in mice (10 days old) is used to evaluate the antiviral efficacy of the test compounds in vivo by observing the survival rate. Specific process: Mice are inoculated with virus by nasal drip, and the test compound is administered continuously for 7 days from day 0 to day 6 by intraperitoneal injection once a day, and the first administration time is 2 hours before virus inoculation. Animals are observed continuously from day 0 to day 14, and their weight, health and survival are recorded.

Technical Effect

The compounds of the present disclosure have good in vitro anti-novel coronavirus Mpro protease activity; good in vitro anti-coronavirus activity at the cellular level, and have no cytotoxicity; and have good pharmacokinetic properties. After the compound of the present disclosure is used in combination with Ritonavir, the exposure is nearly 20 times higher than that of a single drug, and there is a higher exposure in the lung of rats.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt may be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt may be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The "pharmaceutically acceptable excipient" refer to inert substances which are administered together with the active ingredient and are beneficial to the administration of the active ingredient, including but not limited to any glidant, sweetener, diluent, preservative, dye/colorant, flavor enhancer, surfactant, wetting agent, dispersant, disintegrant, suspending agent and stabilizer which are acceptable for human or animals (such as livestock) and licensed by the State Food and Drug Administration.

As used herein and as familiar in the art, "treatment" or "treating" is a method for obtaining beneficial or desired results, including clinical results. Beneficial or desired clinical results may include, but are not limited to: reduction in tumor progression, reduction in tumor size, reduction in tumor growth rate, reduction in tumor invasion and metastatic potential, alleviation or amelioration of one or more symptoms or conditions, reduction in disease degree, stable (i.e., not worsening) disease state, prevention of disease spread, delay or slowing of disease progression, amelioration or palliation of disease state, and remission (whether partial or total), whether detectable or undetectable. "Treatment" or "treating" can also mean prolonging survival as compared to expected survival if not receiving treatment.

The term "pharmaceutical composition" refers to a mixture of one or more compounds of the present disclosure or the salts thereof and a pharmaceutically acceptable excipient. The purpose of the pharmaceutical composition is to facilitate administration of the compound of the present disclosure to an organism.

The therapeutic dose of the compound of the present disclosure can be determined according to, for example, the specific use of the treatment, the mode of administration of the compound, the health and state of the patient, and the judgment of the prescribing physician. The ratio or concentration of the compounds of the present disclosure in the pharmaceutical composition may not be fixed, depending on various factors, including dose, chemical properties (e.g., hydrophobicity) and route of administration.

The term "treatment" means administering a compound or formulation described herein to ameliorate or eliminate a disease or one or more symptoms related to the disease, and includes:
  (i) inhibition of a disease or disease state, that is, arrest of its development;
  (ii) alleviation of a disease or disease state, even if the disease or disease state subsides.

The term "therapeutically effective amount" means an amount of the compound of the present disclosure that (i) treats a particular disease, condition or disorder, (ii) alleviates, ameliorates, or eliminates one or more symptoms of the particular disease, condition or disorder, or (iii) prevents or delays the onset of one or more symptoms of the particular disease, condition, or disorder described herein. The amount of the compound of the present disclosure that constitutes a "therapeutically effective amount" varies depending on the compound, the disease state and its severity, the mode of administration, and the age of the mammal to be treated, but can be routinely determined by those skilled in the art according to their own knowledge and the present disclosure.

Unless otherwise required in the present disclosure, throughout the specification and the following claims, the word "comprise" and variations thereof such as "comprises" and "comprising" should be interpreted in an open and inclusive sense, that is, "include, but not limited to".

References throughout this specification to "in some embodiments" or "in an embodiment" or "in another embodiment" or "in certain embodiments" means that specific reference elements, structures or features related to the embodiment is included in at least one embodiment. Thus, appearances of the phrases "in some embodiments" or "in an embodiment" or "in another embodiment" or "in certain embodiments" in various places throughout the specification are not necessarily all referring to the same embodiment.

Furthermore, specific elements, structures or features may be combined in one or more embodiments in any suitable manner.

Unless otherwise specified, the term "isomer" is intended to include geometric isomers, cis-trans isomers, stereoisomers, enantiomers, optical isomers, diastereomers and tautomers.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemization.

Unless otherwise specified, the absolute configuration of a stereogenic center is represented by a wedged solid bond (◂) and a wedged dashed bond (◂), and the relative configuration of a stereogenic center is represented by a straight solid bond (◂) and a straight dashed bond (◂), a wave line (◂) is used to represent a wedged solid bond (◂) or a wedged dashed bond (◂), or the wave line (◂) is used to represent a straight solid bond (◂) or a straight dashed bond (◂).

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

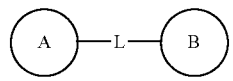

is -M-W-, then -M-W- can link ring A and ring B to form

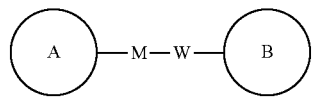

in the direction same as left-to-right reading order, and form

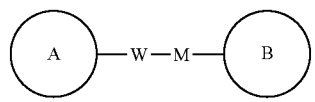

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond ( ⁄ ), a straight dashed bond ( ⁄⁻⁻ ) or a wavy line ( ⁓ ). For example, the straight solid bond in —OCH$_3$ means that it is linked to other groups through the oxygen atom in the group; the straight dashed bonds in

means that it is linked to other groups through the two ends of nitrogen atom in the group; the wave lines in

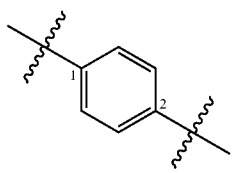 [SMILES: *c1ccc(*)cc1]

means that the phenyl group is linked to other groups through carbon atoms at position 1 and position 2.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl) and the like.

Unless otherwise specified, the term "$C_{1-3}$ haloalkyl" refers to monohaloalkyl and polyhaloalkyl containing 1 to 3 carbon atoms. The $C_{1-3}$ haloalkyl includes $C_{1-2}$, $C_{2-3}$, $C_3$, $C_2$ and $C_1$ haloalkyl and the like. Examples of $C_{1-3}$ haloalkyl include, but are not limited to, trifluoromethyl, trichloromethyl, 2,2,2-trifluoroethyl, pentafluoroethyl, pentachloroethyl, 3-bromopropyl and the like.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, the term "$C_{1-3}$ haloalkoxy" refers to monohaloalkoxy and polyhaloalkoxy containing 1 to 3 carbon atoms. The $C_{1-3}$ haloalkoxy includes $C_{1-2}$, $C_{2-3}$, $C_3$, $C_2$ and $C_1$ haloalkoxy and the like. Examples of $C_{1-3}$ haloalkoxy include, but are not limited to, trifluoromethoxy, trichloromethoxy, 2,2,2-trifluoroethoxy, pentafluoroethoxy, pentachloroethoxy, 3-bromopropoxy and the like.

Unless otherwise specified, the number of atoms in a ring is usually defined as the number of ring members, for example, "5- to 7-membered ring" refers to a "ring" in which 5-7 atoms are arranged around.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$ and the like; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring and the like.

Unless otherwise specified, "$C_{3-10}$ cycloalkyl" refers to a saturated cyclic hydrocarbon group consisting of 3 to 10 carbon atoms, including monocyclic, bicyclic and tricyclic systems, wherein the bicyclic and tricyclic systems include spiro ring, fused ring and bridged ring. The $C_{3-10}$ cycloalkyl includes $C_{3-8}$, $C_{3-6}$, $C_{3-5}$, $C_{4-10}$, $C_{4-8}$, $C_{4-6}$, $C_{4-5}$, $C_{5-8}$ or $C_{5-6}$ cycloalkyl and the like; it can be monovalent, divalent or multivalent. Examples of $C_{3-10}$ cycloalkyl include, but are not limited to, cyclopropyl, cyclobutyl, cyclopentyl, cyclohexyl, cycloheptyl, norbornanyl, [2.2.2]dicyclooctyl and the like.

Unless otherwise specified, "$C_{5-8}$ cycloalkyl" refers to a saturated cyclic hydrocarbon group consisting of 5 to 8 carbon atoms, including monocyclic and bicyclic systems, wherein the bicyclic systems include spiro ring, fused ring and bridged ring. The $C_{5-8}$ cycloalkyl includes $C_{5-6}$, $C_{4-6}$, $C_{5-8}$, $C_{6-8}$ cycloalkyl and the like. It can be monovalent, divalent or multivalent. Examples of $C_{5-8}$ cycloalkyl include, but are not limited to, cyclopentyl, cyclohexyl, cycloheptyl, norbornanyl, [2.2.2]dicyclooctyl and the like.

Unless otherwise specified, "$C_{4-8}$ cycloalkyl" refers to a saturated cyclic hydrocarbon group consisting of 4 to 8 carbon atoms, including monocyclic and bicyclic systems, wherein the bicyclic systems include spiro ring, fused ring and bridged ring. The $C_{4-8}$ cycloalkyl includes $C_{4-7}$, $C_{4-6}$, $C_{4-5}$, $C_{5-8}$ or $C_{5-6}$ cycloalkyl and the like. It can be monovalent, divalent or multivalent. Examples of $C_{4-8}$ cycloalkyl include, but are not limited to, cyclobutyl, cyclopentyl, cyclohexyl, cycloheptyl, norbornanyl, [2.2.2]dicyclooctyl and the like.

Unless otherwise specified, "$C_{3-6}$ cycloalkyl" refers to a saturated cyclic hydrocarbon group consisting of 3 to 6 carbon atoms, which is a monocyclic and bicyclic system, and the $C_{3-6}$ cycloalkyl includes $C_{3-5}$, $C_{4-5}$ and $C_{5-6}$ cycloalkyl and the like; it can be monovalent, divalent or multivalent. Examples of $C_{3-6}$ cycloalkyl include, but are not limited to, cyclopropyl, cyclobutyl, cyclopentyl, cyclohexyl and the like.

Unless otherwise specified, "$C_{5-8}$ cycloalkenyl" refers to a partially unsaturated cyclic hydrocarbon group consisting of 5 to 8 carbon atoms containing at least one carbon-carbon double bond, including monocyclic and bicyclic systems, wherein the bicyclic systems include spiro ring, fused ring and bridged ring and any ring in this system is non-aromatic. The $C_{5-8}$ cycloalkenyl includes $C_{5-6}$, $C_{5-7}$, $C_{6-8}$ or $C_{7-8}$ cycloalkenyl and the like. It can be monovalent, divalent or multivalent. Examples of $C_{5-8}$ cycloalkenyl include, but are not limited to, cyclopentenyl, cyclopentadienyl, cyclohexenyl, cyclohexadienyl and the like.

Unless otherwise specified, the term "3- to 10-membered heterocycloalkyl" by itself or in combination with other terms refers to a saturated cyclic group consisting of 3 to 10 ring atoms, wherein 1, 2, 3 or 4 ring atoms are heteroatoms independently selected from O, S and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic, bicyclic and tricyclic systems, wherein the bicyclic and tricyclic systems include spiro ring, fused ring and bridged ring. In addition, with regard to the "3- to 10-membered heterocycloalkyl", a heteroatom may occupy the connection position of the heterocycloalkyl with the rest of the molecule. The 3- to 10-membered heterocycloalkyl includes 3- to 8-membered, 3- to 6-membered, 3- to 5-membered, 4- to 6-membered, 5- to 6-membered, 4-membered, 5-membered, and 6-membered heterocycloalkyl and the like. Examples of 3- to 10-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxinyl, dithianyl, isoxazolidinyl, isothiazolidinyl, 1,2-oxazinyl, 1,2-thiazinyl, hexahydropyridazinyl, homopiperazinyl, homopiperidinyl or dioxacycloheptyl and the like.

Unless otherwise specified, the term "3- to 8-membered heterocycloalkyl" by itself or in combination with other terms refers to a saturated cyclic group consisting of 3 to 8 ring atoms, wherein 1, 2, 3 or 4 ring atoms are heteroatoms independently selected from O, S and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic and bicyclic systems, wherein the bicyclic systems include spiro ring, fused ring and bridged ring. In addition, with regard to the "3- to 8-membered heterocycloalkyl", a heteroatom may occupy the connection position of the heterocycloalkyl with the rest of the molecule. The 3- to 8-membered heterocycloalkyl includes 3- to 6-membered, 3- to 5-membered, 4- to 6-membered, 5- to 6-membered, 4-membered, 5-membered and 6-membered heterocycloalkyl and the like. Examples of 3- to 8-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxinyl, dithianyl, isoxazolidinyl, isothiazolidinyl, 1,2-oxazinyl, 1,2-thiazinyl, hexahydropyridazinyl, homopiperazinyl, homopiperidinyl or dioxacycloheptyl and the like.

Unless otherwise specified, the term "5- to 8-membered heterocycloalkyl" by itself or in combination with other terms refers to a saturated cyclic group consisting of 5 to 8 ring atoms, wherein 1, 2, 3 or 4 ring atoms are heteroatoms independently selected from O, S and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic and bicyclic systems, wherein the bicyclic systems include spiro ring, fused ring and bridged ring. In addition, with regard to the "5- to 8-membered heterocycloalkyl", a heteroatom may occupy the connection position of the heterocycloalkyl with the rest of the molecule. The 5- to 8-membered heterocycloalkyl includes 5- to 6-membered, 5- to 7-membered, 6- to 8-membered and 7- to 8-membered heterocycloalkyl and the like. Examples of 5- to 8-membered heterocycloalkyl include, but are not limited to, pyrrolidinyl, pyrazolidinyl, imidazolidinyl, tetrahydrothienyl (including tetrahydrothiophen-2-yl and tetrahydrothiophen-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxinyl, dithianyl, isoxazolidinyl, isothiazolidinyl, 1,2-oxazinyl, 1,2-thiazinyl, hexahydropyridazinyl, homopiperazinyl, homopiperidinyl or dioxacycloheptyl and the like.

Unless otherwise specified, the term "5- to 6-membered heterocycloalkyl" by itself or in combination with other terms refers to a saturated cyclic group consisting of 5 to 6 ring atoms, wherein 1, 2, 3 or 4 ring atoms are heteroatoms independently selected from O, S, N, P and Se, and the rest are carbon atoms, wherein nitrogen atoms are optionally quaternized, and nitrogen, sulfur and phosphorous heteroatoms can be optionally oxidized (i.e., NO, $S(O)_p$ and $P(O)_p$, p is 1 or 2). It includes monocyclic and bicyclic systems, wherein the bicyclic systems include spiro ring, fused ring and bridged ring. In addition, with regard to the "5- to 6-membered heterocycloalkyl", a heteroatom may occupy the connection position of the heterocycloalkyl with the rest of the molecule. The 5- to 6-membered heterocycloalkyl includes 5-membered, and 6-membered heterocycloalkyl and the like. Examples of 5- to 6-membered heterocycloalkyl include, but are not limited to, pyrrolidinyl, pyrazolidinyl, imidazolidinyl, tetrahydrothienyl (including tetrahydrothiophen-2-yl and tetrahydrothiophen-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxinyl, dithianyl, isoxazolidinyl, isothiazolidinyl, 1,2-oxazinyl, 1,2-thiazinyl or hexahydropyridazinyl and the like.

Unless otherwise specified, the term "5- to 8-membered heterocycloalkenyl" by itself or in combination with other terms respectively means a partially unsaturated cyclic group consisting of 5 to 8 ring atoms containing at least one carbon-carbon double bond, wherein 1, 2, 3 or 4 ring atoms are heteroatoms independently selected from O, S and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic, bicyclic and tricyclic systems, wherein the bicyclic and tricyclic systems include spiro ring, fused ring and bridged ring, and any ring in systems is non-aromatic. In addition, with regard to the "5- to 8-membered heterocycloalkenyl", a heteroatom may occupy the connection position of the heterocycloalkenyl with the rest of the molecule. The 5- to 8-membered heterocycloalkenyl includes 5- to 7-membered, 5- to 6-membered, 4- to 5-membered, 4-membered, 5-membered and 6-membered heterocycloalkenyl and the like. Examples of 5- to 8-membered heterocycloalkenyl include, but are not limited to,

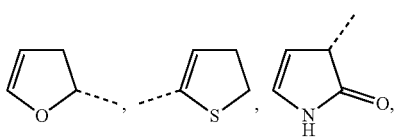

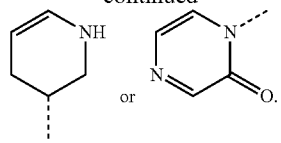

Unless otherwise specified, the term "5- to 6-membered heterocycloalkenyl" by itself or in combination with other terms refers to a partially unsaturated cyclic group consisting of 5 to 6 ring atoms, wherein 1, 2, 3 or 4 ring atoms are heteroatoms independently selected from O, S, N, P or Se, and the rest are carbon atoms, wherein nitrogen atoms are optionally quaternized, and nitrogen, sulfur and phosphorus heteroatoms can be optionally oxidized (i.e., NO, $S(O)_p$ and $P(O)_p$, p is 1 or 2). It includes monocyclic and bicyclic systems, wherein the bicyclic systems include spiro ring, fused ring and bridged ring, and any ring in this system is non-aromatic. In addition, with regard to the "5- to 6-membered heterocycloalkenyl", a heteroatom may occupy the connection position of the heterocycloalkenyl with the rest of the molecule. The 5- to 6-membered heterocycloalkenyl includes 5-membered and 6-membered heterocycloalkenyl and the like. Examples of 5- to 6-membered heterocycloalkenyl include, but are not limited to,

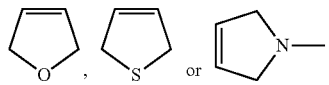

and the like.

Unless otherwise specified, the terms "$C_{6-10}$ aromatic ring" and "$C_{6-10}$ aryl" in the present disclosure can be used interchangeably, and the term "$C_{6-10}$ aromatic ring" or "$C_{6-10}$ aryl" means a cyclic hydrocarbon group with a conjugated π electron system consisting of 6 to 10 carbon atoms, which can be a monocyclic, fused bicyclic or fused tricyclic system, wherein each ring is aromatic. It can be monovalent, divalent or multivalent, and $C_{6-10}$ aryl includes $C_{6-9}$, $C_9$, $C_{10}$ and $C_6$ aryl and the like. Examples of $C_{6-10}$ aryl include, but are not limited to, phenyl, naphthyl (including 1-naphthyl and 2-naphthyl and the like).

Unless otherwise specified, the terms "5- to 10-membered heteroaromatic ring" and "5- to 10-membered heteroaryl" can be used interchangeably in the present disclosure, and the term "5- to 10-membered heteroaryl" means a cyclic group with a conjugated π electron system consisting of 5 to 10 ring atoms, of which 1, 2, 3 or 4 ring atoms are heteroatoms independently selected from O, S, N, P or Se, and the rest are carbon atoms. It can be a monocyclic, fused bicyclic or fused tricyclic system, wherein each ring is aromatic. Where nitrogen atoms are optionally quaternized, and nitrogen, sulfur and phosphorus heteroatoms can be optionally oxidized (i.e., NO, $S(O)_p$ and $P(O)_p$, p is 1 or 2). The 5- to 10-membered heteroaryl can be attached to the rest of the molecule through a heteroatom or a carbon atom. The 5- to 10-membered heteroaryl includes 5- to 8-membered, 5- to 7-membered, 5- to 6-membered, 5-membered and 6-membered heteroaryl and the like. Examples of the 5- to 10-membered heteroaryl include, but are not limited to, pyrrolyl (including N-pyrrolyl, 2-pyrrolyl and 3-pyrrolyl and the like), pyrazolyl (including 2-pyrazolyl and 3-pyrazolyl and the like), imidazolyl (including N-imidazolyl, 2-imidazolyl, 4-imidazolyl and 5-imidazolyl and the like), oxazolyl (including 2-oxazolyl, 4-oxazolyl and 5-oxazolyl and the like), triazolyl (1H-1,2,3-triazolyl, 2H-1,2,3-triazolyl, 1H-1,2,4-triazolyl and 4H-1,2,4-triazolyl and the like), tetrazolyl, isoxazolyl (3-isoxazolyl, 4-isoxazolyl and 5-isoxazolyl and the like), thiazolyl (including 2-thiazolyl, 4-thiazolyl and 5-thiazolyl and the like), furyl (including 2-furyl and 3-furyl and the like), thienyl (including 2-thienyl and 3-thienyl and the like), pyridyl (including 2-pyridyl, 3-pyridyl and 4-pyridyl and the like), pyrazinyl, pyrimidinyl (including 2-pyrimidinyl and 4-pyrimidinyl and the like), benzothiazolyl (including 5-benzothiazolyl and the like), purinyl, benzimidazolyl (including 2-benzimidazolyl and the like), benzoxazolyl, indolyl (including 5-indolyl and the like), isoquinolyl (including 1-isoquinolyl and 5-isoquinolinyl and the like), quinoxalinyl (including 2-quinoxalinyl and 5-quinoxalinyl and the like) or quinolyl (including 3-quinolyl and 6-quinolyl and the like).

Unless otherwise specified, the term "halo" or "halogen" by itself or as apart of another substituent refers to fluorine, chlorine, bromine or iodine atom.

Optically active (R)- and (S)-isomers, or D and L isomers can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereoisomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the present disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvents used in the present disclosure are commercially available.

The following abbreviations are used in the present disclosure:

ACN stands for acetonitrile; Boc stands for tert-butoxycarbonyl; PE stands for petroleum ether; EA or EtOAc stands for ethyl acetate; Pre-HPLC stands for high performance liquid chromatography preparative column; ° C. stands for Celsius; DCM stands for dichloromethane; TEBBE reagent stands for a hydrocarbyl titanocene, bis(cyclopentadienyl)-g-chloro(dimethylaluminum)-g-methylenetitanium, CAS: 67719-69-1.

The compounds of the present disclosure are named according to the conventional naming principles in the art or by ChemDraw® software, and the commercially available compounds use the supplier catalog names.

DETAILED DESCRIPTION OF THE INVENTION

The present disclosure is described in detail by the embodiments below, but it does not mean that there are any adverse restrictions on the present disclosure. The present disclosure has been described in detail herein, and its specific embodiments have also been disclosed; for one skilled in the art, it is obvious to make various modifications and improvements to the embodiments of the present disclosure without departing from the spirit and scope of the present disclosure.

Calculation Embodiment 1
Simulation of the Binding Mode of Compounds 15 to 27 to Protein:
15
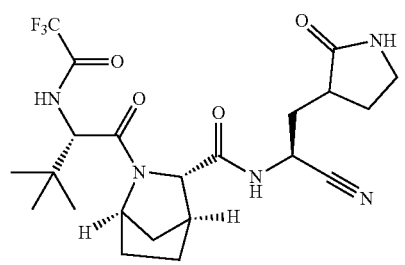
16
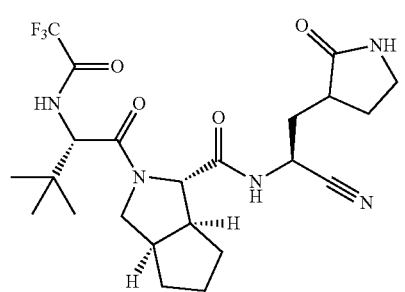
17
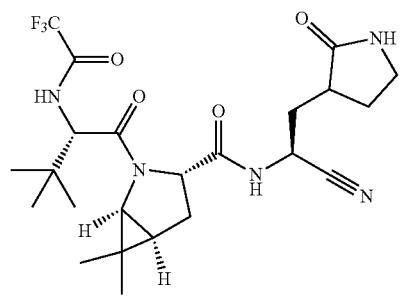
18
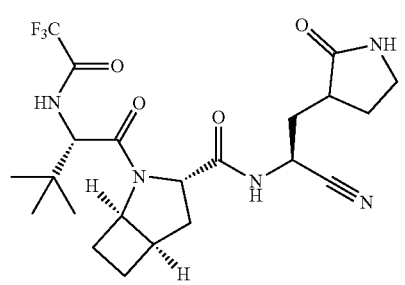
19
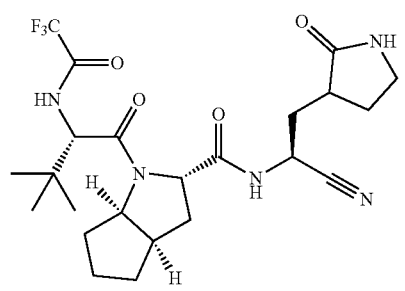
-continued
20
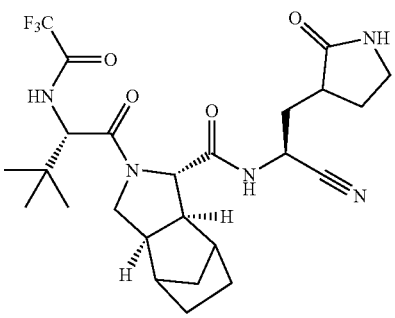
21
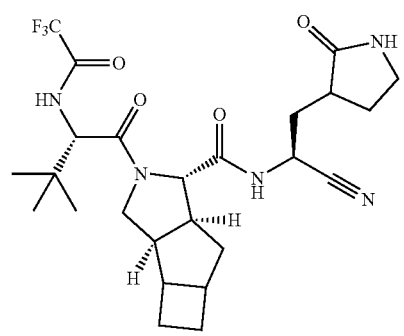
22
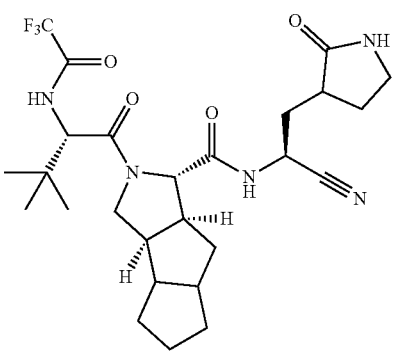
23
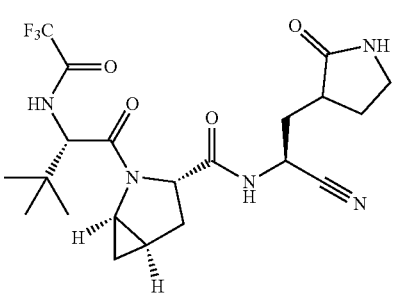
24
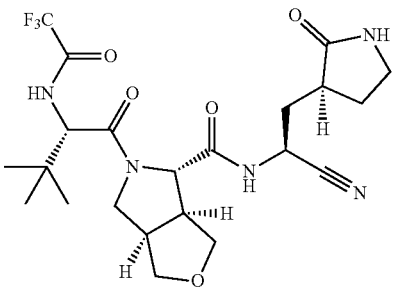

-continued

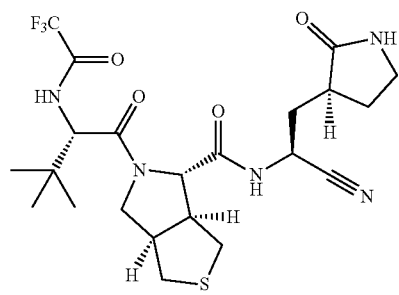

25

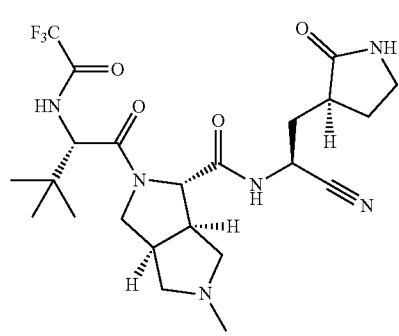

26

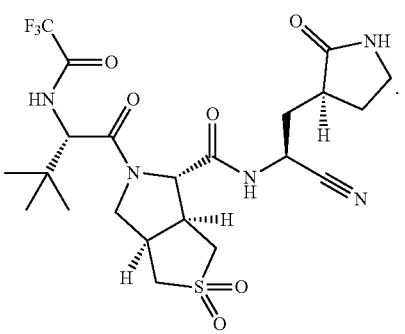

27

Figure 1:
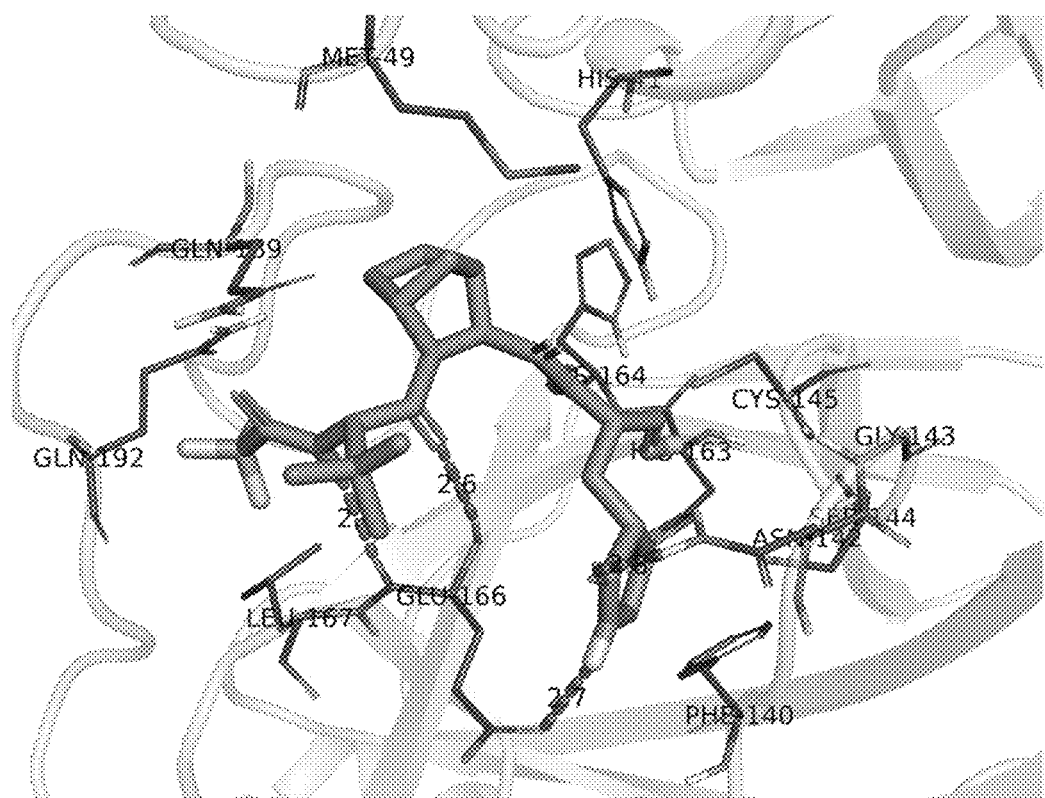
FIG. 1. The binding mode pattern of compound 15 and 6WTT protein.
Figure 2:
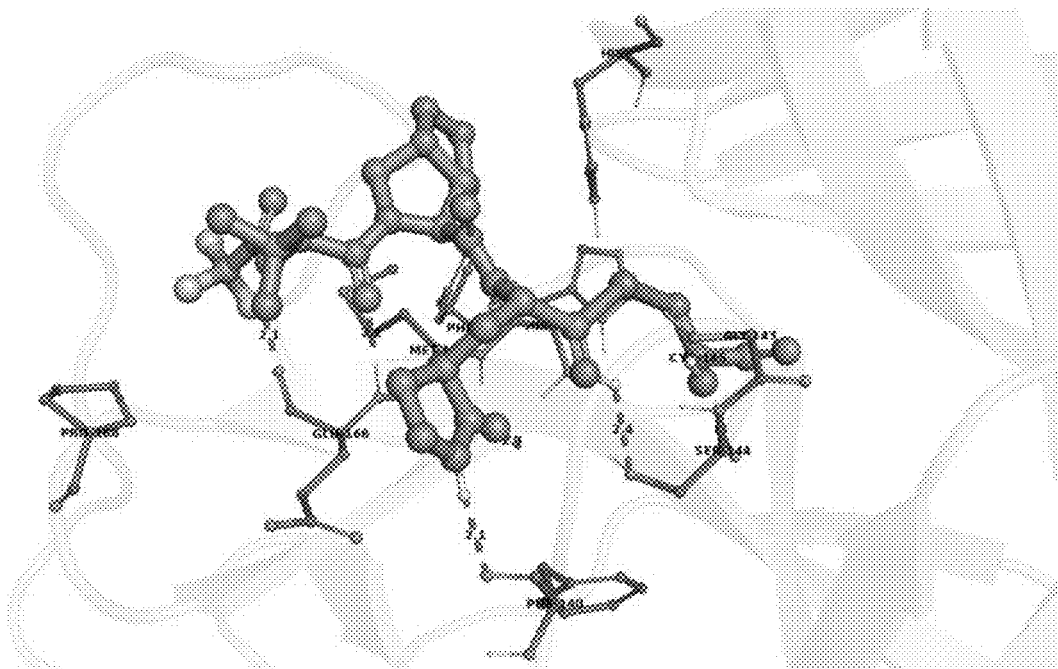
FIG. 2. the binding mode pattern of compound 16 and 6WTT protein.
Figure 3:
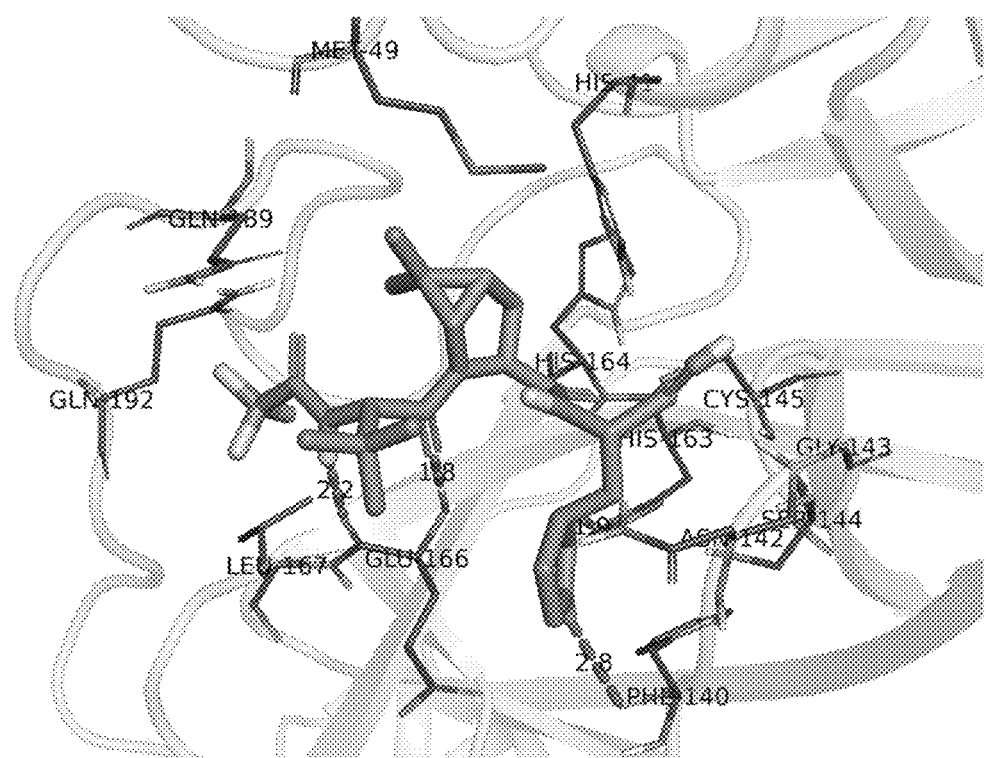
FIG. 3. the binding mode pattern of compound 17 and 6WTT protein.
Figure 4:
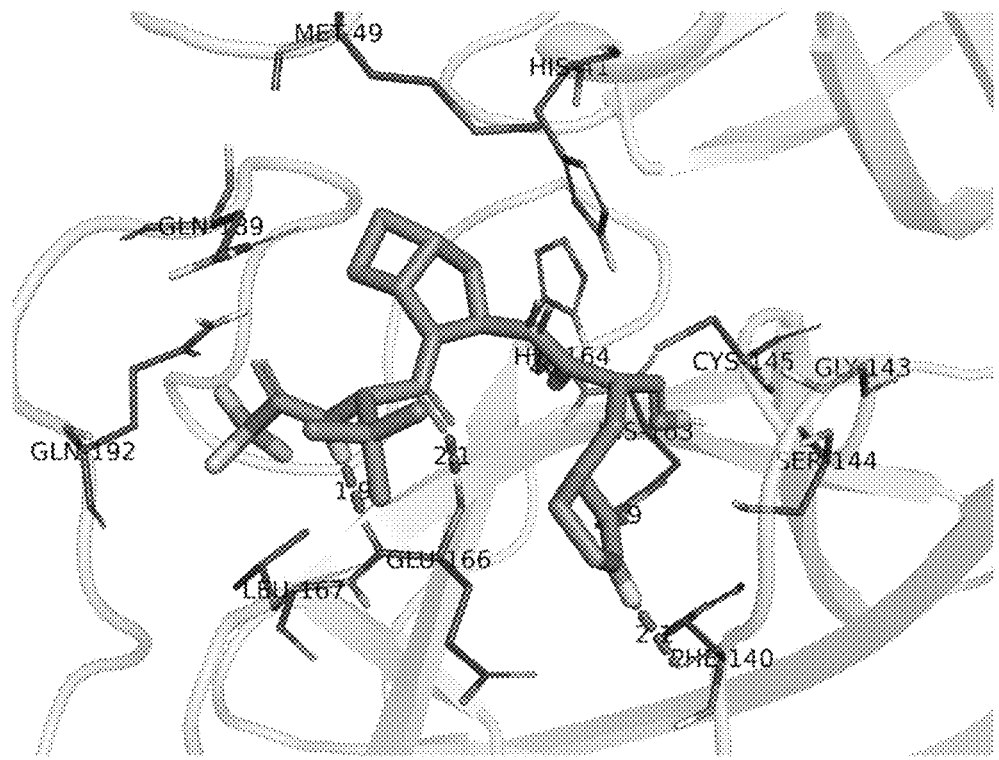
FIG. 4. the binding mode pattern of compound 18 and 6WTT protein.
Figure 5:
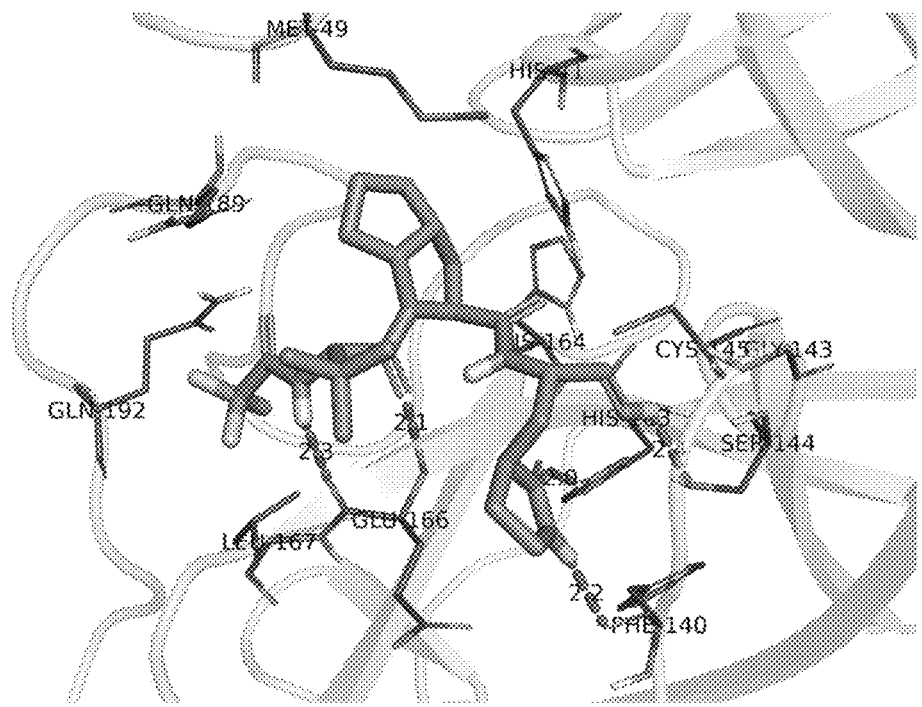
FIG. 5. the binding mode pattern of compound 19 and 6WTT protein.
Figure 6:
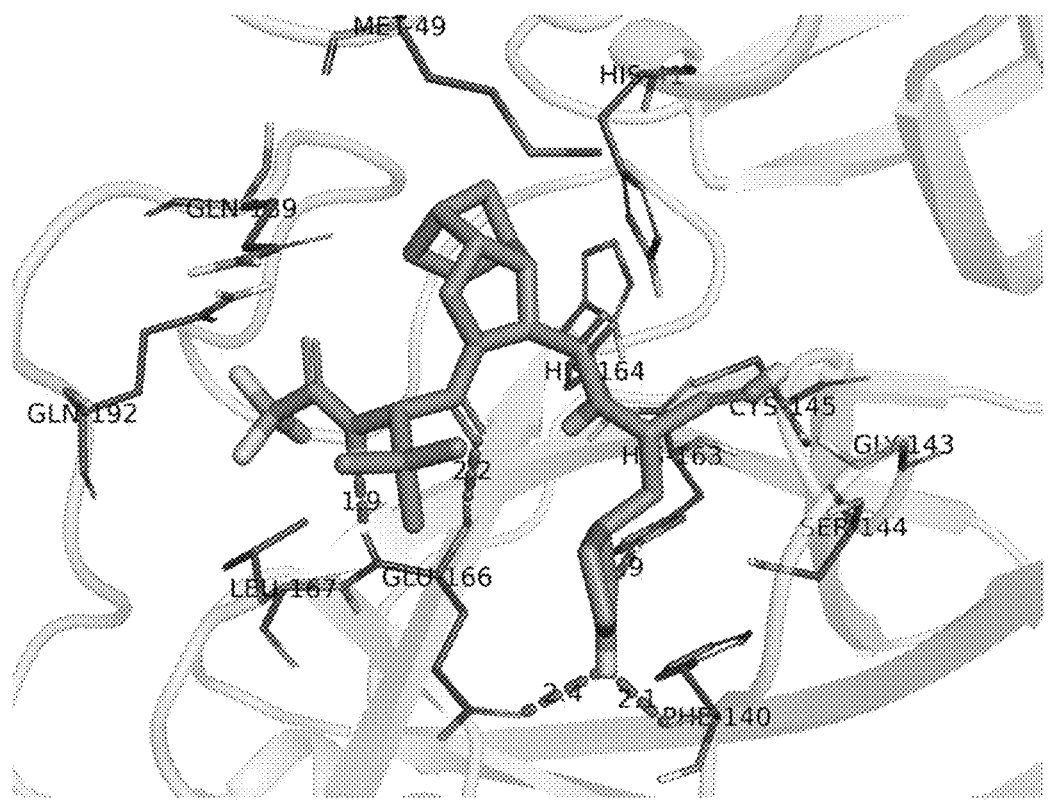
FIG. 6. the binding mode pattern of compound 20 and 6WTT protein.
Figure 7:
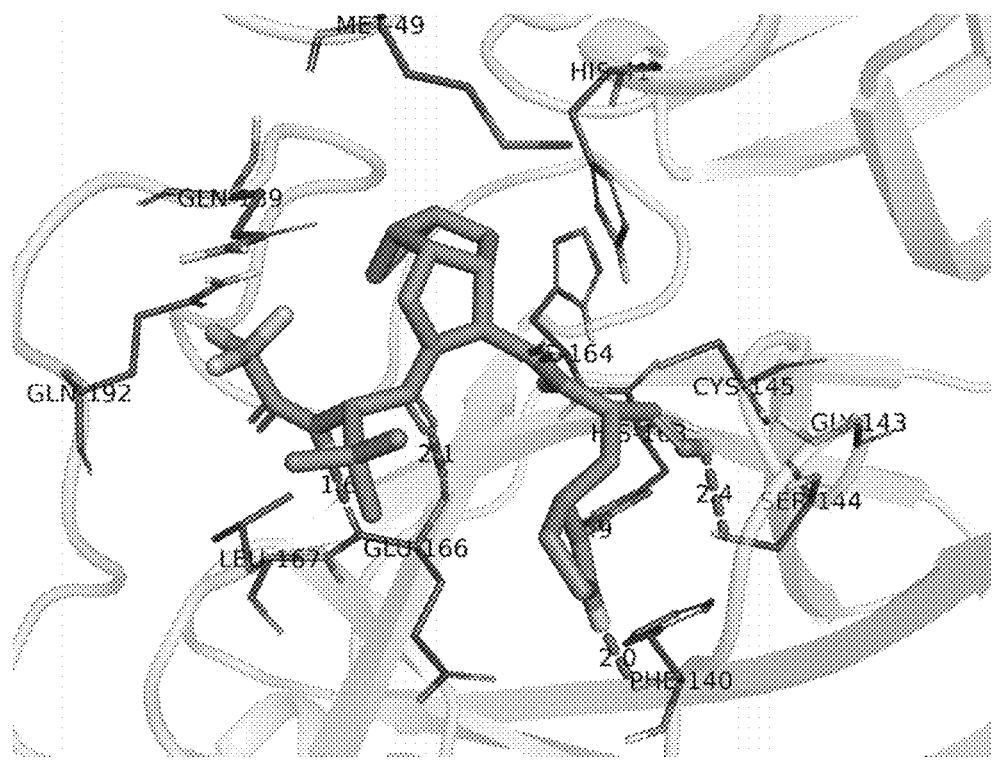
FIG. 7. the binding mode pattern of compound 21 and 6WTT protein.
Figure 8:
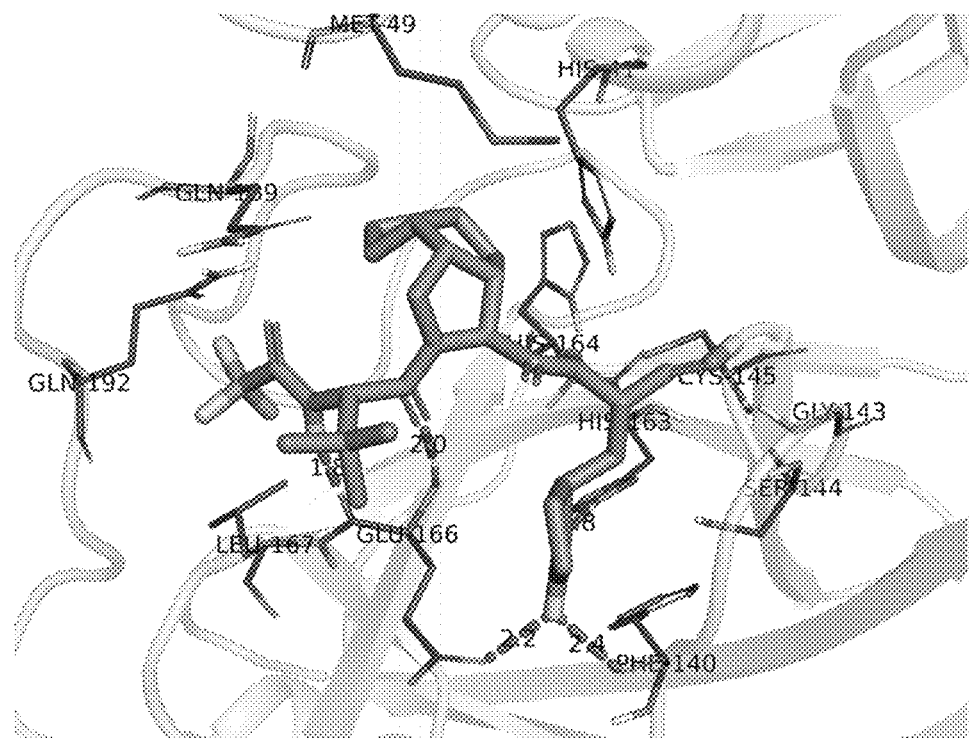
FIG. 8. the binding mode pattern of compound 22 and 6WTT protein.
Figure 9:
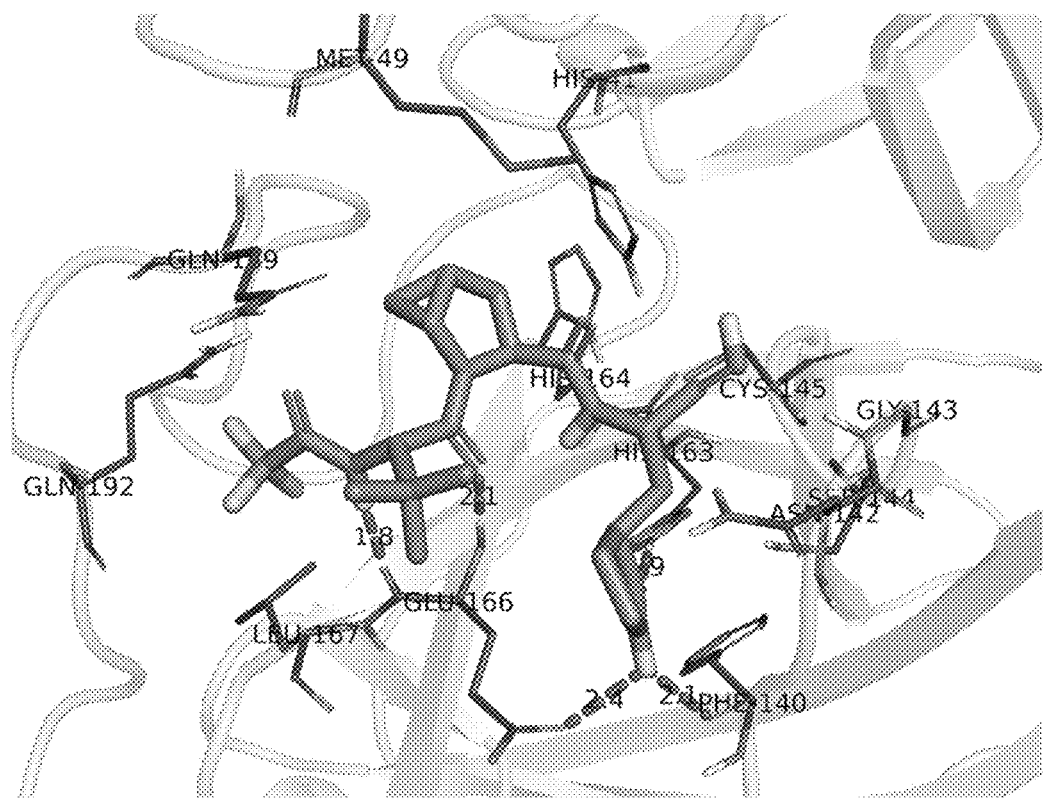
FIG. 9. the binding mode pattern of compound 23 and 6WTT protein.
Figure 10:
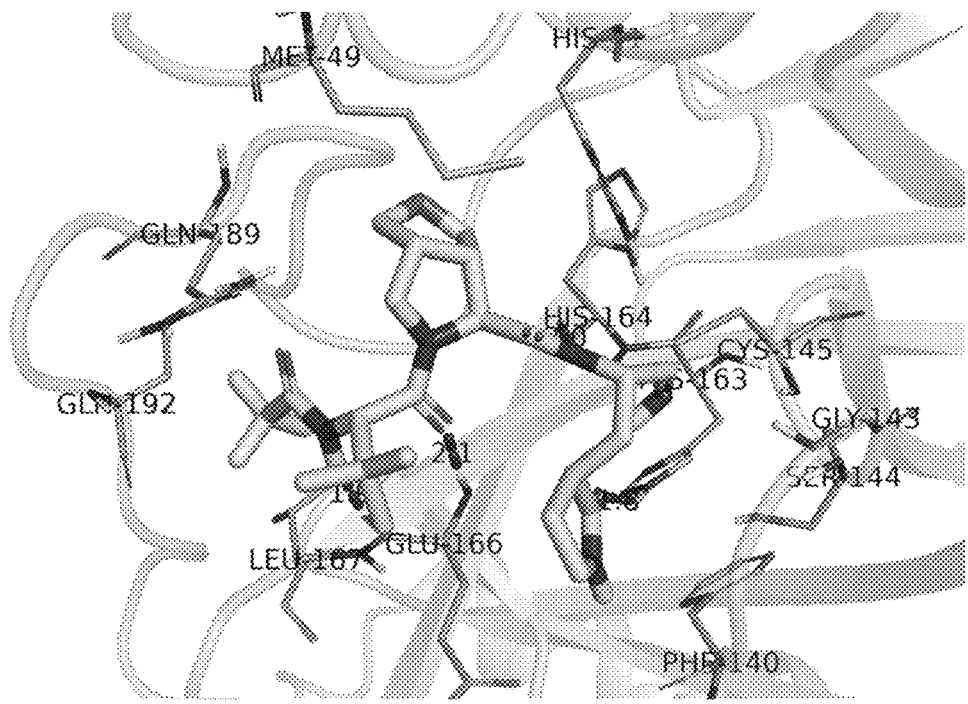
FIG. 10. the binding mode pattern of compound 24 and 6WTT protein.
Figure 11:
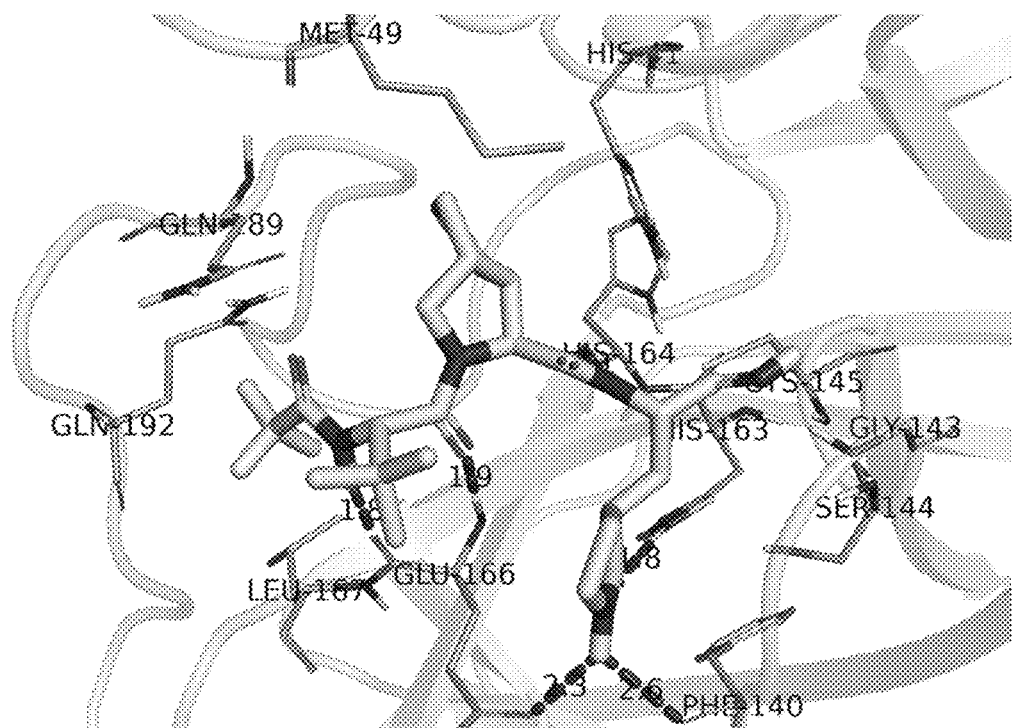
FIG. 11. the binding mode pattern of compound 25 and 6WTT protein.
Figure 12:
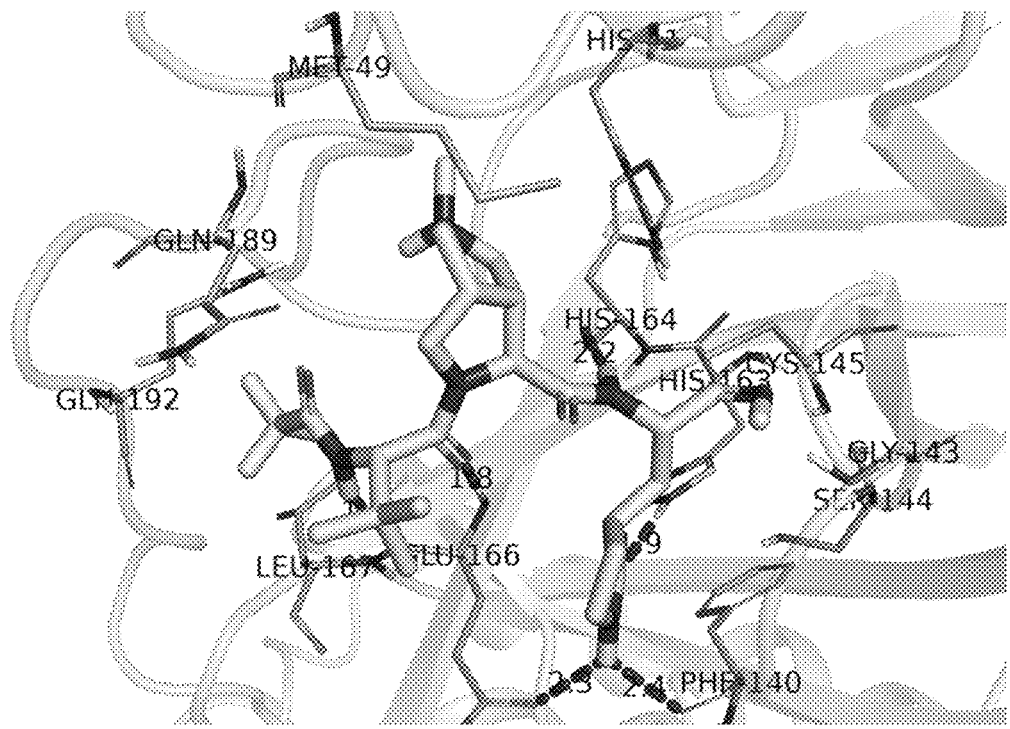
FIG. 12. the binding mode pattern of compound 26 and 6WTT protein.
Figure 13:
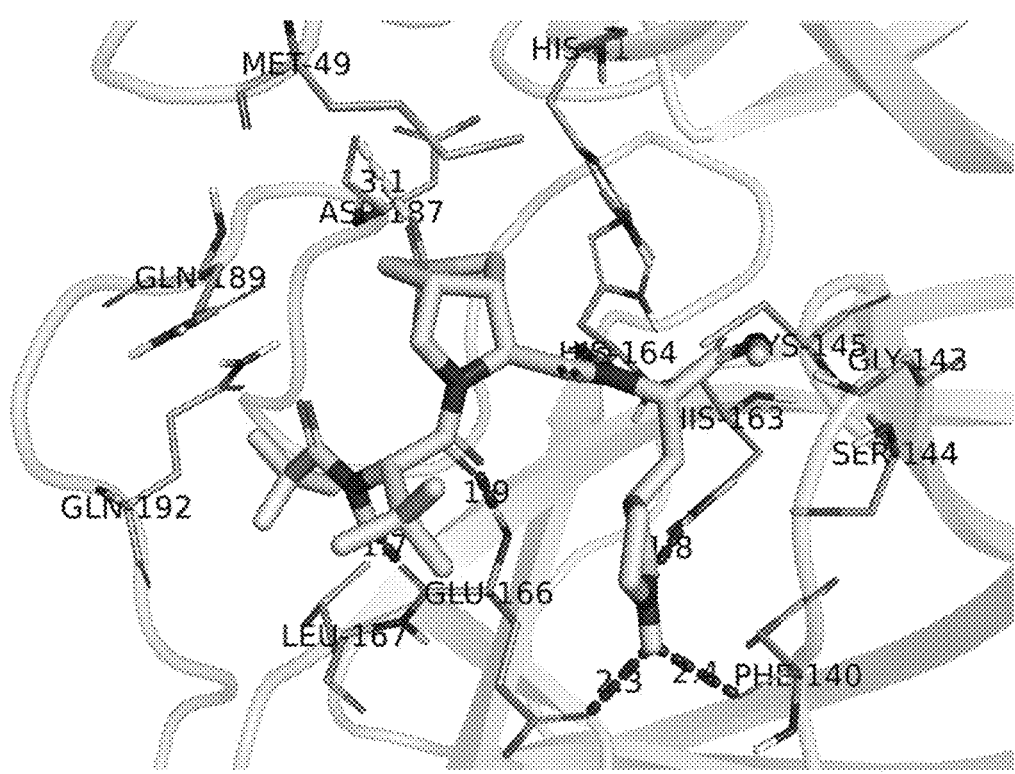
FIG. 13. the binding mode pattern of compound 27 and 6WTT protein.

The molecular docking process was carried out by using GlideSP[1] in Maestro (Schrödinger version 2017-2) and the default options. The cocrystal structure with the PDB ID code of 6WTT was selected as the docking template. For the preparation of protein, hydrogen atoms were added using the protein preparation wizard module of Maestro[2] and the OPLS3 force field was used. For the preparation of ligands, 3D structures were generated, and the energy minimization was performed by LigPrep[3]. A 30 Å docking grid was generated using the ligand centroids from the 7BV2 crystal structure. The ligands were then removed and embodiment compounds were placed during molecular docking. The type of interaction between protein receptor and ligand was analyzed, and then the reasonable docking conformation was selected and saved according to the calculated docking score and globalStrain values. The simulation results of compounds 15-27 binding to 6WTT protein are shown in FIGS. 1 to 13.

[1] Glide, Schrödinger, LLC, New York, NY, 2017.
[2] Maestro, Schrödinger, LLC, New York, NY, 2017.
[3] LigPrep, Schrödinger, LLC, New York, NY, 2017.

Conclusion: The compounds of the present disclosure have a good combination with 6WTT protein.

Embodiment 1

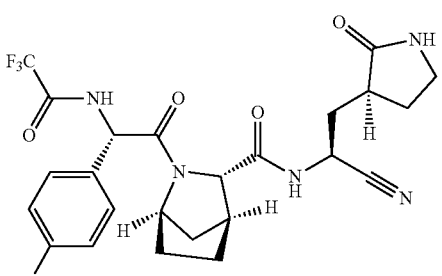

1

Synthetic route

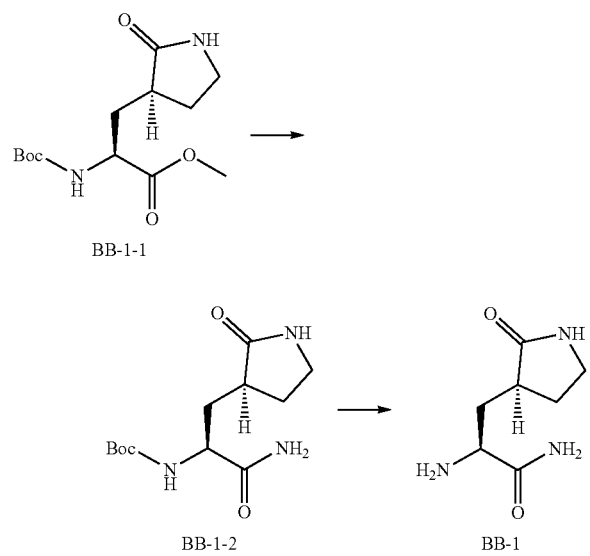

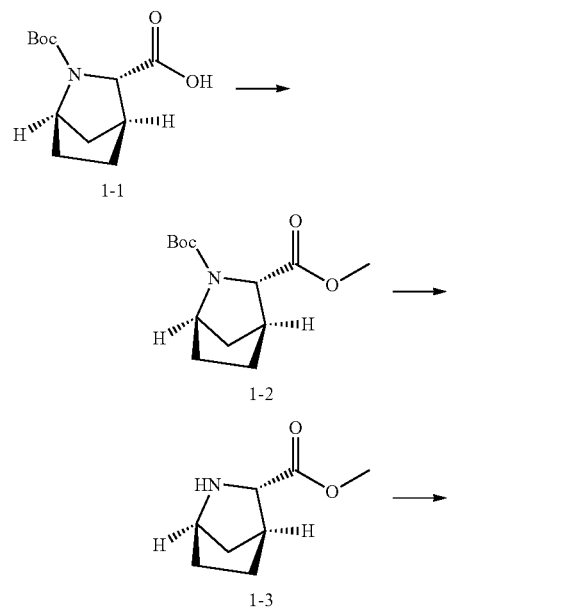

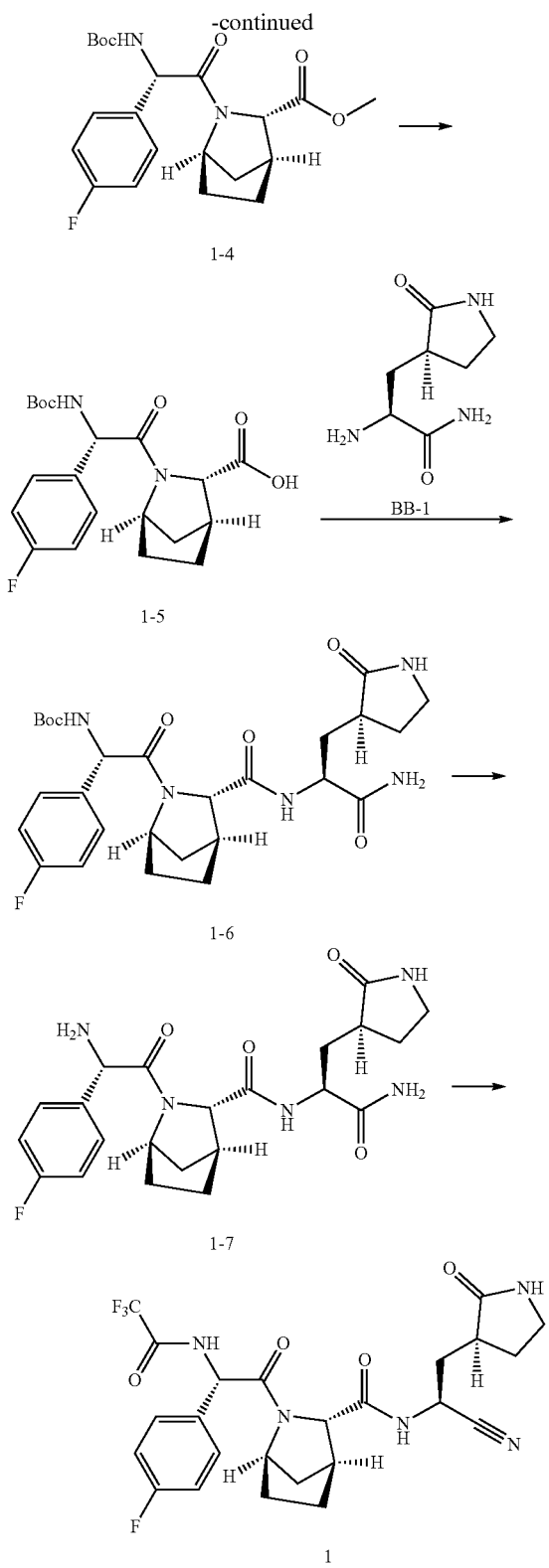

solved with an appropriate amount of DCM then concentrated again. The residue was not purified to obtain compound BB-1-2. $^1$H NMR (400 MHz, CDCl$_3$) δ=7.23-7.07 (m, 1H), 6.57-6.36 (m, 1H), 6.12-5.96 (m, 1H), 5.95-5.82 (m, 1H), 4.44-4.28 (m, 1H), 3.46-3.23 (m, 2H), 2.60-2.49 (m, 1H), 2.46-2.29 (m, 1H), 2.15-2.00 (m, 1H), 1.96-1.78 (m, 2H), 1.55-1.37 (m, 9H).

Step 2: Synthesis of Hydrochloride of Compound BB-1

Compound BB-1-2 (2 g, 7.37 mmol) was added to ethyl acetate (10 mL), and 4M ethyl acetate solution (20 mL) of hydrogen chloride was added thereto, and then the reaction was stirred continuously at 20° C. for 3 hours. The reaction mixture was filtered to obtain a white solid, which was quickly transferred to a flask (highly susceptible to moisture absorption), and concentrated under reduced pressure. Hydrochloride of compound BB-1 was obtained. $^1$H NMR (400 MHz, CD$_3$OD) δ=4.06-3.99 (m, 1H), 3.69-3.60 (m, 2H), 3.44-3.37 (m, 2H), 2.83-2.70 (m, 1H), 2.48-2.37 (m, 1H), 2.11-2.02 (m, 2H), 1.94-1.81 (m, 1H), 1.65-1.55 (m, 2H).

Step 3: Synthesis of Compound 1-2

At 0° C., toluene (4 mL), (trimethylsilyl)diazomethane (2 M, 1.66 mL) were added to a solution of compound 1-1 (400.00 mg, 1.66 mmol) in methanol (2 mL), and the reaction mixture was reacted at 20° C. for 16 hours. The reaction mixture was concentrated under reduced pressure to obtain a crude product. The crude product was separated by silica gel column chromatography (petroleum ether/ethyl acetate=10:1) to obtain compound 1-2. $^1$H NMR (400 MHz, CDCl$_3$) δ=4.39-4.20 (m, 1H), 3.87-3.68 (m, 4H), 2.74-2.62 (m, 1H), 1.98-1.87 (m, 1H), 1.83-1.61 (m, 3H), 1.56-1.49 (m, 1H), 1.48-1.36 (m, 9H), 1.30-1.21 (m, 1H).

Step 4: Synthesis of Hydrochloride of Compound 1-3

Ethyl acetate hydrochloride (4 M, 5 mL) was added to a reaction flask with compound 1-2 (0.28 g, 1.10 mmol) and the reaction mixture was reacted at 20° C. for 2 hours. The reaction mixture was concentrated under reduced pressure to obtain a crude product. Hydrochloride of compound 1-3 was obtained. $^1$H NMR (400 MHz, CD$_3$OD) δ=4.21-4.07 (m, 2H), 3.94-3.79 (m, 3H), 3.03-2.91 (m, 1H), 2.04-2.03 (m, 1H), 2.05-2.00 (m, 1H), 1.93-1.80 (m, 3H), 1.73 (s, 2H).

Step 5: Synthesis of Compound 1-4

At 0° C., (S)-2-((tert-butoxycarbonyl)amino)-2-(4-fluorophenyl)acetic acid (0.5 g, 1.86 mmol), N,N-diisopropylethylamine (719.95 μmg, 5.57 μmmol) and 2-(7-azabenzotriazol-1-yl)-N,N,N,N-tetramethyluronium hexafluorophosphate (1.06 g, 2.79 mmol) were added to a solution of hydrochloride of compound 1-3 (427.06 mg, 2.23 mmol) in N,N-dimethylformamide (5 mL), and the reaction mixture was reacted at 20° C. for 16 hours. The reaction mixture was poured into 5% citric acid solution to separate the phases, then the aqueous phase was extracted with ethyl acetate (50 mL×2), and the organic phase was dried over anhydrous sodium sulfate, filtered, and concentrated under reduced pressure to obtain a crude product. The crude product was separated by silica gel column chromatography (petroleum ether/ethyl acetate=3:1) to obtain compound 1-4. $^1$H NMR (400 MHz, CDCl$_3$) δ=7.60-7.33 (m, 2H), 7.16-6.93 (m, 2H), 5.77 (br d, J=7.9 Hz, 1H), 5.50-5.36 (m, 1H), 3.87-3.68 (m, 3H), 2.81-2.59 (m, 1H), 1.88-1.68 (m, 3H), 1.60 (s, 1H), 1.48-1.39 (m, 9H), 1.34-1.19 (m, 4H).

Step 6: Synthesis of Compound 1-5

Lithium hydroxide monohydrate (148.66 mg, 3.54 mmol) was added to a solution of compound 1-4 (0.72 g, 1.77 mmol) in tetrahydrofuran (10 mL) and water (5 mL), and the reaction mixture was reacted at 20° C. for 16 hours. The reaction mixture was added with 50 mL of 5% citric acid aqueous solution, and 50 mL of ethyl acetate was added to separate the phases, then the organic phase was dried over anhydrous sodium sulfate, filtered and concentrated under reduced pressure to obtain a crude product. Compound 1-5 was obtained. $^1$H NMR (400 MHz, CDCl$_3$) δ=7.52-7.34 (m, 2H), 7.13-7.01 (m, 2H), 5.99 (br d, J=7.3 Hz, 1H), 5.55-5.36 (m, 1H), 4.45-4.18 (m, 1H), 4.08-3.98 (m, 1H), 3.06-2.87 (m, 1H), 2.01-1.72 (m, 3H), 1.69-1.52 (m, 1H), 1.47-1.37 (m, 10H), 1.27 (br t, J=7.1 Hz, 1H).

Step 7: Synthesis of Compound 1-6

At 0° C., hydrochloride of compound BB-1 (412.75 mg, 1.99 mmol), N,N-diisopropylethylamine (642.23 mg, 4.97 mmol, 865.54 μL), 1-hydroxybenzotriazole (268.58 mg, 1.99 mmol) and hydrochloride of 1-(3-dimethylaminopropyl)-3-acetaldehyde (381.04 mg, 1.99 mmol) were added to a solution of compound 1-5 (0.65 g, 1.66 mmol) in butanone (10 mL), and the reaction mixture was reacted at 20° C. for 16 hours. The reaction mixture was poured into 20 mL of water, and a mixed solution of dichloromethane and methanol (volume ratio of 5:1) (50 mL×2) was added for extraction, and the organic phase was washed with 5% citric acid solution (50 mL×1) and washed with water (50 mL×1), then the organic phase was dried over anhydrous sodium sulfate, filtered, and concentrated under reduced pressure to obtain a crude product. The crude product was separated by silica gel column chromatography (dichloromethane/methanol=15:1) to obtain compound 1-6. $^1$H NMR (400 MHz, DMSO-d$_6$) δ=8.52-7.98 (m, 1H), 7.71-7.58 (m, 1H), 7.54-7.39 (m, 2H), 7.29-7.08 (m, 3H), 7.03 (br s, 1H), 5.46 (br d, J=8.5 Hz, 1H), 4.50-4.18 (m, 1H), 4.13 (br s, 1H), 3.51 (br s, 1H), 3.15-3.05 (m, 1H), 2.61-2.46 (m, 5H), 2.37-1.84 (m, 3H), 1.82-1.49 (m, 5H), 1.45-1.28 (m, 9H), 1.25-1.16 (m, 1H).

Step 8: Synthesis of Trifluoroacetate of Compound 1-7

At 0° C., trifluoroacetic acid (1 mL) was added to a solution of compound 1-6 (0.3 g, 515.41 μmol) in dichloromethane (3 mL), and the reaction mixture was reacted at 20° C. for 2 hours. The reaction mixture was concentrated under reduced pressure to obtain a crude product. Trifluoroacetate of compound 1-7 was obtained.

Step 9: Synthesis of Compound 1

At 0° C., pyridine (492.38 mg, 6.22 mmol, 502.43 μL) and trifluoroacetic anhydride (272.37 mg, 1.30 mmol, 180.38 μL) were added to a solution of trifluoroacetate of compound 1-7 (0.25 g, 518.73 μmol) in tetrahydrofuran (2 mL), and the reaction mixture was reacted at 20° C. for 2 hours. The reaction mixture was quenched with 20 mL of water, and ethyl acetate (20 mL×2) was added for extraction, then the organic phase was washed with 5% citric acid (20 mL×1), dried over anhydrous sodium sulfate, filtered and concentrated under reduced pressure to obtain a crude product. The crude product was separated by preparative HPLC (column type: Phenomenex C18 75*30 mm*3 μm; mobile phase: [H$_2$O (NH$_4$HCO$_3$)-ACN]; ACN %: 20%-60%, 8 min) to obtain compound 1. $^1$H NMR (400 MHz, DMSO-d$_6$) δ=9.42-9.07 (m, 1H), 8.33-7.97 (m, 1H), 6.97-6.83 (m, 1H), 6.78-6.61 (m, 2H), 6.46-6.34 (m, 2H), 4.95-4.82 (m, 1H), 4.28-4.02 (m, 1H), 3.28-3.15 (m, 1H), 3.06-2.98 (m, 1H), 2.40-2.16 (m, 2H), 1.58-1.50 (m, 1H), 1.41-1.16 (m, 2H), 1.04-0.81 (m, 6H), 0.64-0.47 (m, 1H), 0.41 (br d, J=9.3 Hz, 1H).

Embodiment 2

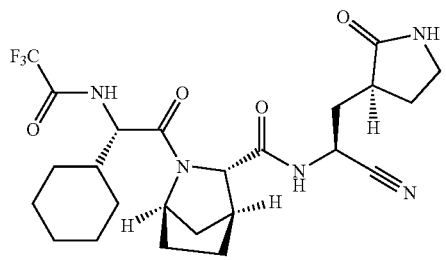

Synthetic route

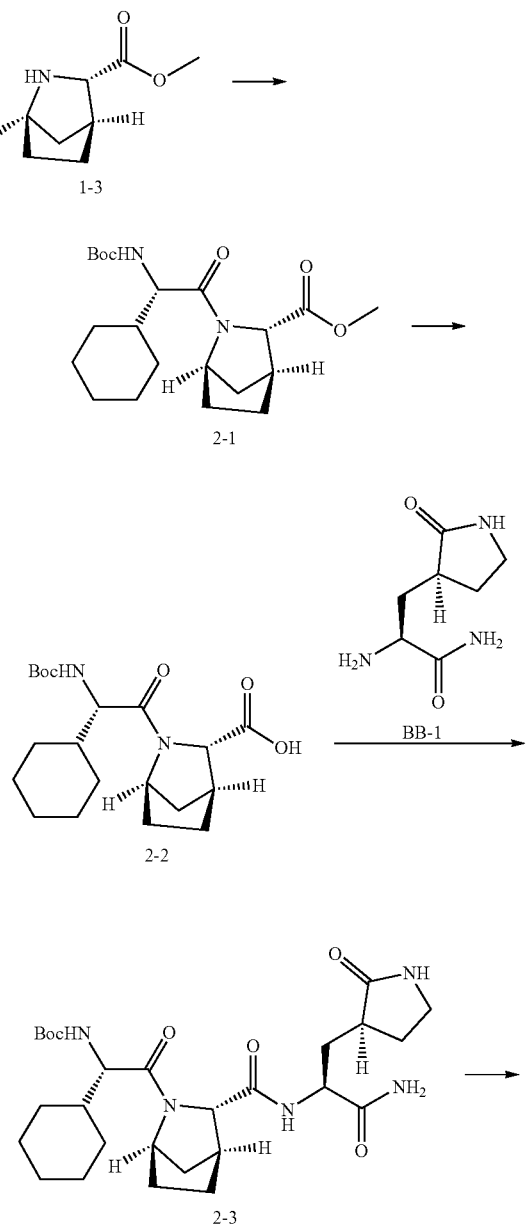

-continued

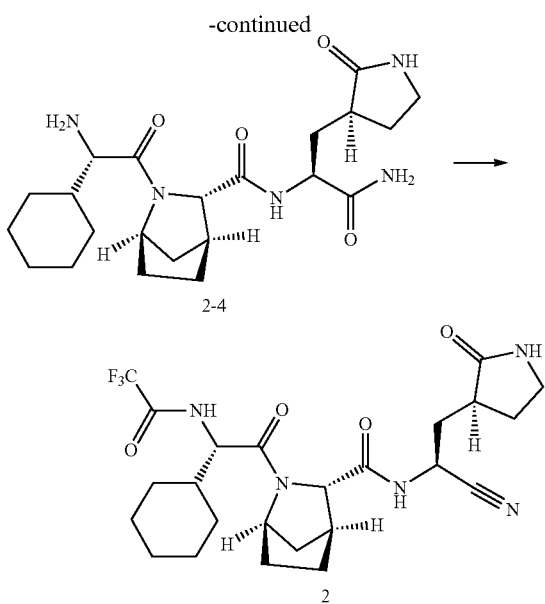

Step 1: Synthesis of compound 2-1

At 0° C., Boc-L-cyclohexylglycine (0.5 g, 2.61 mmol), N,N-diisopropylethylamine (1.01 g, 7.83 mmol), 2-(7-azabenzotriazol-1-yl)-N,N,N,N-tetramethyluronium hexafluorophosphate (1.49 g, 3.92 mmol) were added to a solution of hydrochloride of compound 1-3 (671.62 mg, 2.61 mmol) in N,N-dimethylformamide (5 mL), and the reaction mixture was reacted at 20° C. for 16 hours. The reaction mixture was poured into 5% citric acid solution to separate the phases, then the aqueous phase was extracted with ethyl acetate (50 mL×2), and the organic phase was dried over anhydrous sodium sulfate, filtered, and concentrated under reduced pressure to obtain a crude product. The crude product was separated by silica gel column chromatography (petroleum ether/ethyl acetate=3:1) to obtain compound 2-1. $^1$H NMR (400 MHz, CDCl$_3$) δ=5.16 (br d, J=9.4 Hz, 1H), 4.48-4.34 (m, 1H), 4.32-4.23 (m, 1H), 4.08-4.00 (m, 1H), 3.71 (s, 3H), 2.77-2.69 (m, 1H), 2.05-1.99 (m, 1H), 1.91-1.62 (m, 11H), 1.45-1.41 (m, 9H), 1.23-1.03 (m, 4H).

Step 2: Synthesis of Compound 2-2

Lithium hydroxide monohydrate (212.72 mg, 5.07 mmol) was added to a solution of compound 2-1 (1 g, 2.53 mmol) in tetrahydrofuran (10 mL) and water (5 mL), and the reaction mixture was reacted at 20° C. for 16 hours. The reaction mixture was added with 50 mL of 5% citric acid aqueous solution, and 50 mL of ethyl acetate was added to separate the phases, and the organic phase was dried over anhydrous sodium sulfate, filtered and concentrated to obtain a crude product. Compound 2-2 was obtained. $^1$H NMR (400 MHz, CDCl$_3$) δ=5.17 (br d, J=9.7 Hz, 1H), 4.39 (br s, 1H), 4.35-4.24 (m, 1H), 4.16-4.11 (m, 1H), 3.04-2.93 (m, 1H), 1.96 (br d, J=10.3 Hz, 1H), 1.87-1.53 (m, 11H), 1.44 (s, 9H), 1.19-0.95 (m, 4H).

Step 3: Synthesis of Compound 2-3

At 0° C., hydrochloride of compound BB-1 (438.81 mg, 2.11 mmol), N,N-diisopropylethylamine (682.77 mg, 5.28 mmol, 920.18 μL), 1-hydroxybenzotriazole (285.53 mg, 2.11 mmol), hydrochloride of 1-(3-dimethylaminopropyl)-3-acetaldehyde (405.09 mg, 2.11 mmol) were added to a solution of compound 2-2 (0.65 g, 1.66 mmol) in butanone (10 mL), and the reaction mixture was reacted at 20° C. for 16 hours. The reaction mixture was poured into 20 mL of water, and extracted with a mixed solution of dichloromethane and methanol (dichloromethane:methanol=10:1, 50 mL×2), and the organic phase was dried over anhydrous sodium sulfate, filtered and concentrated to obtain a crude product. The crude product was separated by silica gel column chromatography (dichloromethane:methanol=20:1) to obtain compound 2-3. $^1$H NMR (400 MHz, DMSO-d$_6$) δ=8.08 (br d, J=8.4 Hz, 1H), 7.75-7.55 (m, 1H), 7.32-7.18 (m, 1H), 7.08-6.94 (m, 1H), 6.87-6.64 (m, 1H), 4.42-4.31 (m, 1H), 4.20 (ddd, J=3.8, 8.2, 11.6 Hz, 1H), 4.11-4.00 (m, 3H), 3.14-2.96 (m, 2H), 2.55 (br s, 1H), 2.42-2.32 (m, 1H), 2.21-2.09 (m, 1H), 2.04-1.95 (m, 1H), 1.93-1.81 (m, 1H), 1.78-1.49 (m, 11H), 1.40-1.24 (m, 11H), 1.14-0.86 (m, 5H).

Step 4: Synthesis of Trifluoroacetate of Compound 2-4

At 0° C., trifluoroacetic acid (5 mL) was added to a solution of compound 2-3 (0.86 g, 1.61 mmol) in dichloromethane (15 mL), and the reaction mixture was reacted at 20° C. for 2 hours. The reaction mixture was concentrated under reduced pressure to obtain a crude product. Trifluoroacetate of compound 2-4 was obtained.

Step 5: Synthesis of Compound 2

At 0° C., pyridine (1.41 g, 17.87 mmol) and trifluoroacetic anhydride (782.03 mg, 3.72 mmol) were added to a solution of trifluoroacetate of compound 2-4 (0.7 g, 1.49 mmol) in tetrahydrofuran (10 mL), and the reaction mixture was reacted at 20° C. for 2 hours. The reaction mixture was added with 20 mL of water for quenching, and ethyl acetate (20 mL×2) was added for extraction, then the organic phase was washed with 5% citric acid (20 mL×1), dried over anhydrous sodium sulfate, filtered and concentrated under reduced pressure to obtain a crude product. The crude product was separated by preparative HPLC (column type: Phenomenex C18 75*30 mm*3 m; mobile phase: [H$_2$O (NH$_4$HCO$_3$)-ACN]; ACN %: 25%-65%, 8 min) to obtain compound 2. $^1$H NMR (400 MHz, DMSO-d$_6$) δ=9.67 (br d, J=7.2 Hz, 1H), 8.90-8.74 (m, 1H), 7.76-7.60 (m, 1H), 5.05-4.88 (m, 1H), 4.56-4.46 (m, 1H), 4.45-4.29 (m, 1H), 3.75 (s, 1H), 3.18-3.02 (m, 2H), 2.46-2.38 (m, 1H), 2.16-2.04 (m, 3H), 1.87-1.59 (m, 11H), 1.39-1.26 (m, 2H), 1.16-0.95 (m, 5H).

Embodiment 3

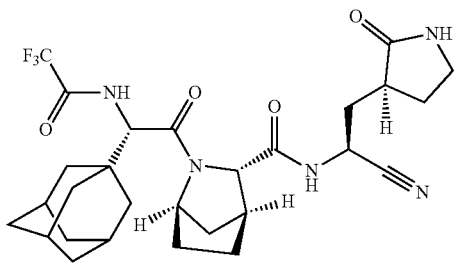

Synthetic route

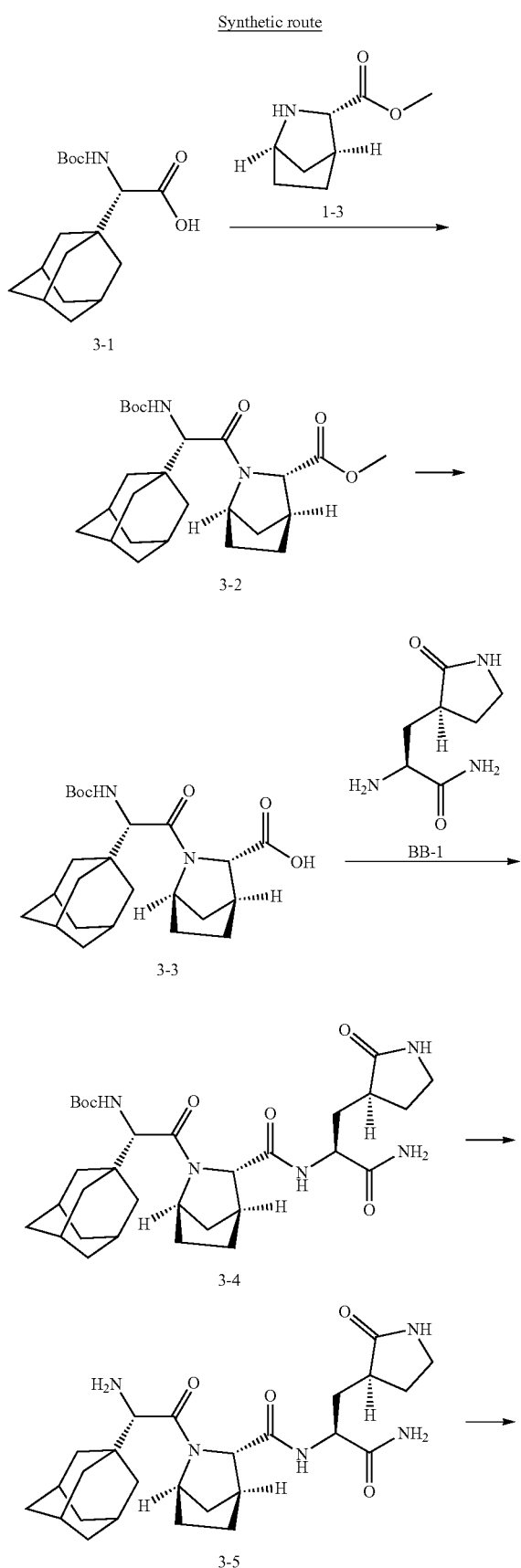

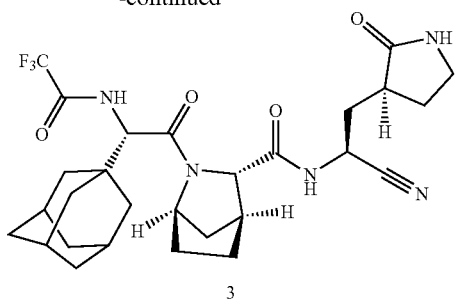

Step 1: Synthesis of Compound 3-2

Compound 3-1 (1 g, 3.23 mmol) was dissolved in N,N-dimethylformamide (10 mL), and O-(7-azabenzotriazol-1-yl)-N,N,N,N-tetramethyluronium hexafluorophosphate (1.84 g, 4.85 mmol) was added thereto. The reaction was stirred at 20° C. for 0.5 hours, then diisopropylethylamine (2.09 g, 16.16 mmol) and hydrochloride of compound 1-3 (601.92 mg, 3.88 mmol) were added and the reaction mixture was reacted at 20° C. for 16 hours. The reaction system was added with ethyl acetate (50 mL), and added with 3% citric acid solution (25 mL) and saturated brine (25 mL) in turn for extraction to separate the organic phase, and the organic phase was dried over anhydrous sodium sulfate, filtered, and concentrated. The residue was purified by silica gel column chromatography (petroleum ether: ethyl acetate=1:0 to 10:1) to obtain compound 3-2. $^1$H NMR (400 MHz, CD$_3$OD) δ=6.27 (br d, J=9.6 Hz, 1H), 4.62 (br s, 1H), 4.19 (d, J=9.6 Hz, 1H), 3.99 (s, 1H), 3.74-3.68 (m, 3H), 2.71 (br s, 1H), 1.92-1.49 (m, 21H), 1.44 (s, 9H).

Step 2: Synthesis of Compound 3-3

Compound 3-2 (1.2 g, 2.69 mmol) was dissolved in tetrahydrofuran (9 mL) and water (4 mL), and lithium hydroxide monohydrate (225.52 mg, 5.37 mmol) was added thereto, and the reaction mixture was stirred at 20° C. for 16 hours. The reaction system was added with ethyl acetate (60 mL) and 3% citric acid (30 mL) for extraction to separate the organic phase, and the organic phase was washed with saturated brine (30 mL×2) to neutral, dried over anhydrous sodium sulfate, filtered, and concentrated. Compound 3-3 was obtained. $^1$H NMR (400 MHz, CD$_3$OD) δ=4.60 (br s, 1H), 4.22-4.15 (m, 1H), 3.95 (s, 1H), 2.74 (br s, 1H), 2.05-1.94 (m, 6H), 1.87-1.61 (m, 15H), 1.46-1.40 (m, 9H).

Step 3: Synthesis of Compound 3-4

Compound 3-3 (1.1 g, 2.54 mmol) was dissolved in 2-butanone (12 mL), then 1-hydroxybenzotriazole (343.62 mg, 2.54 mmol) and hydrochloride of 1-(3-dimethylaminopropyl)-3-ethylcarbodiimide (585.01 mg, 3.05 mmol) were added thereto, and the reaction mixture was stirred at 20° C. for 0.5 hours. Then diisopropylethylamine (1.64 g, 12.72 mmol) and hydrochloride of compound BB-1 (580.89 mg, 2.80 mmol) were added thereto, and the reaction mixture was stirred continuously at 20° C. for 16 hours. The reaction system was added with dichloromethane (60 mL) and 3% citric acid (30 mL) for extraction to separate the organic phase, and the organic phase was washed with saturated brine (30 mL×2) to neutral to separate the organic phase, and the organic phase was dried over anhydrous sodium sulfate, filtered and evaporated to dryness by rotary evaporation. The residue was purified by silica gel column chromatography (dichloromethane:methanol=1:0 to 10:1) to obtain compound 3-4. $^1$H NMR (400 MHz, CD$_3$OD) δ=4.58 (br s, 1H), 4.51-4.41 (m, 1H), 4.20 (s, 1H), 3.95 (s, 1H), 3.36-3.30 (m, 2H), 2.72 (br s, 1H), 2.69-2.59 (m, 1H), 2.43-2.30 (m, 1H), 2.22 (br d, J=9.8 Hz, 1H), 2.15-2.07 (m, 1H), 1.97 (br s, 4H), 1.77-1.61 (m, 18H), 1.44 (s, 9H).

Step 4: Synthesis of Trifluoroacetate of Compound 3-5

Compound 3-4 (1.1 g, 1.88 mmol) was dissolved in dichloromethane (20 mL), and trifluoroacetic acid (5 mL) was added thereto, and the reaction mixture was stirred at 20° C. for 1 hour, and the reaction system was directly evaporated to dryness by an oil pump, added with a small amount of dichloromethane and evaporated by rotary evaporation, and the above steps were repeated until the shape of the product was a white foam. Trifluoroacetate of compound 3-5 was obtained. $^1$H NMR (400 MHz, CD$_3$OD) δ=4.55 (s, 1H), 4.49 (dd, J=3.6, 11.9 Hz, 1H), 4.02 (s, 1H), 3.85 (s, 1H), 3.30-3.19 (m, 2H), 2.77 (br s, 1H), 2.72-2.63 (m, 1H), 2.45-2.31 (m, 1H), 2.23 (br d, J=10.0 Hz, 1H), 2.17-2.10 (m, 1H), 2.04 (br s, 4H), 1.94-1.67 (m, 21H). [M+1]$^+$=486.3.

Step 5: Synthesis of Compound 3

Trifluoroacetate of compound 3-5 (900 mg, 1.85 mmol) was dissolved in tetrahydrofuran (10 mL), then pyridine (1.47 g, 18.53 mmol, 1.50 mL) and trifluoroacetic anhydride (973.13 mg, 4.63 mmol, 644.46 L) were added thereto at 0° C., and the temperature was slowly raised to 20° C., then the reaction mixture was stirred for 16 hours. The reaction system was added with dichloromethane (50 mL) and 3% citric acid (25 mL) for extraction to separate the organic phase, and the organic phase was extracted with saturated brine (25 mL) to separate the organic phase, and the organic phase was dried over anhydrous sodium sulfate, filtered, and the crude product was separated by preparative HPLC to obtain compound 3. $^1$H NMR (400 MHz, CD$_3$OD) δ=5.06 (dd, J=4.7, 11.3 Hz, 1H), 4.66 (s, 1H), 4.61 (s, 1H), 3.87 (s, 1H), 3.32-3.18 (m, 2H), 2.73-2.63 (m, 2H), 2.39-2.27 (m, 3H), 2.01 (br s, 4H), 1.84 (br s, 2H), 1.81 (br s, 2H), 1.77-1.65 (m, 11H), 1.63-1.41 (m, 3H).

Embodiment 4

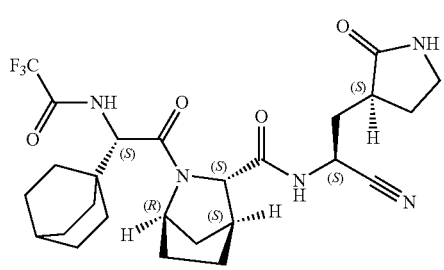

Synthetic route

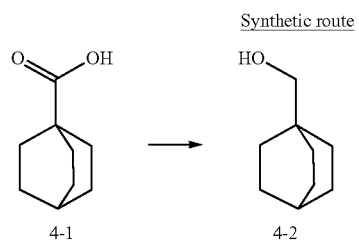

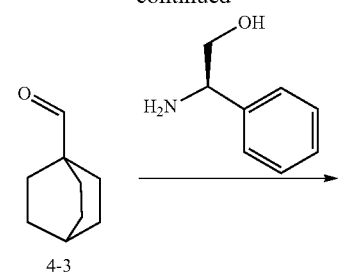

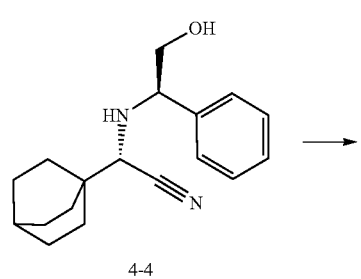

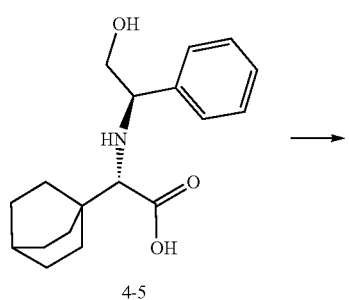

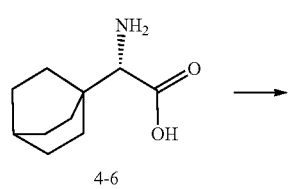

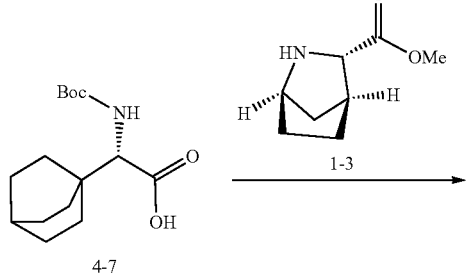

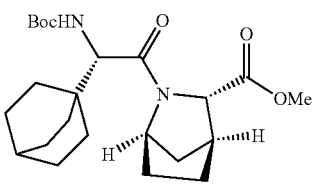

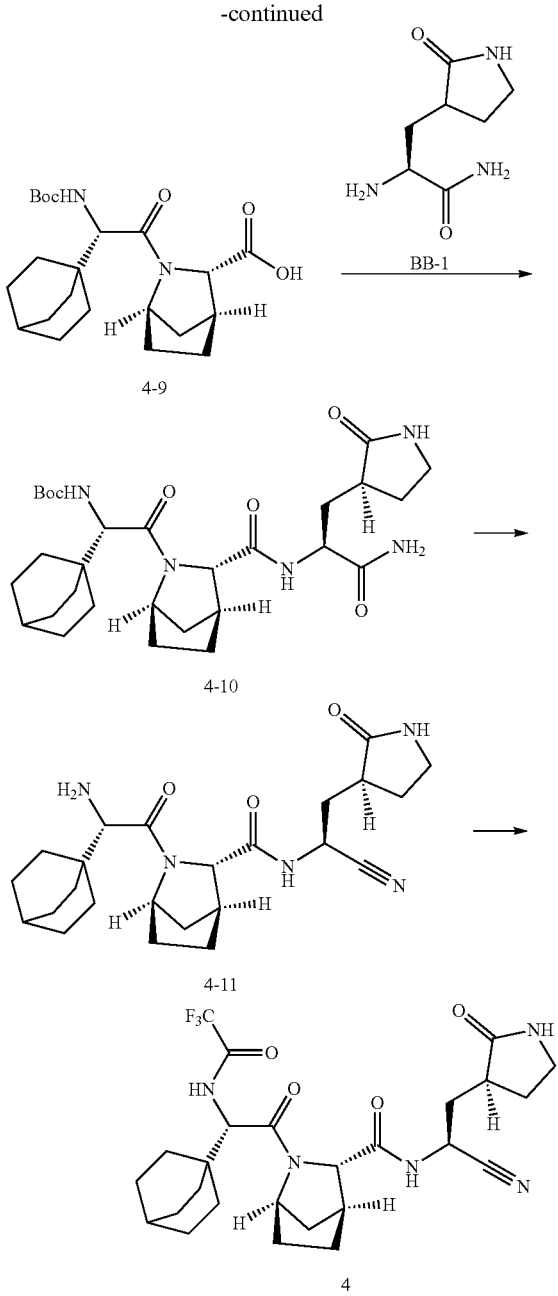

Step 1: Synthesis of Compound 4-2

Compound 4-1 (2.74 g, 17.76 mmol) was dissolved in tetrahydrofuran (27.4 mL), and the reaction system was replaced with nitrogen for three times, cooled to 0° C., then a solution of borane in tetrahydrofuran (35.52 mL, 1 M) was slowly added dropwise thereto. The reaction was stirred at 20° C. for 16 hours, added with sodium hydroxide solution (80 mL, 1M) at 0° C., extracted twice with methyl tert-butyl ether (100 mL), and the organic phases were combined and washed with 10% citric acid (80 mL×2) and saturated brine (80 mL), dried over anhydrous sodium sulfate, filtered and concentrated. Compound 4-2 was obtained. $^1$H NMR (400 MHz, CDCl$_3$) δ ppm 3.19 (s, 2H) 1.50-1.59 (m, 7H) 1.29-1.38 (m, 6H).

Step 2: Synthesis of Compound 4-3

Compound 4-2 (2.26 g, 16.09 mmol) was dissolved in dichloromethane (67.8 mL), and Dess-Martin periodinane (10.24 g, 24.14 mmol) was added to the reaction system. The reaction was stirred at 20° C. for 16 hours. The reaction mixture was added with sodium thiosulfate (50 mL) and saturated sodium bicarbonate solution (70 mL), and extracted twice with dichloromethane (100 mL). The combined organic phases were dried over anhydrous sodium sulfate, filtered, and concentrated. Compound 4-3 was obtained. $^1$H NMR (400 MHz, CDCl$_3$) δ ppm 9.41 (s, 1H) 1.60 (s, 13H).

Step 3: Synthesis of Compound 4-4

Compound 4-3 (1.97 g, 14.25 mmol) was dissolved in methanol (137.9 mL), and compound R-phenylglycinol (2.35 g, 17.10 mmol) was added to the reaction system, and the reaction mixture was stirred at 20° C. for 2 hours. The reaction mixture was cooled to 0° C., added with trimethylsilyl cyanide (9.90 g, 99.78 mmol), and stirred at 50° C. for 16 hours. The reaction mixture was directly evaporated to dryness by rotary evaporation. The residue was purified by silica gel column chromatography (petroleum ether: ethyl acetate=10:1) to obtain compound 4-4. $^1$H NMR (400 MHz, CDCl$_3$) δ ppm 7.28-7.39 (m, 5H) 4.06 (dd, J=9.10, 4.06 Hz, 1H) 3.80 (dd, J=10.96, 3.95 Hz, 1H) 3.58 (t, J=9.98 Hz, 1H) 2.89 (s, 1H) 1.56-1.65 (m, 13H).

Step 4: Synthesis of Hydrochloride of Compound 4-5

Compound 4-4 (1.42 g, 4.99 mmol) was dissolved in hydrochloric acid (28.4 mL) and glacial acetic acid (7.1 mL), and the reaction was stirred at 80° C. for 16 hours. The reaction mixture was cooled to 0° C. to precipitate the solid, and filtered. Hydrochloride of compound 4-5 was obtained. [M+1]+=303.2.

Step 5: Synthesis of Hydrochloride of Compound 4-6

Hydrochloride of compound 4-5 (2.24 g, 7.38 mmol) was dissolved in methanol (112 mL) and glacial acetic acid (22.4 mL), then 20% wet palladium hydroxide (0.448 g, 638.02 µmol) was added thereto. 50 psi hydrogen was introduced to the reaction system, and the reaction mixture was heated to 50° C. and stirred for 18 hours. The reaction mixture was filtrated and directly evaporated to dryness by rotary evaporation, and slurried with methyl tert-butyl ether (40 mL), and filtered. Hydrochloride of compound 4-6 was obtained. $^1$H NMR (400 MHz, CD$_3$OD) δ ppm 3.53 (s, 1H) 1.47-1.71 (m, 13H) 3.53 (s, 1H).

Step 6: Synthesis of Compound 4-7

Hydrochloride of compound 4-6 (50 mg, 272.86 µmol) was dissolved in 1,4-dioxane (0.375 mL) and water (1 mL), then anhydrous sodium carbonate (115.68 mg, 1.09 mmol) and di-tert-butyl dicarbonate (119.10 mg, 545.71 µmol) were added thereto, and the reaction was stirred at 20° C. for 16 hours. The reaction mixture was added with water (5 mL) and 5% citric acid (10 mL), and extracted twice with ethyl acetate (20 mL), and the organic phases were combined, washed with saturated brine (20 mL), dried over anhydrous sodium sulfate, filtered and evaporated to dryness by rotary evaporation. Compound 4-7 was obtained. $^1$H NMR (400 MHz, CDCl$_3$) δ ppm 4.98 (br d, J=8.63 Hz, 1H) 3.97-4.05 (m, 1H) 1.43-1.62 (m, 22H).

Step 7: Synthesis of Compound 4-8

Compound 4-7 (250 mg, 882.26 µmol) was dissolved in N,N-dimethylformamide (2.5 mL), then 1-hydroxybenzotriazole (357.64 mg, 2.65 mmol) and hydrochloride of 1-(3-dimethylaminopropyl)-3-ethylcarbodiimide (338.26 mg, 1.76 mmol) were added thereto, and the reaction mixture was stirred at 20° C. for 0.5 hours, then N,N-diisopropylethylamine (342.08 mg, 2.65 mmol) and hydrochloride of compound 1-3 (136.92 mg, 882.26 µmol) were added thereto, and the reaction was stirred at 20° C. for 16 hours. The reaction mixture was added with water (10 mL), extracted twice with ethyl acetate (20 mL), then the organic phases were combined, washed twice with 5% citric acid (15 mL), and washed four times with brine (10 mL), then dried over anhydrous sodium sulfate, filtered, and evaporated to dryness by rotary evaporation. The residue was purified by column chromatography (petroleum ether: ethyl acetate=8:1) to obtain compound 4-8. $^1$H NMR (400 MHz, CDCl$_3$) δ ppm 5.20 (br d, J=9.63 Hz, 1H) 4.48-4.54 (m, 1H) 4.22-4.30 (m, 1H) 4.02-4.11 (m, 1H) 3.76 (s, 3H) 2.76 (br s, 1H) 2.05 (br d, J=10.38 Hz, 1H) 1.68-1.84 (m, 4H) 1.60 (s, 13H) 1.46 (s, 9H).

Step 8: Synthesis of Compound 4-9

Compound 4-8 (300 mg, 713.37 μmol) was dissolved in tetrahydrofuran (3 mL) and water (1 mL), then lithium hydroxide monohydrate (59.87 mg, 1.43 mmol) was added thereto and the reaction mixture was stirred at 20° C. for 16 hours. The reaction mixture was added with water (10 mL) and 5% citric acid (15 mL), extracted twice with ethyl acetate (15 mL). The organic phases were combined, washed with saturated brine (15 mL), dried over anhydrous sodium sulfate, filtered, and evaporated to dryness by rotary evaporation. Compound 4-9 was obtained without purification. $^1$H NMR (400 MHz, CDCl$_3$) δ ppm 5.07-5.17 (m, 1H) 4.42-4.47 (m, 1H) 4.26 (br d, J=9.88 Hz, 1H) 4.17 (s, 1H) 3.07 (br s, 1H) 1.70-1.98 (m, 5H) 1.46-1.67 (m, 13H).

Step 9: Synthesis of Compound 4-10

Compound 4-9 (266 mg, 654.36 μmol) was dissolved in 2-butanone, then 1-hydroxybenzotriazole (88.42 mg, 654.34 μmol) and hydrochloride of 1-(3-dimethylaminopropyl)-3-ethylcarbodiimide (150.53 mg, 785.21 μmol) were added thereto, and the reaction mixture was stirred at 20° C. for 0.5 hours, and N,N-diisopropylethylamine (338.28 mg, 2.62 mmol) and hydrochloride compound BB-1 (134.42 mg, 785.21 μmol) were added thereto, and the reaction was stirred at 20° C. for 16 hours. The reaction mixture was added with water (10 mL), extracted twice with dichloromethane (20 mL), and the organic phases were combined and washed twice with 5% citric acid (15 mL), washed twice with brine (10 mL), and then dried over anhydrous sodium sulfate, filtered, and evaporated to dryness by rotary evaporation. The residue was purified by column chromatography (dichloromethane:methanol=20:1) to obtain compound 4-10. [M+1]$^+$=560.4.

Step 10: Synthesis of Trifluoroacetate of Compound 4-11

Compound 4-10 (166 mg, 296.59 μmol) was dissolved in dichloromethane (1.8 mL) and trifluoroacetic acid (0.6 mL), and the reaction was stirred at 20° C. for 2 hours. The reaction was directly evaporated to dryness by an oil pump, added with a small amount of dichloromethane and evaporated by rotary evaporation, and the above steps were repeated until the shape of the product was a light yellow foam. Trifluoroacetate of compound 4-11 was obtained. [M+1]$^+$=460.4.

Step 11: Synthesis of Compound 4

Trifluoroacetate of compound 4-11 (136 mg, 295.92 μmol) was dissolved in tetrahydrofuran (1.4 mL), cooled to 0° C., then pyridine (79.10 mg, 2.07 mmol) and trifluoroacetic anhydride (210.03 mg, 1.18 mmol) were added thereto. The reaction was raised to room temperature of 20° C. and stirred for 16 hours. The reaction mixture was extracted twice with water (10 mL) and extracted twice with dichloromethane (10 mL), and the organic phases were combined and washed twice with 3% citric acid (10 mL), and washed twice with saturated brine (10 mL), dried over anhydrous sodium sulfate, filtered and concentrated. The crude product was separated by preparative HPLC (column type: C18-2 100*30 mm*5 μm; mobile phase: [H$_2$O (NH$_4$HCO$_3$)-ACN]; ACN %: 30%-50%, 20 min) to obtain compound 4. $^1$H NMR (400 MHz, CDCl$_3$) δ=9.39-8.06 (m, 1H), 7.14-6.89 (m, 1H), 6.10-5.81 (m, 1H), 4.99-4.69 (m, 1H), 4.63-4.39 (m, 1H), 4.03-3.86 (m, 1H), 3.48-3.26 (m, 2H), 2.98-2.79 (m, 1H), 2.61-1.17 (m, 25H).

Embodiment 5

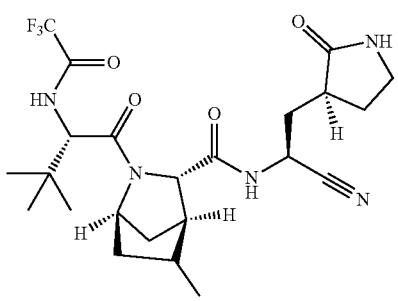

5

Synthetic route

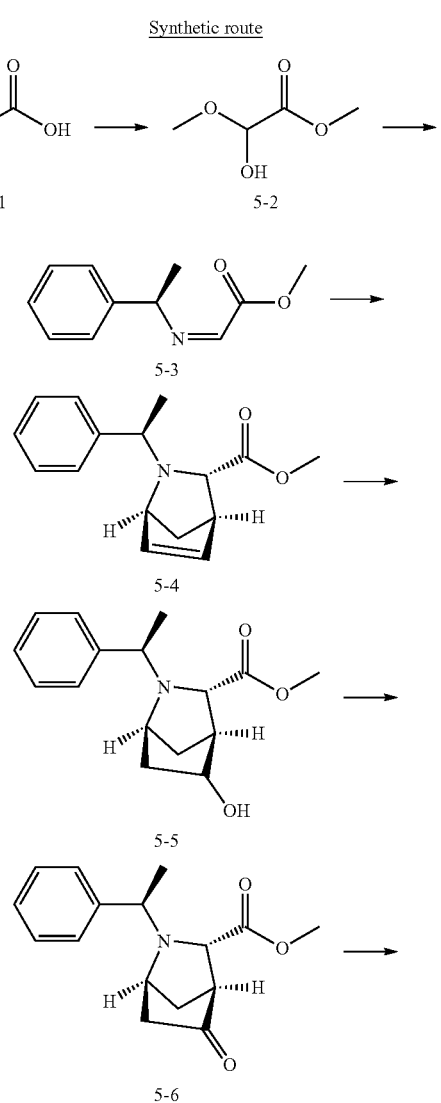

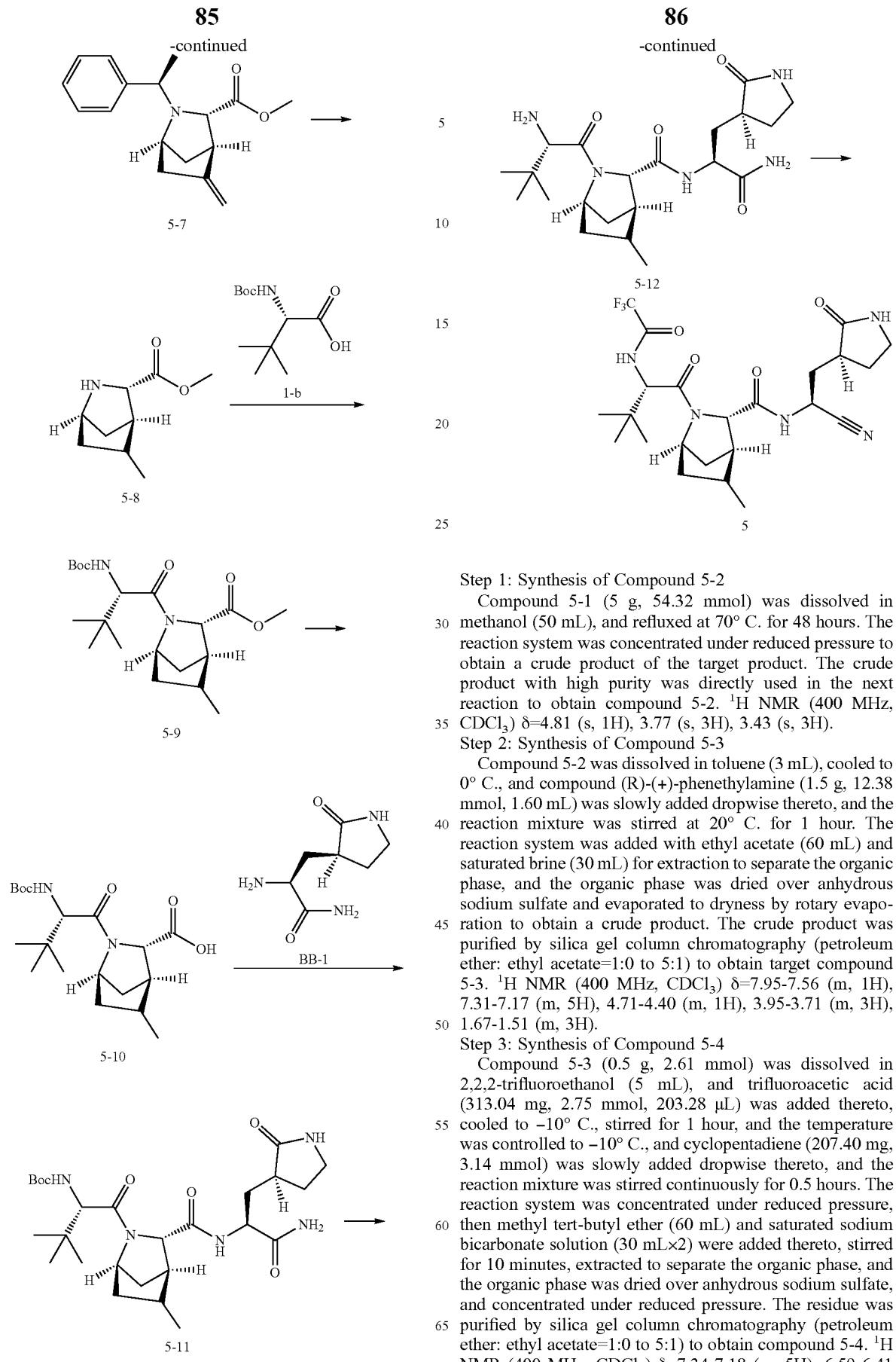

Step 1: Synthesis of Compound 5-2

Compound 5-1 (5 g, 54.32 mmol) was dissolved in methanol (50 mL), and refluxed at 70° C. for 48 hours. The reaction system was concentrated under reduced pressure to obtain a crude product of the target product. The crude product with high purity was directly used in the next reaction to obtain compound 5-2. $^1$H NMR (400 MHz, CDCl$_3$) δ=4.81 (s, 1H), 3.77 (s, 3H), 3.43 (s, 3H).

Step 2: Synthesis of Compound 5-3

Compound 5-2 was dissolved in toluene (3 mL), cooled to 0° C., and compound (R)-(+)-phenethylamine (1.5 g, 12.38 mmol, 1.60 mL) was slowly added dropwise thereto, and the reaction mixture was stirred at 20° C. for 1 hour. The reaction system was added with ethyl acetate (60 mL) and saturated brine (30 mL) for extraction to separate the organic phase, and the organic phase was dried over anhydrous sodium sulfate and evaporated to dryness by rotary evaporation to obtain a crude product. The crude product was purified by silica gel column chromatography (petroleum ether: ethyl acetate=1:0 to 5:1) to obtain target compound 5-3. $^1$H NMR (400 MHz, CDCl$_3$) δ=7.95-7.56 (m, 1H), 7.31-7.17 (m, 5H), 4.71-4.40 (m, 1H), 3.95-3.71 (m, 3H), 1.67-1.51 (m, 3H).

Step 3: Synthesis of Compound 5-4

Compound 5-3 (0.5 g, 2.61 mmol) was dissolved in 2,2,2-trifluoroethanol (5 mL), and trifluoroacetic acid (313.04 mg, 2.75 mmol, 203.28 μL) was added thereto, cooled to −10° C., stirred for 1 hour, and the temperature was controlled to −10° C., and cyclopentadiene (207.40 mg, 3.14 mmol) was slowly added dropwise thereto, and the reaction mixture was stirred continuously for 0.5 hours. The reaction system was concentrated under reduced pressure, then methyl tert-butyl ether (60 mL) and saturated sodium bicarbonate solution (30 mL×2) were added thereto, stirred for 10 minutes, extracted to separate the organic phase, and the organic phase was dried over anhydrous sodium sulfate, and concentrated under reduced pressure. The residue was purified by silica gel column chromatography (petroleum ether: ethyl acetate=1:0 to 5:1) to obtain compound 5-4. $^1$H NMR (400 MHz, CDCl$_3$) δ=7.34-7.18 (m, 5H), 6.59-6.41

(m, 1H), 6.31 (dd, J=1.6, 5.6 Hz, 1H), 4.35 (br d, J=1.3 Hz, 1H), 3.39 (s, 3H), 3.18-3.03 (m, 1H), 2.95 (br s, 1H), 2.33-2.22 (m, 1H), 2.14 (br d, J=8.4 Hz, 1H), 1.54-1.41 (m, 4H). $[M+1]^+$=258.2.

Step 4: Synthesis of Compound 5-5

Compound 5-4 (100.00 mg, 388.61 μmol) was dissolved in tetrahydrofuran (1.25 mL), cooled to −70° C., and borane tetrahydrofuran complex (1 M, 427.47 μL) was slowly added dropwise thereto and the reaction mixture was slowly raised to 20° C. and stirred for 1 hour. The reaction mixture was cooled to 0° C., and 10% sodium hydroxide aqueous solution (0.55 mL) and 30% hydrogen peroxide (220.28 mg, 1.94 mmol, 186.68 μL) solution were added thereto, then the temperature was slowly raised to 20° C., and the reaction mixture was stirred for 1 hour. The reaction system was added with saturated sodium thiosulfate solution (10 mL) and stirred for 10 minutes to quench, and saturated brine (20 mL) and ethyl acetate (60 mL×2) were added for extraction to separate the organic phase. A small amount of sample solution was taken, and the pH was adjusted with 3% citric acid to less than 8, and after starch potassium iodide test paper showed negative results, the mixture was dried over anhydrous sodium sulfate and concentrated at 30° C. under reduced pressure. The residue was purified by silica gel column chromatography (petroleum ether: ethyl acetate=1:0 to 5:1) to obtain compound 5-5. $^1$H NMR (400 MHz, $CDCl_3$) δ=7.30-7.13 (m, 5H), 3.93 (br d, J=6.5 Hz, 1H), 3.78 (br s, 1H), 3.70-3.54 (m, 1H), 3.39-3.32 (m, 1H), 3.31-3.24 (m, 3H), 2.49-2.40 (m, 1H), 2.26 (s, 1H), 2.09-2.00 (m, 1H), 1.72 (br d, J=10.1 Hz, 1H), 1.46 (br d, J=6.5 Hz, 1H), 1.41-1.33 (m, 3H). $[M+1]^+$=276.1.

Step 5: Synthesis of Compound 5-6

Compound 5-5 (800 mg, 2.91 mmol) was dissolved in acetonitrile (10 mL), and 2-iodoxybenzoic acid (976.31 mg, 3.49 mmol) was added thereto and the reaction mixture was reacted at 75° C. for 1 hour. The reaction system was dried over anhydrous sodium sulfate, filtered, and the filter cake was washed with acetonitrile (10 mL), and the filtrates were combined and concentrated to obtain compound 5-6. $[M+1]^+$=274.0.

Step 6: Synthesis of Compound 5-7

Compound 5-6 was dissolved in tetrahydrofuran (20 mL) and cooled to 0° C., and under nitrogen atmosphere, 0.5 μM toluene solution of bis(cyclopentadienyl)-g-chloro(dimethylaluminum)-g-methylenetitanium (0.5 M, 4.02 mL) was slowly added dropwise thereto, and the temperature was slowly raised to 20° C., and the reaction mixture was stirred for 2.5 hours. The temperature was lowered to 0° C., and saturated sodium bicarbonate solution (1 mL) was added to the reaction system for quenching, then methyl tert-butyl ether (10 mL) was added thereto, and anhydrous sodium sulfate was added to dry, and the mixture was concentrated under reduced pressure. The residue was purified by silica gel column chromatography (petroleum ether: ethyl acetate=1:0 to 10:1) to obtain compound 5-7. $^1$H NMR (400 MHz, $CDCl_3$) δ=7.28-7.09 (m, 5H), 4.92 (br s, 1H), 4.71 (s, 1H), 3.81 (s, 1H), 3.48 (q, J=6.5 Hz, 1H), 3.28-3.15 (m, 3H), 2.76-2.69 (m, 2H), 2.65 (br d, J=16.8 Hz, 1H), 2.21 (br d, J=9.8 Hz, 1H), 2.08-1.95 (m, 1H), 1.43 (d, J=9.8 Hz, 1H), 1.31 (d, J=6.5 Hz, 3H). $[M+1]^+$=272.0.

Step 7: Synthesis of Hydrochloride of Compound 5-8

Compound 5-7 (310 mg, 1.14 mmol) was dissolved in ethanol (5 mL), and 12 M of hydrochloric acid (285.61 μL) and wet palladium on carbon (1 g, palladium content of 10%) were added thereto, and the reaction mixture was reacted under a hydrogen balloon atmosphere at 15 psi and 20° C. for 16 hours. The reaction system was filtered through diatomite and the filtrate was evaporated to dryness by rotary evaporation to obtain hydrochloride of compound 5-8. $^1$H NMR (400 MHz, $CD_3OD$) δ=4.17-4.00 (m, 1H), 3.88-3.81 (m, 3H), 3.74-3.41 (m, 1H), 2.55-2.20 (m, 1H), 2.17-1.99 (m, 1H), 1.96-1.71 (m, 3H), 1.36-1.23 (m, 2H), 1.18-1.01 (m, 3H). $[M+1]^+$=170.0.

Step 8: Synthesis of Compound 5-9

Compound 1-b (311.63 mg, 1.35 mmol) was dissolved in N,N-dimethylformamide (3 mL), then O-(7-azabenzotriazol-1-yl)-N,N,N,N-tetramethyluronium hexafluorophosphate (640.38 mg, 1.68 mmol) and diisopropylethylamine (725.55 mg, 5.61 mmol, 977.83 μL) were added thereto, and the reaction mixture was stirred for 30 minutes, then hydrochloride of compound 5-8 (190 mg, 1.12 mmol) was added thereto, and the reaction mixture was stirred continuously at 20° C. for 2.5 hours. The reaction system was added with ethyl acetate (60 mL) and 3% citric acid solution (30 mL) for extraction to separate the organic phase, and the organic phase was extracted with saturated brine (30 mL) to separate the organic phase, and the organic phase was dried over anhydrous sodium sulfate, concentrated under reduced pressure. The residue was purified by silica gel column chromatography (PE:EA=1:0 to 10:1) to obtain compound 5-9. $^1$H NMR (400 MHz, $CDCl_3$) δ=6.62-6.36 (m, 1H), 5.26-5.12 (m, 1H), 4.68-4.63 (m, 1H), 4.34-4.26 (m, 1H), 3.74-3.63 (m, 3H), 2.30-2.18 (m, 1H), 2.11-2.02 (m, 1H), 1.62-1.52 (m, 4H), 1.50 (br s, 3H), 1.13-1.07 (m, 9H), 1.05 (br s, 9H). $[M+1]^+$=383.3.

Step 9: Synthesis of Compound 5-10

Compound 5-9 (0.2 g, 522.89 μmol) was dissolved in tetrahydrofuran (1.5 mL) and water (0.5 mL), and lithium hydroxide monohydrate (43.88 mg, 1.05 mmol) was added thereto, and the reaction mixture was reacted at 20° C. for 16 hours. The reaction system was added with dichloromethane (60 mL) and 3% citric acid (30 mL) for extraction to separate the organic phase, and the organic phase was added with saturated brine (30 mL) for extraction to separate the organic phase, and the organic phase was dried over anhydrous sodium sulfate, and concentrated under reduced pressure to obtain compound 5-10. $[M+1]^+$=369.3.

Step 10: Synthesis of Compound 5-11

Compound 5-10 (190 mg, 515.65 μmol) was dissolved in N,N-dimethylformamide (2 mL), then 1-hydroxybenzotriazole (69.67 mg, 515.65 μmol) and hydrochloride of 1-(3-dimethylaminopropyl)-3-ethylcarbodiimide (118.62 mg, 618.78 μmol) were added thereto, and the reaction mixture was stirred for 30 minutes, then diisopropylethylamine (333.21 mg, 2.58 mmol, 449.07 μL) and hydrochloride of compound BB-1 (128.49 mg, 618.78 μmol) were added thereto, and the reaction mixture was reacted at 20° C. for 2 hours. The reaction system was added with ethyl acetate (50 mL) and 3% citric acid (25 mL) for extraction to separate the organic phase, and the organic phase was extracted with saturated brine (25 mL) to separate the organic phase, and the organic phase was dried over anhydrous sodium sulfate and concentrated under reduced pressure. The residue was purified by silica gel column chromatography (dichloromethane:methanol=1:0 to 30:1) to obtain compound 5-11. $[M+1]^+$=522.4.

Step 11: Synthesis of Trifluoroacetate of Compound 5-12

Compound 5-11 was dissolved in dichloromethane (1 mL), then trifluoroacetic acid (0.3 mL) was added thereto, and the reaction mixture was reacted at 20° C. for 1 hour. The reaction system was concentrated under reduced pressure to obtain trifluoroacetate of compound 5-12. $[M+1]^+$=422.3.

Step 12: Synthesis of Compound 5

Trifluoroacetate of compound 5-12 (80 mg) was dissolved in dichloromethane (1 mL), then pyridine (150.12 mg, 1.90 mmol, 153.18 μL) and trifluoroacetic anhydride (99.65 mg, 474.46 μmol, 65.99 L) were added thereto at 0° C., and the reaction mixture was slowly raised to 20° C. and reacted for 2 hours. The reaction system was added with 3% citric acid solution (30 mL) and dichloromethane (60 mL×2) for extraction to separate the organic phase, and the organic phase was washed with saturated brine (60 mL) until neutral, and concentrated under reduced pressure. The residue was purified by silica gel column chromatography (dichloromethane:methanol=10:1), and then purified by preparative high performance liquid chromatography (column type: Phenomenex Luna 80*30 mm*3 μm; mobile phase: [water (hydrochloric acid)-acetonitrile]; acetonitrile %: 20%-40%, 8 min) to obtain compound 5. $^1$H NMR (400 MHz, CDCl$_3$) δ=9.55-8.15 (m, 1H), 7.21-7.02 (m, 1H), 6.63-5.95 (m, 1H), 4.66 (br d, J=6.0 Hz, 5H), 3.72-3.31 (m, 2H), 2.33-1.33 (m, 9H), 1.19-1.02 (m, 12H). [M+1]$^+$=500.3.

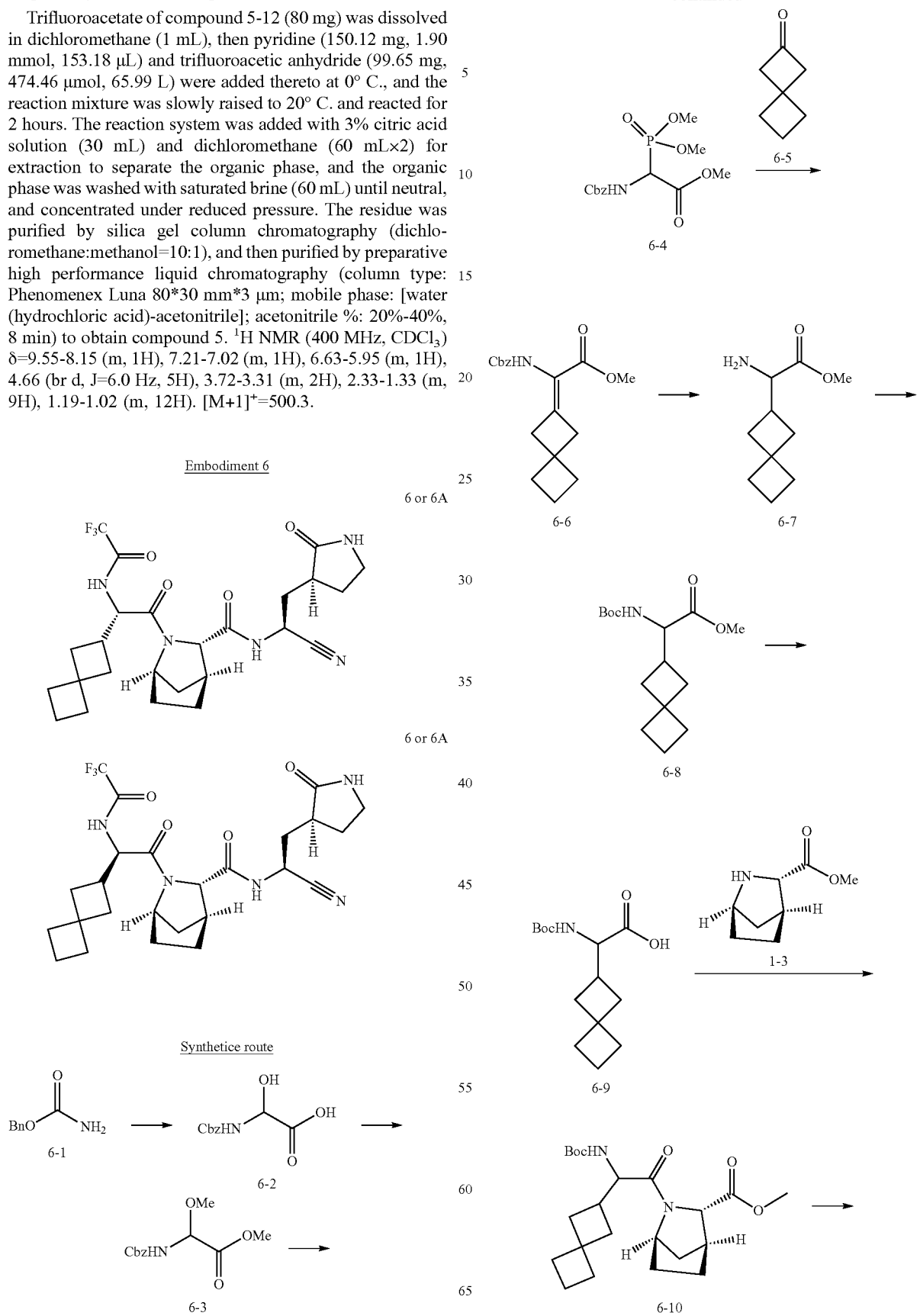

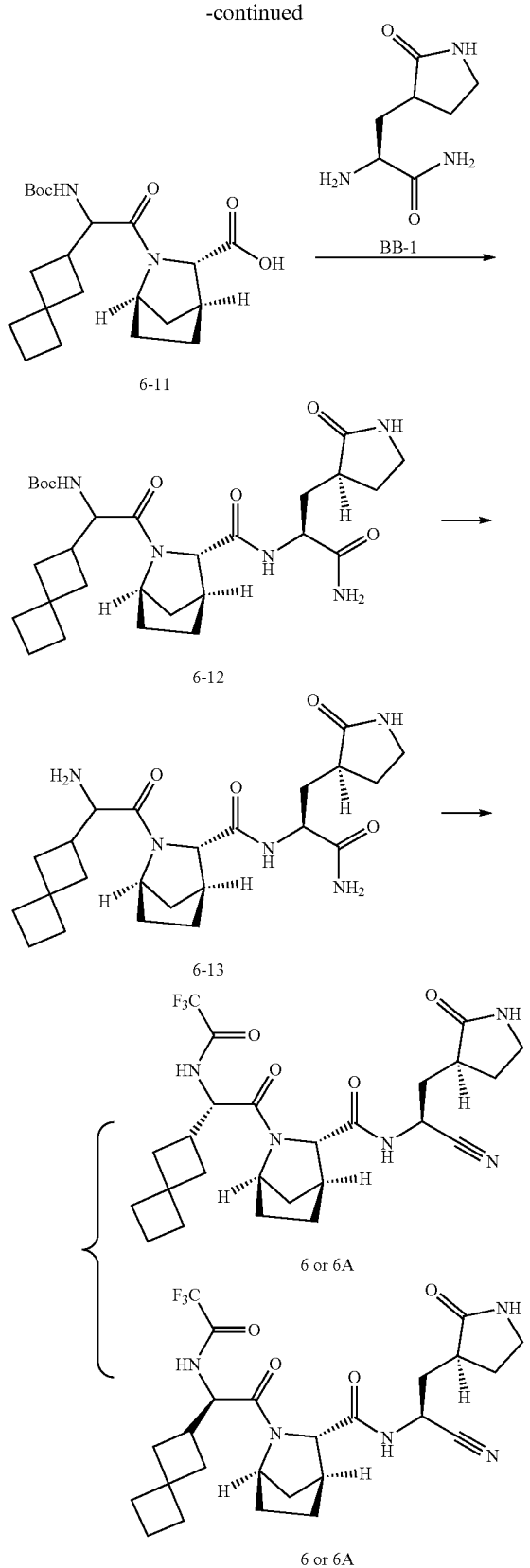

Step 1: Synthesis of Compound 6-2

Compound 6-1 (30 g, 198.46 mmol) and glyoxylic acid (18.27 g, 198.46 mmol, 3.68 mL) were dissolved in anhydrous toluene (300 mL), and the reaction mixture was stirred at 40° C. for 3 hours. The reaction mixture was filtered and concentrated to obtain compound 6-2. $[M+1]^+=226.2$.

Step 2: Synthesis of Compound 6-3

Compound 6-2 was dissolved in anhydrous methanol (420 mL), and sulfuric acid (18.73 g, 190.94 mmol, 10.18 mL) was added thereto, and the reaction mixture was stirred at 20° C. for 48 hours. The reaction mixture was added with methyl tert-butyl ether (300 mL) and water (150 mL) for extraction, and the organic phases were combined, dried over anhydrous sodium sulfate, filtered and concentrated to obtain a crude product of the target product. The crude product was purified by silica gel column chromatography (petroleum ether: ethyl acetate=2:1) to obtain compound 6-3. $^1$H NMR (400 MHz, DMSO-$d_6$) δ=8.52-8.46 (m, 1H), 7.40-7.30 (m, 6H), 5.08 (s, 2H), 3.68-3.64 (m, 3H), 3.26 (s, 3H).

Step 3: Synthesis of Compound 6-4

Compound 6-3 (26 g, 102.67 mmol) was dissolved in sulfuric acid (10.07 g, 102.67 mmol, 5.47 mL), and the mixture was added to anhydrous toluene (260 mL), heated to 70° C. Phosphorus trichloride (49.35 mg, 359.33 μmol) was slowly added dropwise thereto, and the reaction mixture was stirred continuously at 75° C. for 16 hours. Then, the reaction mixture was concentrated under reduced pressure, and added with anhydrous toluene (200 mL) for dilution, and then evaporated by rotary evaporation under reduced pressure, which was repeated for three times. Finally, anhydrous toluene (200 mL) was added, and trimethyl phosphite (15.29 g, 123.20 mmol, 14.56 mL) was slowly added dropwise to the concentrated solution at 75° C., and then heated to 90° C. and reacted for 1.5 hours. The reaction mixture was poured into saturated sodium bicarbonate aqueous solution (360 mL) for quenching, added with ethyl acetate (360 mL) to separate the phases, and the organic phase was concentrated under reduced pressure to obtain a crude product. The crude product was purified by silica gel column chromatography (petroleum ether: ethyl acetate=2:1) to obtain compound 6-4. $^1$H NMR (400 MHz, DMSO-$d_6$) δ=7.41-7.30 (m, 5H), 5.09-5.07 (m, 2H), 4.89-4.83 (m, 1H), 3.73-3.63 (m, 9H).

Step 4: Synthesis of Compound 6-6

At 20° C., compound 6-4 (20 g, 60.38 mmol) was dissolved in acetonitrile (50 mL), and 1,8-diazabicyclo[5.4.0]undec-7-ene (11.03 g, 72.45 mmol, 10.92 mL) was added thereto, and the reaction mixture was stirred for 0.5 hours, then a solution of compound 6-5 (6.65 g, 60.38 mmol) in acetonitrile (20 mL) was added thereto and the reaction mixture was stirred for 16 hours. Ethyl acetate (40 mL) and water (40 mL) were added to the reaction mixture to separate the phases, and the organic phases were combined and evaporated by rotary evaporation under reduced pressure to obtain a crude product. The crude product was purified by silica gel column chromatography (petroleum ether: ethyl acetate=2:1) to obtain compound 6-6. $^1$H NMR (400 MHz, CDCl$_3$) δ=7.41-7.30 (m, 5H), 6.12 (br s, 1H), 5.13 (s, 2H), 3.77-3.71 (m, 3H), 3.11 (s, 2H), 2.87-2.81 (m, 2H), 2.10 (br s, 4H), 1.89-1.79 (m, 2H).

Step 5: Synthesis of Hydrochloride of Compound 6-7

Compound 6-6 (11 g, 34.88 mmol) was dissolved in anhydrous methanol (5 mL), and 10% wet palladium/carbon (2.20 g, 7.33 mol) was added thereto, then 15 psi hydrogen was introduced, and the reaction mixture was stirred at 30° C. for 18 hours. The reaction mixture was filtered through diatomite, and then concentrated under reduced pressure to obtain a crude product. The crude product was not further purified. Hydrochloride of compound 6-7 was obtained. $^1$H NMR (400 MHz, DMSO-$d_6$) δ=3.60-3.57 (m, 3H), 3.32 (s, 2H), 3.17-3.12 (m, 1H), 1.98-1.73 (m, 11H).

Step 6: Synthesis of Compound 6-8

Compound 6-7 (6 g, 32.74 mmol) was added to a solution of water (30 mL) and anhydrous tetrahydrofuran (30 mL), then potassium carbonate (13.58 g, 98.23 mmol) and Boc anhydride (21.44 g, 98.23 mmol, 22.57 mL) were added thereto, and the reaction mixture was stirred at 20° C. for 16 hours. The reaction mixture was added with 5% citric acid (15 mL), and then added with water (40 mL), extracted with ethyl acetate (40 mL) to separate the phases. The aqueous phase was extracted with ethyl acetate (30 mL), then the organic phases were combined, washed with saturated brine (30 mL), dried over anhydrous sodium sulfate and concentrated under reduced pressure. The residue was purified by column chromatography (petroleum ether: ethyl acetate=5: 1) to obtain compound 6-8. $^1$H NMR (400 MHz, DMSO-$d_6$) δ=3.84-3.83 (m, 1H), 3.57-3.52 (m, 1H), 1.99-1.91 (m, 12H), 1.87-1.76 (m, 11H).

Step 7: Synthesis of Compound 6-9

Compound 6-8 (0.8 g, 2.82 mmol) was dissolved in a solution of anhydrous tetrahydrofuran (6 mL) and water (2 mL), and lithium hydroxide monohydrate (236.95 mg, 5.65 mmol) was added to the reaction mixture, then the reaction mixture was stirred at 20° C. for 16 hours. The reaction mixture was added with ethyl acetate (5 mL), washed with water (5 mL), then the aqueous phase was added with 5% citric acid (15 mL) and then added with water (5 mL), and extracted with ethyl acetate (5 mL×2). The organic phases were combined, washed with saturated brine (15 mL), dried over anhydrous sodium sulfate, and concentrated under reduced pressure. The crude product was not further purified to obtain compound 6-9. [M+1]$^+$=270.34.

Step 8: Synthesis of Compound 6-10

Compound 6-9 (3 g, 11.14 mmol) was added to N,N-dimethylformamide (30 mL), then 1-hydroxybenzotriazole (6.02 g, 44.55 mmol) and hydrochloride of 1-(3-dimethyl-aminopropyl)-3-ethylcarbodiimide (5.80 g, 44.90 mmol, 7.82 mL) were added thereto, and the reaction was stirred at 20° C. for 0.5 hours, then N,N-diisopropylethylamine (6.41 g, 33.42 mmol) and hydrochloride of compound 1-3 (2.13 g, 13.76 mmol) were added thereto, and the reaction mixture was stirred at 20° C. for 20 hours. The reaction mixture was added with 5% citric acid (15 mL), then added with water (40 mL), and extracted with ethyl acetate (40 mL). Then the aqueous phase was extracted with ethyl acetate (30 mL), and the organic phases were combined, washed with saturated brine (30 mL), dried over anhydrous sodium sulfate and concentrated under reduced pressure. The residue was purified by column chromatography (petroleum ether: ethyl acetate=1:1) to obtain compound 6-10. [M+1]$^+$=406.25.

Step 9: Synthesis of Compound 6-11

Compound 6-10 (300.00 mg, 737.98 μmol) was added to a mixture of anhydrous tetrahydrofuran (2.5 mL) and water (1 mL), and then lithium hydroxide monohydrate (61.94 mg, 1.48 mmol) was added to the reaction system, and the reaction mixture was stirred at 20° C. for 16 hours. The reaction mixture was added with ethyl acetate (10 mL), washed with water (10 mL), then the aqueous phase was added with 5% citric acid (2 mL), extracted with ethyl acetate (10 mL×2). The organic phases were combined, washed with saturated brine (10 mL), dried over anhydrous sodium sulfate and concentrated under reduced pressure. Compound 6-11 was obtained from the crude product without further purification. [M+1]$^+$=392.23.

Step 10: Synthesis of Compound 6-12

Compound 6-11 (300.00 mg, 764.35 μmol) was added to 2-butanone (6 mL), then 1-hydroxybenzotriazole (103.28 mg, 764.35 μmol) and hydrochloride of 1-(3-dimethylami-nopropyl)-3-ethylcarbodiimide (175.83 mg, 917.23 μmol) were added thereto, and the reaction mixture was stirred at 20° C. for 0.5 hours. N,N-Diisopropylethylamine (263.43 mg, 2.04 mmol, 355.03 μL) and hydrochloride of compound BB-1 (158.72 mg, 764.35 μmol) were added to the reaction system and the reaction mixture was stirred at 20° C. for 16 hours. The reaction mixture was added with 5% citric acid (5 mL), then added with water (10 mL), and extracted with ethyl acetate (10 mL×2). The aqueous phase was extracted with ethyl acetate (10 mL), and the organic phases were combined, washed with saturated brine (5 mL), dried over anhydrous sodium sulfate and concentrated under reduced pressure. The residue was purified by column chromatography (dichloromethane: anhydrous methanol=10:1) to obtain compound 6-12. [M+1]$^+$=545.32.

Step 11: Synthesis of Compound 6-13

Compound 6-12 (0.1 g, 183.26 μmol) was dissolved in dichloromethane (1 mL), then trifluoroacetic acid (41.79 mg, 366.52 μmol, 27.14 μL) was added thereto, and the reaction mixture was stirred at 20° C. for 1 hour. The reaction mixture was then evaporated to dryness by rotary evaporation, added with dichloromethane and concentrated under reduced pressure, and the above steps were repeated for three times, then the concentrated solid was dissolved in anhydrous methanol (5 mL). Methyl trifluoroacetate (1.44 g, 11.22 mmol, 1.13 mL) was added to the reaction system, and triethylamine (681.33 mg, 6.73 mmol, 937.17 μL) was added thereto. The reaction mixture was stirred at 38° C. for 12 hours. The reaction mixture was directly concentrated under reduced pressure, and purified by column chromatography (petroleum ether: ethyl acetate=1:1) to obtain compound 6-13. [M+1]$^+$=541.25.

Step 12: Synthesis of Compound 6

Compound 6-13 (0.1 g, 184.65 μmol) was dissolved in dichloromethane (1 mL), then methyl N-(triethylammonio-sulfonyl)carbamate (110.01 mg, 461.63 μmol) was added thereto, and the reaction mixture was stirred at 25° C. for 16 hours, then dichloromethane (10 mL) was added to the reaction mixture, and saturated sodium bicarbonate solution (5 mL) was added thereto for extraction to separate the phases, and the organic phase was added with saturated brine (5 mL) to separate the phases, and then the organic phase was dried over sodium sulfate and concentrated under reduced pressure to obtain a crude product, and the crude product was separated by preparative HPLC (column type: C18 100*30 mm*10 μm; mobile phase: [H$_2$O (NH$_4$HCO$_3$)-ACN]; ACN %: 40%-60%, 8 min) to obtain a crude product. The crude product was separated by SFC analysis method: column type: Chiralpak AD-3, 150×4.6 mm I.D., 3 M, mobile phase: A: CO$_2$, B: EtOH (0.1% IPAm, v/v), gradient: time A % B %, 0.0-0.5 min, B % from 10% to 50%, maintained for 4.5 min, 4.5-5.0 min, B % from 50% to 10%, flow rate: 2.5 mL/min, column temperature: 35° C., ABPR: 2000 psi. The retention time of compound 6A was 1.97 minutes, and the retention time of compound 6 was 2.28 minutes. The crude product was separated by SFC (column type: DAICEL CHIRALPAK AD (250 mm*30 mm, 10 M); mobile phase: [0.1% NH$_3$H$_2$O-EtOH]%: 16%-16%, 10 min) to obtain compound 6. $^1$H NMR (400 MHz, CDCl$_3$) δ=7.22-7.17 (m, 1H), 4.88-4.79 (m, 1H), 4.75-4.67 (m, 1H), 4.38-4.33 (m, 1H), 3.53-3.32 (m, 2H), 2.93-2.84 (m, 1H), 2.71-2.58 (m, 1H), 2.33-2.05 (m, 3H), 2.04-1.74 (m, 16H), 1.72-1.60 (m, 2H), 1.57-1.41 (m, 3H).

Embodiment 7
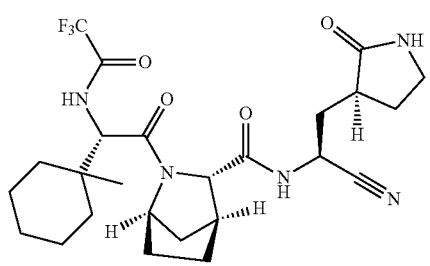
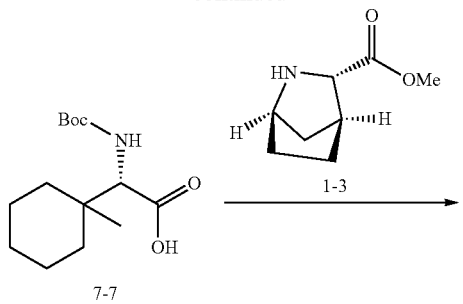
7-7
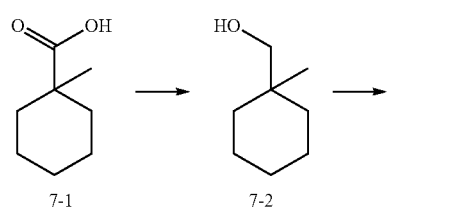
7-1    7-2
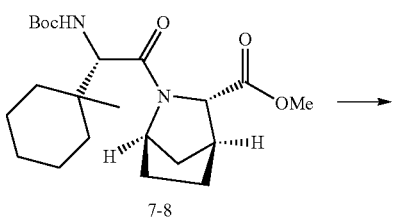
7-8
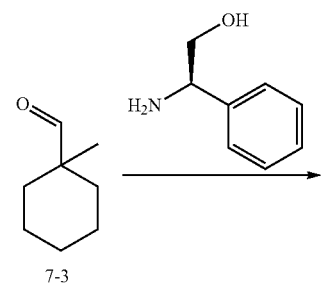
7-3
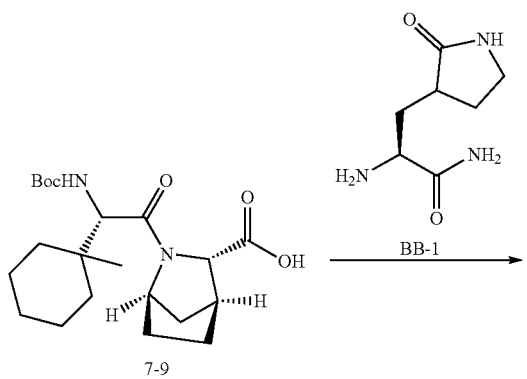
7-9
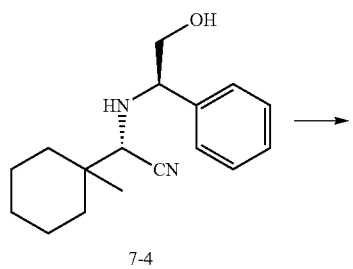
7-4
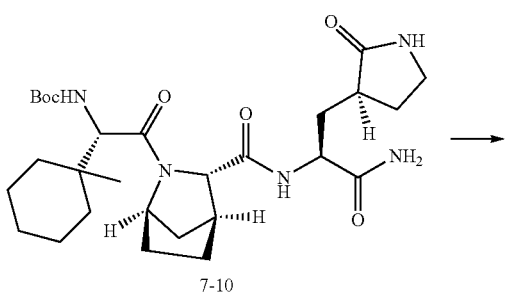
7-10
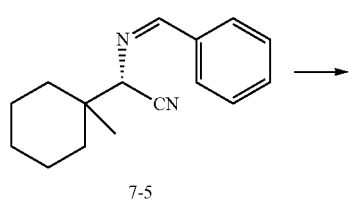
7-5
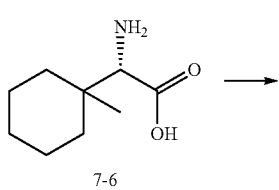
7-6
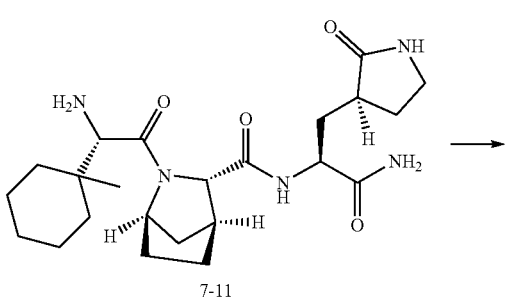
7-11

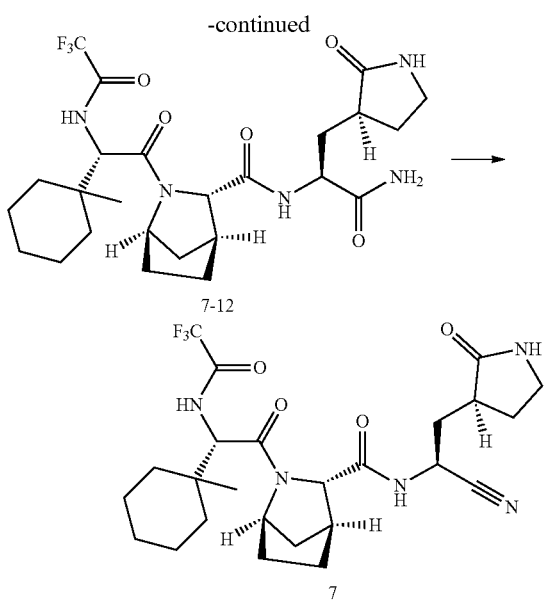

Step 1: Synthesis of Compound 7-2

Compound 7-1 (5 g, 35.16 mmol) was dissolved in tetrahydrofuran (50 mL), and the reaction system was replaced with nitrogen for three times, cooled to 0° C., and a solution of borane in tetrahydrofuran (70.33 mL, 1 M) was slowly added dropwise thereto. The reaction was stirred for 16 hours at 20° C. Sodium hydroxide solution (80 mL, 1 M) was added to the reaction at 0° C., extracted twice with methyl tert-butyl ether (100 mL), and the organic phases were combined and washed with 10% citric acid (80 mL×2) and saturated brine (80 mL), dried over anhydrous sodium sulfate, filtered and concentrated. Compound 7-2 was obtained. $^1$H NMR (400 MHz, CDCl$_3$) δ ppm 3.28 (s, 2H) 1.22-1.46 (m, 10H) 0.85-0.87 (m, 3H).

Step 2: Synthesis of Compound 7-3

Compound 7-2 (4 g, 31.20 mmol) was dissolved in acetonitrile (40 mL), and 2-iodobenzoic acid (13.10 g, 46.80 mmol) was added to the reaction system. The reaction was stirred at 50° C. for 16 hours. The reaction system was filtered and the filtrate was used directly in the next reaction without purification to obtain a solution of compound 7-3 in acetonitrile.

Step 3: Synthesis of Compound 7-4

The solution of compound 7-3 (4 g, 31.37 mmol) in acetonitrile was dissolved in methanol (60 mL), and the compound R-phenylglycinol (5.22 g, 38.04 mmol) was added to the reaction system, and the reaction mixture was stirred at 20° C. for 2 hours. The reaction system was cooled to 0° C., and trimethylsilyl cyanide (22.01 g, 221.88 mmol) was added thereto, and the reaction mixture was stirred at 50° C. for 16 hours. The reaction mixture was directly evaporated to dryness by rotary evaporation. The residue was purified by silica gel column chromatography (petroleum ether: ethyl acetate=3:1) to obtain compound 7-4. [M+1]$^+$=273.3. $^1$H NMR (400 MHz, CDCl$_3$) δ=7.42-7.29 (m, 5H), 4.17-4.01 (m, 1H), 3.99-3.68 (m, 2H), 3.58-3.39 (m, 1H), 1.60-1.16 (m, 10H), 1.10-1.04 (m, 3H).

Step 4: Synthesis of Compound 7-5

Compound 7-4 (5 g, 18.36 mmol) was dissolved in methanol (50 mL) and dichloromethane (50 mL), cooled to 0° C., and lead tetraacetate (13.56 g, 27.53 mmol) was added thereto, and the reaction was stirred at 0° C. for 15 minutes. The reaction mixture was poured into saturated sodium bicarbonate solution (45 mL), extracted three times with dichloromethane (45 mL). The organic phase was dried over anhydrous sodium sulfate, filtered, and concentrated under reduced pressure to obtain a crude product. Compound 7-5 was obtained. [M+1]$^+$=241.2.

Step 5: Synthesis of Hydrochloride of Compound 7-6

Compound 7-5 (3 g, 12.48 mmol) was dissolved in 6M hydrochloric acid (300 mL), heated to 100° C., and the reaction mixture was stirred for 24 hours. The reaction system was extracted three times with chloroform (300 mL), and the aqueous phase was taken and concentrated under reduced pressure. Hydrochloride of compound 7-6 was obtained. $^1$H NMR (400 MHz, CD$_3$OD) δ=4.47 (s, 1H), 1.66-1.42 (m, 10H), 1.22-1.14 (m, 3H).

Step 6: Synthesis of Compound 7-7

Hydrochloride of compound 7-6 (1 g, 5.84 mmol) was dissolved in tetrahydrofuran (10 mL) and water (10 mL), then anhydrous potassium carbonate (2.42 g, 17.52 mmol) and di-tert-butyl dicarbonate (2.55 g, 11.68 mmol) were added thereto, and the reaction was stirred at 20° C. for 16 hours. The pH of reaction mixture was adjusted to 3 with 1 M KHSO$_4$, and the mixture was extracted four times with dichloromethane (40 mL), then the organic phase was dried over anhydrous sodium sulfate, filtered, and concentrated under reduced pressure. Compound 7-7 was obtained. [M−1]$^-$=270.3.

Step 7: Synthesis of Compound 7-8

Compound 7-7 (350 mg, 1.29 mmol) was dissolved in N,N-dimethylformamide (4 mL), and 2-(7-azabenzotriazol-1-yl)-N,N,N',N'-tetramethyluronium hexafluorophosphate (735.65 mg, 1.93 mmol) was added thereto, and the reaction mixture was stirred at 20° C. for 0.5 hours. N,N-Diisopropylethylamine (833.51 mg, 6.45 mmol) and hydrochloride of compound 1-3 (260.23 mg, 1.68 mmol) were added thereto, then the reaction was stirred at 20° C. for 16 hours. The reaction mixture was added with water (10 mL), extracted twice with ethyl acetate (20 mL), and the organic phases were combined, washed twice with 5% citric acid (15 mL), and washed four times with brine (10 mL), dried over anhydrous sodium sulfate, filtered, and evaporated to dryness by rotary evaporation. The residue was purified by column chromatography (petroleum ether: ethyl acetate=5:1) to obtain compound 7-8. [M+1]$^+$=409.4.

Step 8: Synthesis of Compound 7-9

Compound 7-8 (120 mg, 293.74 μmol) was dissolved in tetrahydrofuran (6 mL), methanol (2 mL) and water (2 mL), then lithium hydroxide monohydrate (36.98 mg, 881.21 μmol) was added thereto and the reaction mixture was stirred at 20° C. for 16 hours. The reaction mixture was added with 3% citric acid (20 mL), extracted twice with ethyl acetate (20 mL), and the organic phases were combined, washed with saturated brine (20 mL), dried over anhydrous sodium sulfate, filtered and evaporated to dryness by rotary evaporation to obtain compound 7-9. [M+1]$^+$=391.3.

Step 9: Synthesis of Compound 7-10

Compound 7-9 (30 mg, 76.04 μmol) was dissolved in N,N-dimethylformamide (2 mL), then 1-hydroxybenzotriazole (10.28 mg, 76.04 μmol) and hydrochloride of 1-(3-dimethylaminopropyl)-3-ethylcarbodiimide (17.49 mg, 91.25 μmol) were added thereto, and the reaction mixture was stirred at 20° C. for 0.5 hours. N,N-Diisopropylethylamine (39.31 mg, 304.18 μmol) and hydrochloride of compound BB-1 (19.53 mg, 114.07 μmol) were added thereto, then the reaction was stirred at 20° C. for 16 hours. The reaction mixture was added with water (10 mL), extracted twice with dichloromethane (20 mL), and the organic phases were combined and washed twice with 5% citric acid (15 mL) and washed twice with brine (10 mL), then dried over anhydrous sodium sulfate, filtered, and evaporated to dryness by rotary evaporation. The residue was purified by column chromatography (dichloromethane:methanol=20:1) to obtain compound 7-10. [M+1]$^+$=548.4.

Step 10: Synthesis of Trifluoroacetate of Compound 7-11

Compound 7-10 (150 mg, 273.88 μmol) was dissolved in dichloromethane (3 mL) and trifluoroacetic acid (1 mL), and the reaction was stirred at 20° C. for 2 hours. The reaction was directly evaporated to dryness by rotary evaporation by an oil pump, added with dichloromethane and evaporated by rotary evaporation, and the above steps were repeated. Trifluoroacetate of compound 7-11 was obtained.

Step 11: Synthesis of Compound 7-12

Trifluoroacetate of compound 7-11 (120 mg, 268.11 μmol) was dissolved in methanol (2 mL), then triethylamine (162.78 mg, 1.61 mmol) and methyl trifluoroacetate (343.32 mg, 2.68 mmol) were added thereto. The reaction was heated to 38° C. and stirred for 16 hours. The reaction system was directly concentrated under reduced pressure, then dissolved in water (10 mL) and ethyl acetate (20 mL), and the pH was adjusted to acidic with 3% citric acid (10 mL), then the mixture was extracted for three times with ethyl acetate (20 mL), and then washed twice with saturated brine (10 mL), dried over anhydrous sodium sulfate, filtered, and concentrated. Compound 7-12 was obtained. [M+1]$^+$=544.3.

Step 12: Synthesis of Compound 7

Compound 7-12 (130 mg, 239.16 μmol) was dissolved in dichloromethane (4 mL), then tetrahydrofuran (0.4 mL) and Burgess reagent (142.48 mg, 597.89 μmol) were added thereto and the reaction mixture was stirred at 25° C. for 2 hours. The reaction system was added with dichloromethane (10 mL), washed with saturated sodium bicarbonate (5 mL) and then washed with saturated brine (5 mL) to obtain the organic phase, and the organic phase was dried over anhydrous sodium sulfate, filtered and concentrated under reduced pressure. The crude product was separated by preparative HPLC (column type: C18 100*30 mm*10 μm; mobile phase: [water (NH$_4$HCO$_3$)-ACN]; ACN %: 35%-55%, 8 min) to obtain compound 7. $^1$H NMR (400 MHz, CDCl$_3$) δ=4.92-4.81 (m, 1H), 4.78-4.63 (m, 1H), 4.60 (br s, 1H), 3.50-3.34 (m, 2H), 2.93-2.79 (m, 1H), 2.30 (br s, 2H), 2.10 (br s, 2H), 1.94-1.86 (m, 1H), 1.75 (br s, 2H), 1.71-1.60 (m, 4H), 1.33 (br d, J=16.5 Hz, 10H), 1.30-1.17 (m, 1H), 1.16-0.96 (m, 3H).

Embodiment 8

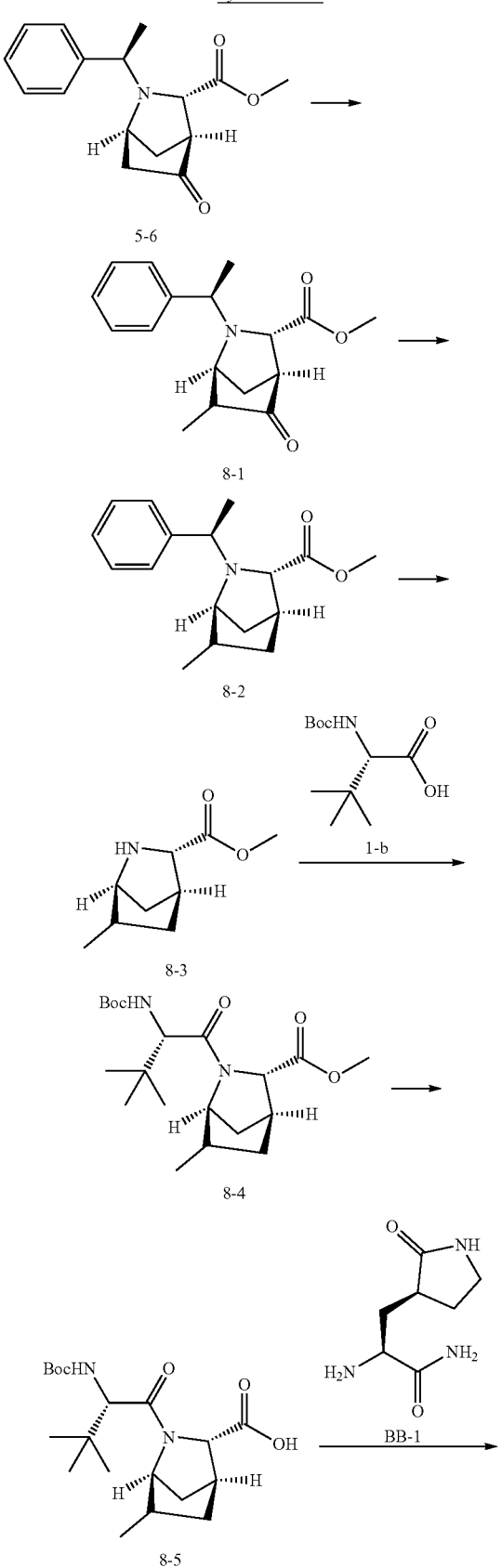

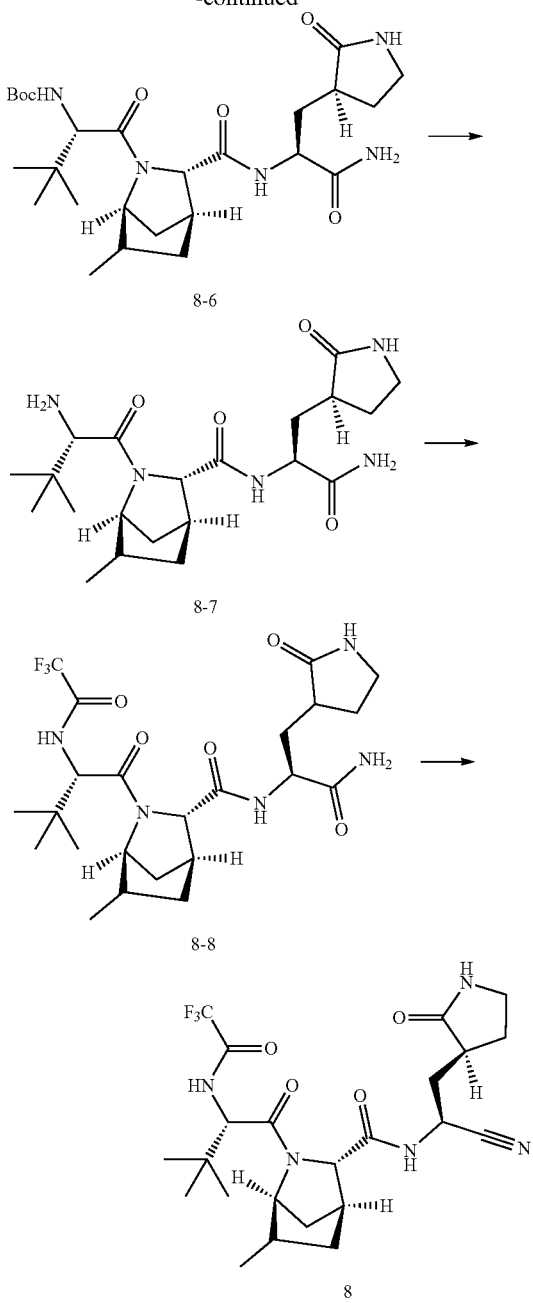

Step 1: Synthesis of Compound 8-1

Compound 5-6 (2 g, 7.32 mmol) was dissolved in tetrahydrofuran (20 mL), and the reaction system was replaced with nitrogen for three times, cooled to −70° C., then lithium diisopropylamide (2 M, 7.32 mL) was slowly added dropwise thereto, and the reaction mixture was reacted for 1 hour. Subsequently, at −70° C., methyl iodide (2.60 g, 73.17 mmol, 4.56 mL) was slowly added dropwise, slowly raised to 20° C., and the reaction was continued for 1 hour. Under nitrogen atmosphere, the reaction system was slowly added dropwise with saturated ammonium chloride solution (100 mL) for quenching the reaction, then extracted twice with ethyl acetate (200 mL), and the organic phases were combined, dried over anhydrous sodium sulfate, filtered, concentrated. The residue was purified by silica gel column chromatography (petroleum ether: ethyl acetate=1:0 to 10:1) to obtain compound 8-1. $^1$H NMR (400 MHz, CDCl$_3$) δ=7.34-7.27 (m, 3H), 7.26-7.18 (m, 2H), 3.87-3.77 (m, 1H), 3.67-3.59 (m, 1H), 3.25 (s, 3H), 2.96 (s, 1H), 2.67-2.64 (m, 1H), 2.64-2.55 (m, 2H), 1.94 (d, J=10.7 Hz, 1H), 1.43 (d, J=6.5 Hz, 3H), 1.14-1.09 (m, 3H).

Step 2: Synthesis of Compound 8-2

Compound 8-1 (600 mg, 2.09 mmol) was dissolved in N,N-dimethylformamide (6 mL), then p-toluenesulfonyl hydrazide (466.62 mg, 2.51 mmol) and trifluoromethanesulfonic acid (36.69 mg, 239.58 mol, 21.58 μL) were added thereto, heated to 100° C., then sodium cyanoborohydride (393.65 mg, 6.26 mmol) was added, and the reaction mixture was reacted for 2 hours. The reaction system was added with ethyl acetate (60 mL), washed with saturated sodium bicarbonate solution (30 mL) and saturated brine (30 mL) in turn to separate the organic phase, and the organic phase was dried over anhydrous sodium sulfate, filtered, and concentrated. The residue was purified by silica gel column chromatography (petroleum ether: ethyl acetate=1:0 to 10:1) to obtain compound 8-2. $^1$H NMR (400 MHz, CDCl$_3$) δ=7.37-7.29 (m, 2H), 7.25 (br d, J=7.1 Hz, 3H), 3.67-3.50 (m, 1H), 3.48-3.34 (m, 1H), 3.32-3.15 (m, 3H), 2.51 (s, 1H), 2.35-2.23 (m, 2H), 2.02-1.94 (m, 1H), 1.70-1.61 (m, 1H), 1.46-1.41 (m, 1H), 1.36 (d, J=6.5 Hz, 3H), 1.18-1.10 (m, 1H), 0.96 (d, J=7.1 Hz, 3H).

Step 3: Synthesis of Hydrochloride of Compound 8-3

Compound 8-2 (150 mg, 548.71 μmol) was dissolved in ethanol (4 mL), then 12 M hydrochloric acid (137.18 μL) and wet palladium on carbon (0.5 g, palladium content of 10%) were added thereto, and the reaction mixture was reacted under a hydrogen balloon atmosphere at 15 psi and 20° C. for 16 hours. The reaction system was filtered through diatomite and evaporated to dryness by rotary evaporation to obtain hydrochloride of compound 8-3. [M+1]$^+$=170.1.

Step 4: Synthesis of Compound 8-4

Compound 1-b (114.81 mg, 496.39 μmol) was dissolved in N,N-dimethylformamide (2 mL), then O-(7-azabenzotriazol-1-yl)-N,N,N,N-tetramethyluronium hexafluorophosphate (235.93 mg, 620.49 μmol) and diisopropylethylamine (267.31 mg, 2.07 mmol, 360.26 μL) were added thereto, and the reaction mixture was stirred for 30 min, then hydrochloride of compound 8-3 (70 mg) was added thereto, and the reaction mixture was stirred continuously at 20° C. for 2.5 hours. The reaction system was added with ethyl acetate (40 mL), then extracted with 3% citric acid solution (30 mL) and saturated sodium bicarbonate solution (20 mL) in turn to separate the organic phase, and extracted with saturated brine (20 mL) to separate the organic phase, and the organic phase was dried over anhydrous sodium sulfate and concentrated under reduced pressure to obtain compound 8-4. [M+1]$^+$=383.3.

Step 5: Synthesis of Compound 8-5

Compound 8-4 (125 mg, 326.80 μmol) was dissolved in a mixed solvent of tetrahydrofuran (3 mL), water (1 mL) and methanol (1 mL), and lithium hydroxide monohydrate (41.14 mg, 980.41 μmol) was added thereto, and the reaction mixture was reacted at 30° C. for 16 hours. The reaction system was added with dichloromethane (40 mL) and 3% citric acid (20 mL) for extraction to separate the organic phase. Then, saturated brine (20 mL) was added for extraction to separate the organic phase, and the organic phase was dried over anhydrous sodium sulfate, and concentrated under reduced pressure to obtain compound 8-5. [M+1]$^+$=369.3.

Step 6: Synthesis of Compound 8-6

Compound 8-5 (115 mg, 312.10 μmol) was dissolved in N,N-dimethylformamide (2 mL), then 1-hydroxybenzotriazole (50.61 mg, 374.53 μmol) and hydrochloride of 1-(3-dimethylaminopropyl)-3-ethylcarbodiimide (89.75 mg, 468.16 μmol) were added thereto, stirred for 30 min, then diisopropylethylamine (161.35 mg, 1.25 mmol, 217.45 μL) and hydrochloride of BB-1 (64.12 mg, 374.53 mol) were added thereto and the reaction mixture was reacted at 20° C. for 2 hours. The reaction system was added with ethyl acetate (50 mL) and 3% citric acid (25 mL) for extraction to separate the organic phase, and the organic phase was extracted with saturated brine (25 mL) to separate the organic phase, and the organic phase was dried over anhydrous sodium sulfate, and concentrated under reduce pressure. The residue was purified by silica gel chromatography (dichloromethane:methanol=1:0 to 30:1) to obtain compound 8-6. $[M+1]^+=522.4$.

Step 7: Synthesis of Trifluoroacetate of Compound 8-7

Compound 8-6 (240 mg, 460.08 μmol, 1 eq) was dissolved in dichloromethane (1 mL), then trifluoroacetic acid (0.3 mL) was added thereto, and the reaction mixture was reacted at 20° C. for 1 hour. The reaction system was directly concentrated under reduced pressure to obtain trifluoroacetate of compound 8-7. $[M+1]^+=422.3$.

Step 8: Synthesis of Compound 8-8

Trifluoroacetate of compound 8-7 (180 mg, 427.01 μmol) was dissolved in methanol (2 mL), then triethylamine (172.84 mg, 1.71 mmol, 237.74 μL) and methyl trifluoroacetate (546.79 mg, 4.27 mmol, 430.54 μL) were added thereto and the reaction mixture was reacted for 3 hours at 38° C. The reaction system was concentrated under reduced pressure, then dissolved with water (10 mL) and ethyl acetate (30 mL×2). The pH was adjusted to acidic with 3% citric acid (5 mL), and the mixture was extracted to separate the organic phase, and the organic phase was washed with saturated brine (15 mL), dried and concentrated to obtain compound 8-8. $[M+1]^+=518.3$.

Step 9: Synthesis of Compound 8

Compound 8-8 (200 mg, 386.44 μmol) was dissolved in dichloromethane (2 mL), and Burgess reagent (230.23 mg, 966.11 μmol) was added thereto, and the reaction mixture was stirred at 25° C. for 16 hours. $^1$H NMR (400 MHz, CD$_3$OD) δ=5.07-4.99 (m, 2H), 4.79-4.71 (m, 1H), 4.29-4.18 (m, 1H), 3.83-3.74 (m, 1H), 3.28-3.23 (m, 1H), 2.76-2.65 (m, 1H), 2.63-2.57 (m, 1H), 2.38-2.26 (m, 2H), 2.19-2.10 (m, 1H), 2.02-1.95 (m, 1H), 1.90-1.75 (m, 3H), 1.67-1.60 (m, 1H), 1.33-1.26 (m, 1H), 1.15-1.04 (m, 9H), 0.99 (d, J=7.1 Hz, 3H). $[M+1]^+=500.3$.

Embodiment 9

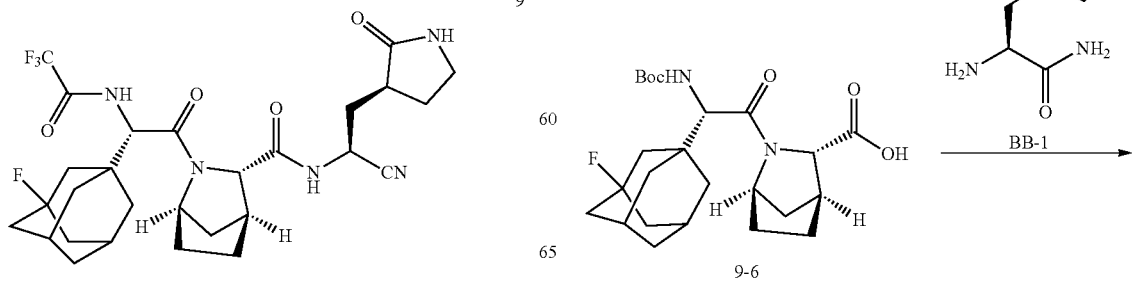

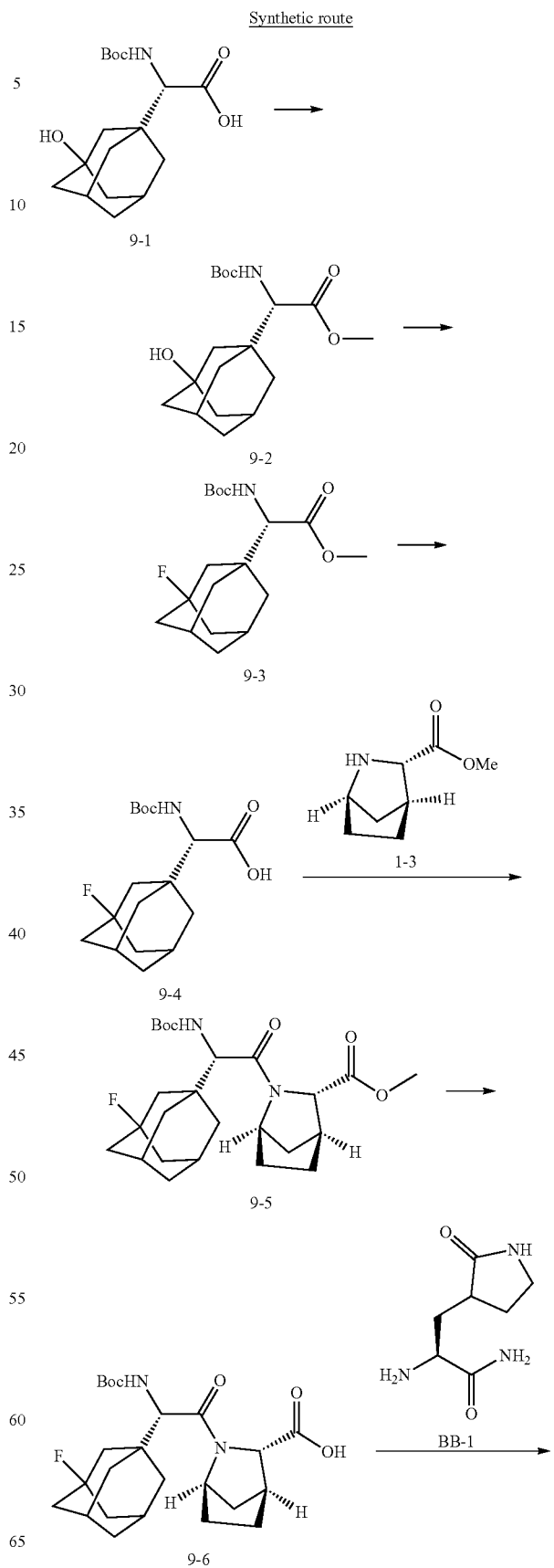

Synthetic route

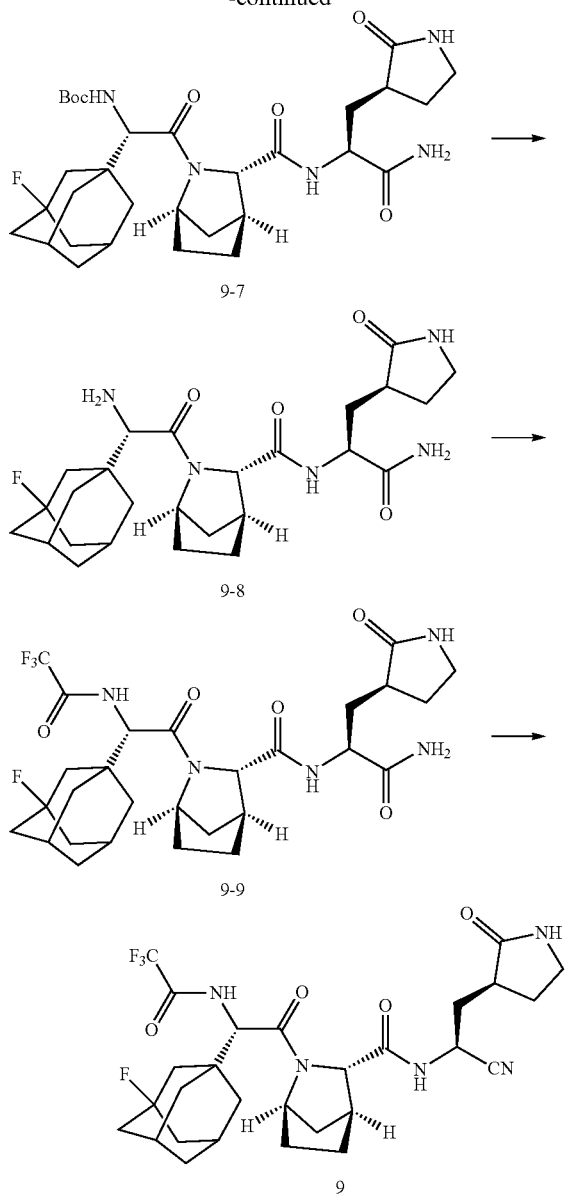

Step 1: Synthesis of Compound 9-2

Compound 9-1 (2 g, 6.15 mmol) was dissolved in methanol (8 mL) and toluene (24 mL), and cooled to 0° C., and a solution of (trimethylsilyl)diazomethane (6.15 mL, 2 M) in n-hexane was slowly added dropwise thereto. The reaction was stirred for 16 hours at 20° C. The reaction mixture was directly evaporated to dryness by rotary evaporation, and then purified by column chromatography (petroleum ether: ethyl acetate=3:1) to obtain compound 9-2. $^1$H NMR (400 MHz, CDCl$_3$) δ=5.15-5.07 (m, 1H), 3.74 (s, 3H), 2.25 (br s, 1H), 1.72-1.41 (m, 23H). [M−99]$^+$=240.2.

Step 2: Synthesis of Compound 9-3

Compound 9-2 (100 mg, 294.62 μmol) was dissolved in dichloromethane (1 mL), cooled to 0° C., and diethylaminosulfur trifluoride (94.98 mg, 589.23 μmol) was added to the reaction system. The reaction was stirred at 20° C. for 16 hours. The reaction mixture was slowly added to saturated sodium bicarbonate solution (20 mL) at 0° C., and extracted twice with dichloromethane (20 mL). The combined organic phases were dried over anhydrous sodium sulfate, filtered, and concentrated to obtain compound 9-3. $^1$H NMR (400 MHz, CDCl$_3$) δ=5.20-4.99 (m, 1H), 3.75 (s, 3H), 2.32 (br s, 1H), 1.88-1.43 (m, 23H). [M−55]$^+$=286.1.

Step 3: Synthesis of Compound 9-4

Compound 9-3 (700 mg, 2.05 mmol) was dissolved in tetrahydrofuran (7 mL), water (2.3 mL) and methanol (2.3 mL), then lithium hydroxide monohydrate (430.19 mg, 10.25 mmol) was added thereto and the reaction mixture was stirred at 20° C. for 16 hours. The reaction mixture was added with water (10 mL) and 5% citric acid (15 mL), extracted twice with ethyl acetate (15 mL), and the organic phases were combined, washed with saturated brine (15 mL), dried over anhydrous sodium sulfate, filtered and evaporated to dryness by rotary evaporation. Compound 9-4 was obtained without purification. $^1$H NMR (400 MHz, CDCl$_3$) δ=5.31 (s, 1H), 5.10 (br d, J=9.5 Hz, 1H), 4.20-4.09 (m, 1H), 2.34 (br s, 1H), 1.90-1.75 (m, 7H), 1.58 (br s, 5H), 1.46 (s, 9H). [M−55]$^+$=272.2.

Step 4: Synthesis of Compound 9-5

Compound 9-4 (776 mg, 2.37 mmol) was dissolved in N,N-dimethylformamide (8 mL), then 1-hydroxybenzotriazole (960.83 mg, 7.11 mmol) and hydrochloride of 1-(3-dimethylaminopropyl)-3-ethylcarbodiimide (908.77 mg, 4.74 mmol) were added thereto, and the reaction mixture was stirred at 20° C. for 0.5 hours. N,N-Diisopropylethylamine (919.02 mg, 7.11 mmol) and hydrochloride of compound 1-3 (367.85 mg, 2.37 mmol) were added thereto, and the reaction was stirred at 20° C. for 16 hours. The reaction mixture was added with water (15 mL), extracted twice with ethyl acetate (30 mL), and the organic phases were combined, washed twice with 5% citric acid (30 mL), and washed four times with brine (20 mL), dried over anhydrous sodium sulfate, filtered, and evaporated to dryness by rotary evaporation. The residue was purified by column chromatography (petroleum ether: ethyl acetate=8:1) to obtain compound 9-5. $^1$H NMR (400 MHz, CDCl$_3$) δ=5.32-5.21 (m, 1H), 4.49 (br s, 1H), 4.32 (br d, J=9.8 Hz, 1H), 4.07 (s, 1H), 3.73 (s, 3H), 2.75 (br s, 1H), 2.33 (br s, 1H), 1.89-1.53 (m, 18H), 1.44 (s, 9H). [M+1]$^+$=465.3.

Step 5: Synthesis of Compound 9-6

Compound 9-5 (740 mg, 1.59 mmol) was dissolved in tetrahydrofuran (7.4 mL), water (2.47 mL) and methanol (2.47 mL), then lithium hydroxide monohydrate (200.51 mg, 4.78 mmol) was added thereto and the reaction mixture was stirred at 20° C. for 16 hours. The reaction mixture was added with water (20 mL) and 5% citric acid (25 mL), extracted twice with ethyl acetate (40 mL), and the organic phases were combined, washed with saturated brine (40 mL), dried over anhydrous sodium sulfate, filtered and evaporated to dryness by rotary evaporation. Compound 9-6 was obtained without purification. $^1$H NMR (400 MHz, CDCl$_3$) δ=5.30 (br d, J=9.8 Hz, 1H), 4.48 (br s, 1H), 4.36 (br d, J=9.9 Hz, 1H), 4.14 (s, 1H), 2.97 (br s, 1H), 2.31 (br s, 1H), 2.01-1.50 (m, 19H), 1.44 (s, 9H). [M−55]$^+$=395.2.

Step 6: Synthesis of Compound 9-7

Compound 9-6 (710 mg, 1.58 mmol) was dissolved in 2-butanone (7 mL), then 1-hydroxybenzotriazole (255.52 mg, 1.89 mmol) and hydrochloride of 1-(3-dimethylaminopropyl)-3-ethylcarbodiimide (453.14 mg, 2.36 mmol) were added thereto, and the reaction mixture was stirred at 20° C. for 0.5 hours. N,N-diisopropylethylamine (814.67 mg, 6.30 mmol) and hydrochloride of compound BB-1 (323.74 mg, 1.89 mmol) were added thereto and the reaction was stirred at 20° C. for 16 hours. The reaction mixture was added with water (15 mL), extracted twice with ethyl acetate (30 mL), and the organic phases were combined, washed twice with 5% citric acid (30 mL), and washed four times with brine (20 mL), dried over anhydrous sodium sulfate, filtered, and evaporated to dryness by rotary evaporation. The residue was purified by column chromatography (dichloromethane:methanol=20:1) to obtain compound 9-7. $^1$H NMR (400 MHz, CDCl$_3$) δ=7.96 (br d, J=6.3 Hz, 1H), 5.83-5.74 (m, 1H), 5.57-5.44 (m, 1H), 5.25 (br d, J=9.9 Hz, 1H), 4.54-4.48 (m, 1H), 4.37 (br d, J=9.9 Hz, 1H), 4.05-3.97 (m, 1H), 3.43-3.27 (m, 2H), 2.95-2.76 (m, 1H), 2.60-1.30 (m, 34H). [M+1]$^+$=604.4.

Step 7: Synthesis of Trifluoroacetate of Compound 9-8

Compound 9-7 (760 mg, 1.26 mmol) was dissolved in dichloromethane (7.6 mL) and trifluoroacetic acid (2.7 mL), and the reaction was stirred at 20° C. for 2 hours. The reaction was directly evaporated to dryness by rotary evaporation by an oil pump, added with dichloromethane and evaporated by rotary evaporation, and the above steps were repeated. Trifluoroacetate of compound 9-8 was obtained. [M+1]$^+$=504.4.

Step 8: Synthesis of Compound 9-9

Trifluoroacetate of compound 9-8 (300 mg, 595.70 μmol) was dissolved in methanol (6 mL), then triethylamine (241.12 mg, 2.38 mmol) and methyl trifluoroacetate (762.79 mg, 5.96 mmol) were added thereto. The reaction was heated to 38° C. and stirred for 16 hours. The reaction mixture was dried directly and dissolved by adding water (10 mL) and ethyl acetate (10 mL), and the pH of the solution was adjusted to acidic by adding 5% citric acid (10 mL). The phases were separated, extracted twice with ethyl acetate (10 mL), and the organic phases were combined and washed twice with saturated brine (10 mL), dried over anhydrous sodium sulfate, filtered, and concentrated to obtain compound 9-9 without purification. [M+1]$^+$=600.3.

Step 9: Synthesis of Compound 9

Compound 9-9 was dissolved in dichloromethane (2.8 mL), and then Burgess reagent (278.20 mg, 1.17 mmol) was added thereto. The reaction was heated to 25° C. and stirred for 2 hours. The reaction mixture was added with sodium bicarbonate solution (10 mL) and saturated brine (5 mL), extracted twice with dichloromethane (15 mL), and the organic phases were combined, dried over anhydrous sodium sulfate, filtered, and concentrated. The crude product was separated by preparative HPLC (column type: C18 100*30 mm*10 μm; mobile phase: [water (NH$_4$HCO$_3$)-ACN]; ACN %: 35%-55%, 8 min) to obtain compound 9. $^1$H NMR (400 MHz, CDCl$_3$) δ=9.50-8.17 (m, 1H), 7.12-6.93 (m, 1H), 5.92-5.73 (m, 1H), 4.95-4.77 (m, 1H), 4.72-4.57 (m, 1H), 4.46 (s, 1H), 3.97-3.86 (m, 1H), 3.38 (br dd, J=4.0, 8.9 Hz, 1H), 2.87-2.78 (m, 1H), 2.63-1.22 (m, 26H). [M+1]$^+$=582.3.

Embodiment 10

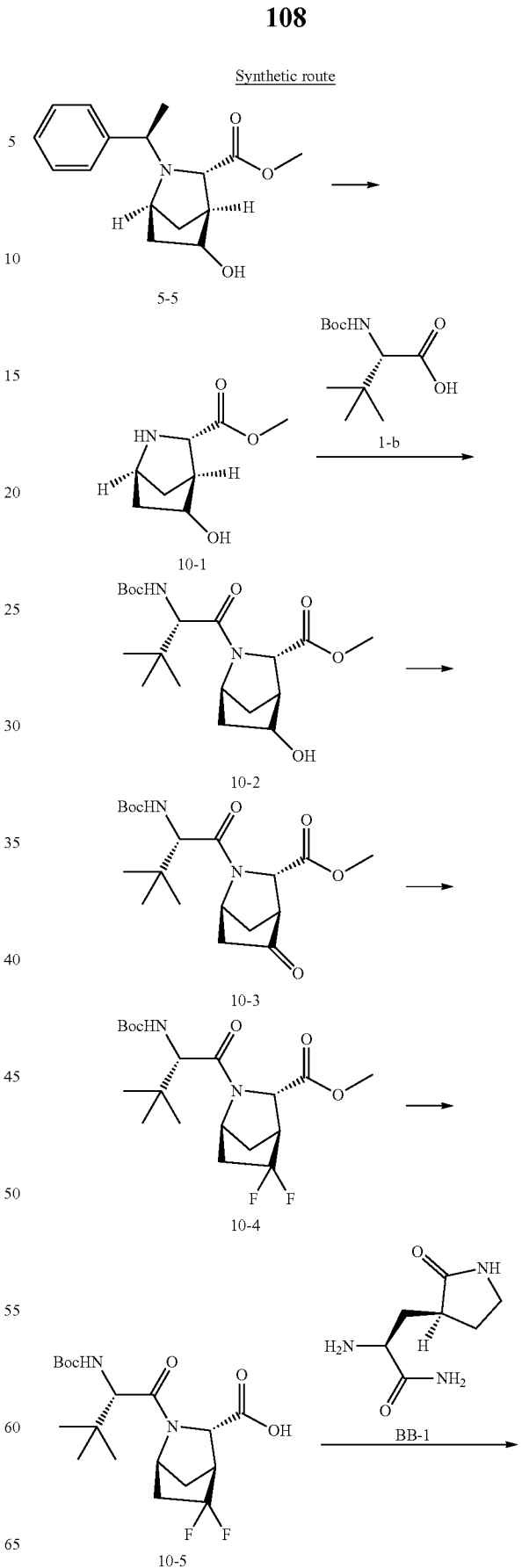

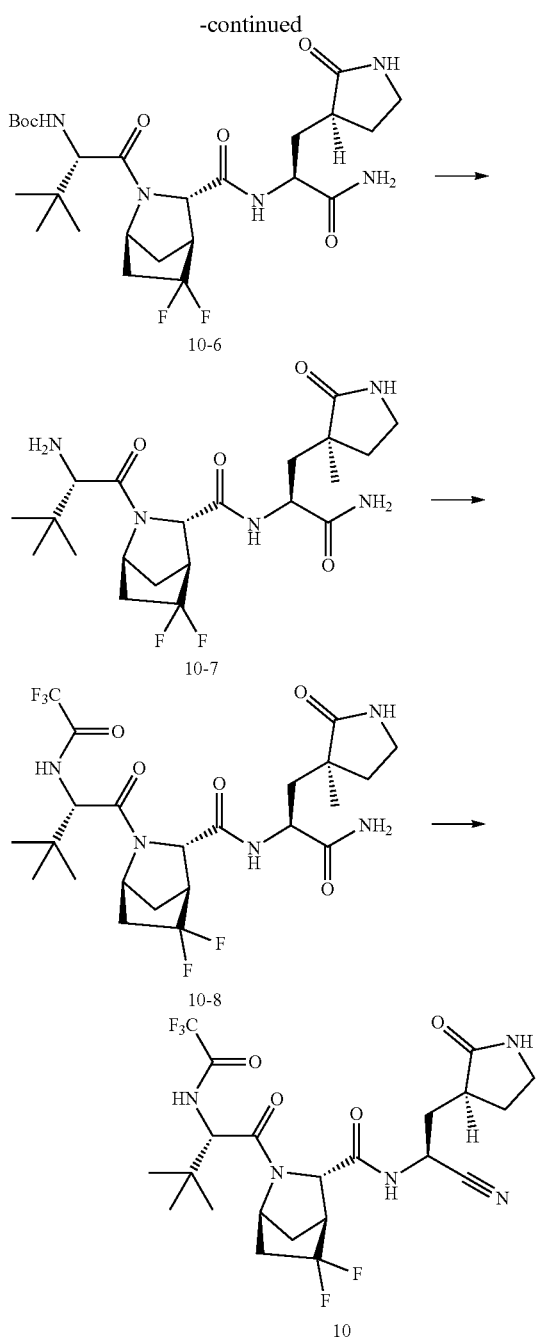

Step 1: Synthesis of Hydrochloride of Compound 10-1

Compound 5-5 (3 g, 10.90 mmol) was dissolved in ethanol (80 mL), then hydrochloric acid (1.19 g, 32.69 mmol) and wet palladium on carbon (15 g, 10.68 mmol) were added thereto. The reaction was stirred at 20° C. for 16 hours. The reaction mixture was filtered through diatomite and directly evaporated to dryness by rotary evaporation to obtain a crude product of hydrochloride of compound 10-1. $[M+1]^+=172.0$.

Step 2: Synthesis of Compound 10-2

Compound 1-b (1.87 g, 10.90 mmol) was dissolved in N,N-dimethylformamide (20 mL), then O-(7-azabenzotriazol-1-yl)-N,N,N,N-tetramethyluronium hexafluorophosphate (4.78 g, 12.58 mmol) and diisopropylethylamine (4.34 g, 33.55 mmol) were added thereto, after stirring for 30 min, hydrochloride of compound 10-1 (190 mg, 1.12 mmol) was added thereto. The reaction was stirred at 20° C. for 16 hours. The reaction mixture was added with water (15 mL), extracted twice with ethyl acetate (60 mL), and the organic phases were combined, washed twice with 5% citric acid (30 mL) and washed four times with brine (20 mL), dried over anhydrous sodium sulfate, filtered and evaporated to dryness by rotary evaporation. The residue was purified by column chromatography (petroleum ether: ethyl acetate=3:1) to obtain compound 10-2. $^1$H NMR (400 MHz, CDCl$_3$) δ=5.28-5.16 (m, 1H), 4.50 (br s, 1H), 4.28 (d, J=9.8 Hz, 1H), 3.92 (s, 1H), 3.74 (s, 3H), 2.81 (s, 1H), 2.67 (s, 1H), 2.17 (br dd, J=6.1, 12.7 Hz, 1H), 1.99-1.93 (m, 1H), 1.90-1.84 (m, 1H), 1.59 (br d, J=13.3 Hz, 2H), 1.43 (s, 9H), 1.04 (s, 9H). $[M+1]^+=385.2$.

Step 3: Synthesis of Compound 10-3

Compound 10-2 (500 mg, 1.30 mmol) was dissolved in acetonitrile (7.5 mL), then 2-iodobenzoic acid (976.31 mg, 3.49 mmol) was added thereto, and the reaction mixture was stirred at 60° C. for 16 hours. The reaction mixture was filtered through diatomite and evaporated to dryness by rotary evaporation. Compound 10-3 was obtained without purification. $[M-55]^+=327.1$.

Step 4: Synthesis of Compound 10-4

Compound 10-3 (480 mg, 1.26 mmol) was dissolved in dichloromethane (4.8 mL), cooled to 0° C., and diethylaminosulfur trifluoride (1.01 g, 6.28 mmol) was added thereto, and the reaction mixture was stirred at 20° C. for 16 hours. The reaction mixture was slowly added to saturated sodium bicarbonate solution (20 mL) at 0° C., extracted twice with dichloromethane (20 mL), and the combined organic phases were dried over anhydrous sodium sulfate, filtered, and concentrated. Compound 10-4 was obtained without purification. $[M-100]^+=304.0$.

Step 5: Synthesis of Compound 10-5

Compound 10-4 (475 mg, 1.17 mmol) was dissolved in tetrahydrofuran (5.5 mL), water (1.84 mL) and methanol (1.84 mL), then lithium hydroxide monohydrate (147.84 mg, 3.52 mmol) was added thereto and the reaction mixture was stirred at 20° C. for 16 hours. The reaction mixture was added with water (20 mL) and 5% citric acid (25 mL), extracted twice with ethyl acetate (40 mL), and the organic phases were combined and washed with saturated brine (40 mL), dried over anhydrous sodium sulfate, filtered, and evaporated to dryness by rotary evaporation. Compound 10-5 was obtained without purification. $^1$H NMR (400 MHz, CDCl$_3$) δ=5.18 (br d, J=9.8 Hz, 1H), 4.65-4.53 (m, 2H), 4.31 (d, J=9.9 Hz, 1H), 3.33 (br d, J=7.3 Hz, 1H), 2.55-2.41 (m, 1H), 2.33-2.07 (m, 3H), 1.45 (s, 9H), 1.03 (s, 9H). $[M-55]^+=335.1$.

Step 6: Synthesis of Compound 10-6

Compound 10-5 (200 mg, 512.27 μmol) was dissolved in 2-butanone (2 mL), then 1-hydroxybenzotriazole (83.06 mg, 614.72 μmol) and hydrochloride of 1-(3-dimethylaminopropyl)-3-ethylcarbodiimide (264.83 mg, 2.05 mmol) were added thereto, and the reaction mixture was stirred at 20° C. for 0.5 hours. N,N-Diisopropylethylamine (264.83 mg, 2.05 mmol) and hydrochloride of compound BB-1 (105.24 mg) were added thereto, then the reaction was stirred at 20° C. for 16 hours. The reaction mixture was added with water (15 mL), extracted twice with ethyl acetate (30 mL), and the organic phases were combined, washed twice with 5% citric acid (30 mL) and washed four times with brine (20 mL), dried over anhydrous sodium sulfate, filtered and evaporated to dryness by rotary evaporation. The residue was purified by column chromatography (dichloromethane:methanol=20:1) to obtain compound 10-6. $^1$H NMR (400 MHz, CDCl₃) δ=8.19 (br d, J=6.8 Hz, 1H), 5.78 (br s, 1H), 5.49 (br s, 1H), 5.19 (br d, J=10.0 Hz, 1H), 4.61 (br s, 1H), 4.44 (s, 1H), 4.34 (d, J=10.3 Hz, 1H), 3.38 (br d, J=6.5 Hz, 2H), 3.10 (br d, J=6.5 Hz, 1H), 2.32-2.20 (m, 3H), 2.02-1.82 (m, 6H), 1.44 (s, 9H), 1.05 (s, 9H). [M+1]⁺=544.3.

Step 7: Synthesis of Trifluoroacetate of Compound 10-7

Compound 10-6 (180 mg, 331.12 μmol) was dissolved in dichloromethane (2 mL) and trifluoroacetic acid (0.7 mL), and the reaction was stirred at 20° C. for 2 hours. The reaction was directly dried by an oil pump, added with a small amount of dichloromethane and dried, and the above steps were repeated until the shape of the product was a light yellow foam. Trifluoroacetate of compound 10-7 was obtained. [M+1]⁺=444.3.

Step 8: Synthesis of Compound 10-8

Trifluoroacetate of compound 10-7 (145 mg, 326.95 μmol) was dissolved in methanol (3.2 mL), and then triethylamine (132.34 mg, 1.31 mmol) and methyl trifluoroacetate (418.66 mg, 3.27 mmol) were added thereto. The reaction was heated to 38° C. and stirred for 16 hours. The reaction mixture was directly evaporated to dryness by rotary evaporation, dissolved with water (10 mL) and ethyl acetate (10 mL), and the pH of the solution was adjusted to acidic by adding 5% citric acid (10 mL). The phases were separated, extracted twice with ethyl acetate (10 mL), and the organic phases were combined and washed twice with saturated brine (10 mL), dried over anhydrous sodium sulfate, filtered, concentrated to obtain compound 10-8 without purification. [M+1]⁺=540.3.

Step 9: Synthesis of Compound 10

Compound 10-8 (170 mg, 315.11 μmol) was dissolved in dichloromethane (2.8 mL), and then Burgess reagent (187.73 mg, 787.77 μmol) was added thereto. The reaction was heated to 25° C. and stirred for 2 hours. The reaction mixture was added with sodium bicarbonate solution (10 mL) and saturated brine (5 mL), extracted twice with dichloromethane (15 mL), and the organic phases were combined, dried over anhydrous sodium sulfate, filtered and concentrated. The crude product was separated by preparative HPLC (column type: C18 100*30 mm*10 μm; mobile phase: [H₂O (NH₄HCO₃)-ACN]; ACN %: 35%-55%, 8 min) to obtain compound 10. ¹H NMR (400 MHz, CDCl₃) δ=9.79-8.65 (m, 1H), 7.18-7.01 (m, 1H), 6.34-6.20 (m, 1H), 4.64-4.58 (m, 2H), 4.45-4.37 (m, 1H), 3.44-3.30 (m, 3H), 3.12-3.05 (m, 1H), 2.63-2.47 (m, 3H), 2.40-2.12 (m, 6H), 1.06 (s, 9H). [M+1]⁺=522.3.

Embodiment 11

11

Synthetic route

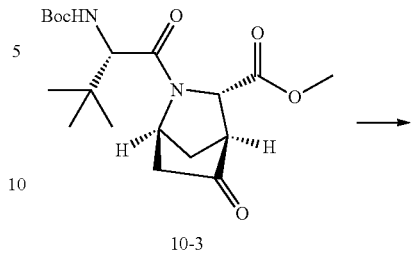

10-3

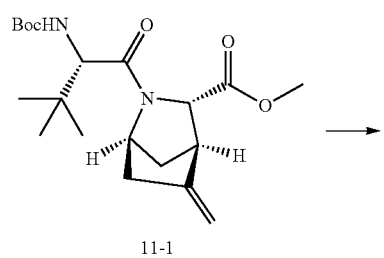

11-1

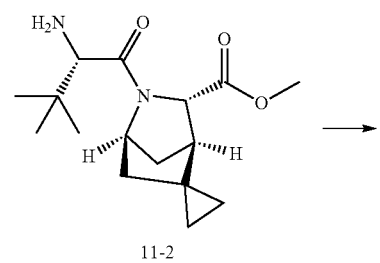

11-2

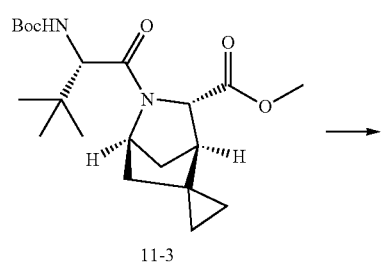

11-3

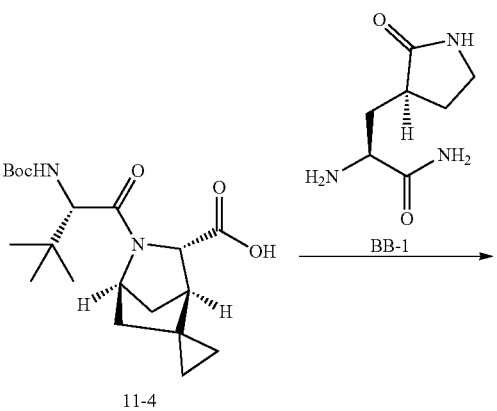

11-4

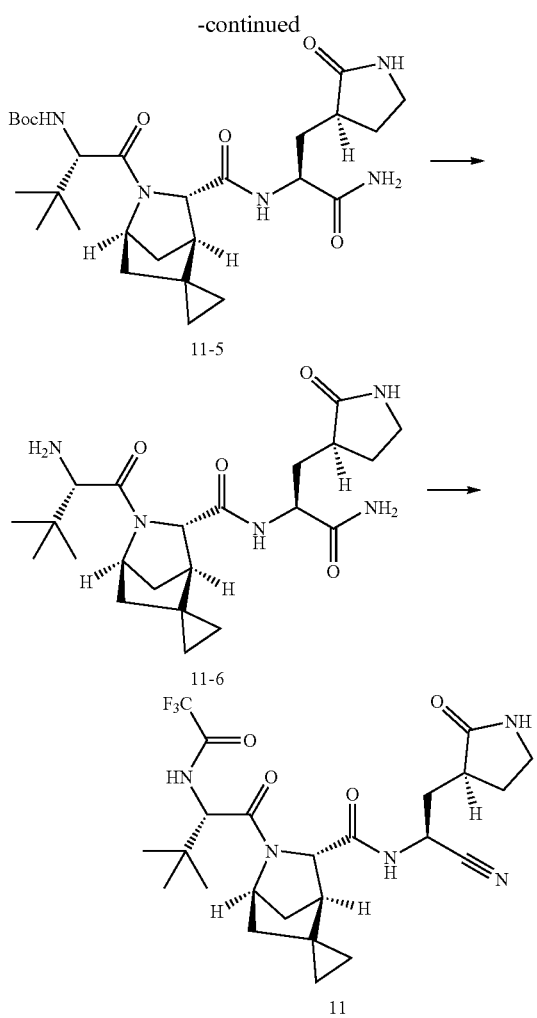

Step 1: Synthesis of Compound 11-1

Compound 10-3 (0.7 g, 1.83 mmol) was dissolved in tetrahydrofuran (14 mL), and TEBBE reagent (0.5 M, 14.64 mL) was added thereto at 0° C. The reaction mixture was stirred at 0° C. for 1 hour then heated to 15° C. and stirred continuously for 3 hours. The reaction mixture was slowly poured into saturated sodium bicarbonate solution (50 mL), filtered through diatomite, extracted with ethyl acetate (30 mL×3), and washed with saturated brine (30 mL×2). The residue was purified by column chromatography (petroleum ether: ethyl acetate=5:1) to obtain compound 11-1. $[M+1]^+=$ 381.1.

Step 2: Synthesis of Compound 11-2

Under nitrogen atmosphere, diethyl zinc (1 M, 13.14 mL) was slowly added to 1,2-dichloroethane (80 mL) at 0° C. After stirring for 0.25 hours, the reaction mixture was slowly added with diiodomethane (7.04 g, 26.28 mmol, 2.12 mL) at 0° C., and stirred for 0.25 hours. Trifluoroacetic acid (149.84 mg, 1.31 mmol, 97.30 μL) was slowly added to the reaction system, stirred continuously for 0.5 hours. A solution of compound 11-1 (0.5 g, 1.31 mmol) in 1,2-dichloroethane (5 mL) was added to the reaction system, heated to 20° C. and stirred continuously for 12 hours. The reaction was quenched with saturated sodium bicarbonate solution (200 mL), extracted with dichloromethane (100 mL), dried over anhydrous sodium sulfate, filtered and concentrated. The crude product was purified by preparative HPLC (column type: Phenomenex luna C18 80*40 mm*3 μm; mobile phase: [H$_2$O (HCl)-acetonitrile]; acetonitrile %: 1%-30%, 7 min) to obtain compound 11-2. $[M+1]^+=295.2$.

Step 3: Synthesis of Compound 11-3

Compound 11-2 (0.1 g, 339.69 μmol) was dissolved in 1,4-dioxane (3 mL), and then a solution of potassium carbonate (187.79 mg, 1.36 mmol) and di-tert-butyl dicarbonate (111.20 mg, 509.53 μmol, 117.06 L) in water (1 mL) was added thereto, and the reaction was stirred at 15° C. for 12 hours. The reaction mixture was poured into water (30 mL), extracted with ethyl acetate (20 mL×3), dried over anhydrous sodium sulfate, filtered, and concentrated. The residue was purified by column chromatography (petroleum ether: ethyl acetate=5:1) to obtain compound 11-3. $[M+1]^+=$ 395.2.

Step 4: Synthesis of Compound 11-4

Compound 11-3 (88.13 mg, 223.40 μmol) was dissolved in tetrahydrofuran (2 mL) and methanol (0.6 mL), and lithium hydroxide monohydrate (28.12 mg, 670.21 μmol) dissolved in water (0.6 mL) was added thereto. The reaction was stirred at 15° C. for 2 hours. The pH was adjusted to 5 with 3% citric acid, and the mixture was extracted with ethyl acetate (20 mL×3), dried over anhydrous sodium sulfate, filtered and concentrated to obtain compound 11-4. $[M+1]^+=381.3$.

Step 5: Synthesis of Compound 11-5

Compound 11-4 (0.056 g, 148.79 μmol) was dissolved in N,N-dimethylformamide (2 mL), then O-(7-azabenzotriazol-1-yl)-N,N,N,N-tetramethyluronium hexafluorophosphate (84.86 mg, 223.18 μmol) was added to the reaction system, and the reaction was stirred at 15° C. for 0.5 hours. Then diisopropylethylamine (76.92 mg, 595.16 μmol, 103.67 μL) was added to the reaction mixture, and a solution of hydrochloride of compound BB-1 (43.26 mg, 208.31 μmol) dissolved in N,N-dimethylformamide (0.5 mL) was added to the reaction system, and the reaction was stirred at 15° C. for 12 hours. The reaction was diluted with water (20 mL), extracted with ethyl acetate (20 mL×3), and the organic phase was washed with 3% citric acid (20 mL), washed with saturated sodium chloride (20 mL), dried over anhydrous sodium sulfate, filtered, and concentrated to obtain compound 11-5. $[M+1]^+=534.4$.

Step 6: Synthesis of Compound 11-6

Compound 11-5 (0.02 g, 37.48 μmol) was dissolved in dichloromethane (2 mL), and trifluoroacetic acid (141.02 mg, 1.24 mmol, 91.57 μL) was added to the reaction system. The reaction mixture was stirred at 15° C. for 1 hour. The reaction was directly quenched with sodium bicarbonate solution (10 mL), extracted with dichloromethane (5 mL×5), and the organic phases were combined, dried over anhydrous sodium sulfate, filtered, and concentrated to obtain compound 11-6. $[M+1]^+=434.2$.

Step 7: Synthesis of Compound 11

Compound 11-6 (0.03 g, 69.20 μmol) was dissolved in dichloromethane (1 mL), and trifluoroacetic anhydride (58.13 mg, 276.79 μmol, 38.50 μL) was added to the reaction system. The reaction mixture was stirred at 15° C. for 1 hour. The reaction was directly quenched with sodium bicarbonate solution (10 mL), extracted with dichloromethane (5 mL×5), and the organic phases were combined, dried over anhydrous sodium sulfate, filtered, and concentrated. The crude product was separated by preparative HPLC (column type: Waters Xbridge BEH C18 100*30 mm*10 μm; mobile phase: [H$_2$O (NH$_4$HCO$_3$)-acetonitrile]; acetonitrile %: 10%-50%, 8 min) to obtain compound 11. $[M+1]^+=512.2$.

Embodiment 12
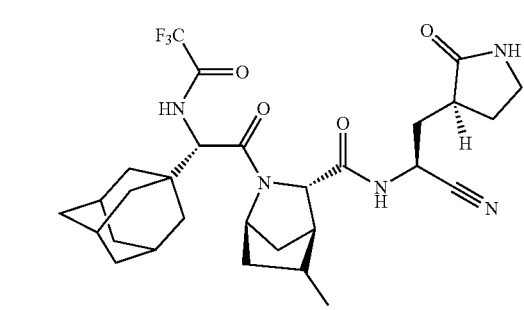
Synthetic route
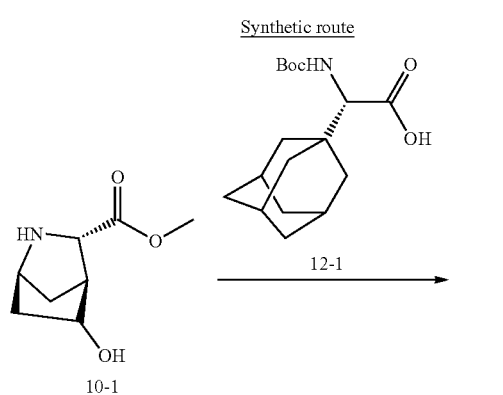
10-1
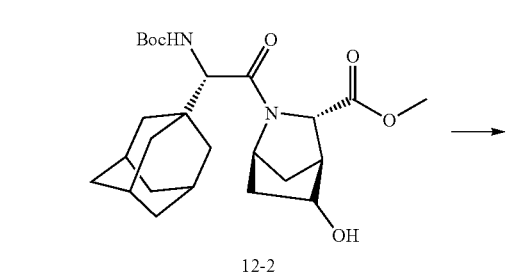
12-2
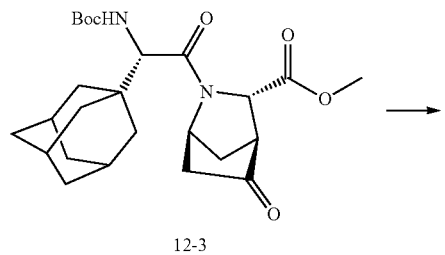
12-3
12-4
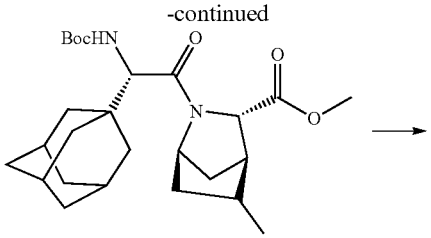
12-5
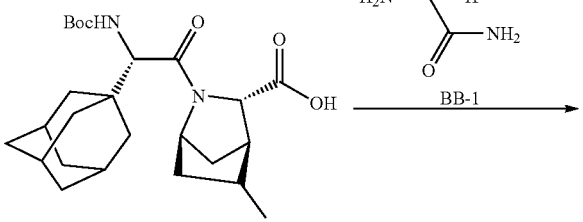
12-6
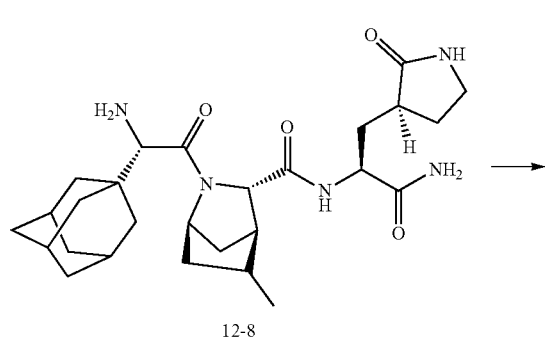
12-7
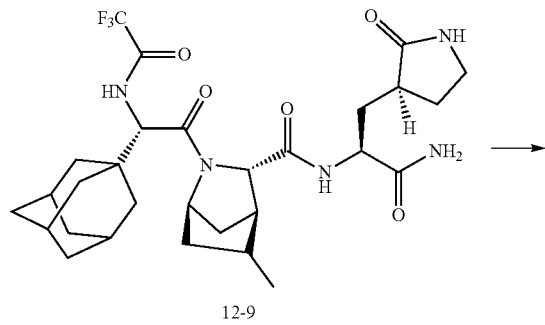
12-8
12-9

-continued

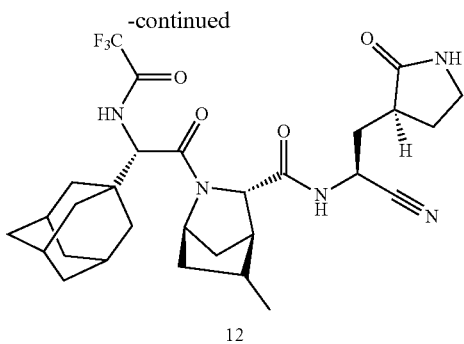

12

Step 1: Synthesis of Compound 12-2

Compound 12-1 (2.36 g, 7.64 mmol) was dissolved in N,N-dimethylformamide (17 mL), then O-(7-azabenzotriazol-1-yl)-N,N,N,N-tetramethyluronium hexafluorophosphate (4.36 g, 11.46 mmol) and diisopropylethylamine (3.95 g, 30.55 mmol) were added thereto, after stirring for 30 min, hydrochloride of compound 10-1 (1.7 g, 8.19 mmol) was added thereto, and the reaction was stirred at 15° C. for 1 hour. The reaction mixture was added with water (15 mL), extracted twice with ethyl acetate (60 mL), and the organic phases were combined, washed twice with 5% citric acid (30 mL), and washed four times with saturated brine (20 mL), dried over anhydrous sodium sulfate, filtered, and evaporated to dryness by rotary evaporation. The residue was purified by column chromatography (petroleum ether: ethyl acetate=1:1) to obtain compound 12-2. $^1$H NMR (400 MHz, CDCl$_3$) δ=5.22 (br d, J=9.76 Hz, 1H), 4.50-4.62 (m, 1H), 4.09-4.18 (m, 2H), 3.74 (br s, 3H), 1.93-2.04 (m, 4H), 1.87 (br d, J=9.88 Hz, 1H), 1.53-1.77 (m, 15H), 1.39-1.46 (m, 9H), 1.27 (t, J=7.13 Hz, 2H). [M+1]$^+$=463.58.

Step 2: Synthesis of Compound 12-3

Compound 12-2 (3 g, 6.49 mmol) was dissolved in acetonitrile (45 mL), and 2-iodobenzoic acid (3.63 g, 12.97 mmol) was added thereto, and the reaction mixture was reacted at 60° C. for 16 hours. The reaction mixture was filtered through diatomite, and evaporated to dryness by rotary evaporation under reduced pressure. Compound 12-3 was obtained. [M+1]$^+$=461.56.

Step 3: Synthesis of Compound 12-4

Compound 12-3 (4 g, 8.69 mmol) was dissolved in tetrahydrofuran (80 mL), cooled to 0° C., and diethylaminosulfur trifluoride (10.24 g, 34.74 mmol) was added thereto, and the reaction mixture was reacted at 15° C. for 3 hours. The reaction mixture was slowly added to saturated sodium bicarbonate solution (100 mL), and extracted three times with ethyl acetate (50 mL), and the combined organic phases were dried over anhydrous sodium sulfate, filtered, and concentrated under reduced pressure. Compound 12-4 was obtained. $^1$H NMR (400 MHz, CDCl$_3$) δ=5.227-5.251 (br d, J=9.6 Hz, 2H), 4.862 (br s, 1H), 4.636 (br s, 1H), 4.191-4.215 (m, 2H), 3.768 (br s, 3H), 3.117 (br s, 1H), 2.369 (br s, 2H), 2.115 (t, J=14.4 Hz, 1H), 2.010-2.046 (br s, 3H), 1.618-1.701 (m, 13H), 1.432 (br s, 9H). [M+1]$^+$=459.59.

Step 4: Synthesis of Compound 12-5

Compound 12-4 (1.90 g, 4.14 mmol) was dissolved in methanol (191 mL), added to another single-necked flask containing a solution of wet palladium on carbon (9.55 g, palladium content of 5%) in methanol, and the reaction system was replaced with a hydrogen balloon for three times, and the reaction mixture was reacted at 15° C. and 15 Psi for 2 hours. The reaction mixture was filtered through diatomite, and evaporated to dryness by rotary evaporation under reduced pressure. Compound 12-5 was obtained. [M+1]$^+$=461.60.

Step 5: Synthesis of Compound 12-6

Compound 12-5 (1.8 g, 3.91 mmol) was dissolved in tetrahydrofuran (40 mL) and methanol (13 mL), then cooled to 0° C., and lithium hydroxide monohydrate (983.94 mg, 23.46 mmol) was added thereto, and the reaction mixture was reacted at 15° C. for 40 hours. The reaction mixture was added with water (30 mL), and the pH was adjusted to 4 to 5 with 5% citric acid (20 mL), then the mixture was extracted twice with ethyl acetate (50 mL), and the organic phases were combined, washed twice with saturated sodium chloride (30 mL), dried over anhydrous sodium sulfate, filtered, and evaporated to dryness by rotary evaporation. Compound 12-6 was obtained without purification. $^1$H NMR (400 MHz, DMSO-d$_6$) δ=1.424 (br s, 9H) 1.594-1.655 (m, 14H) 1.846 (br s, 8H) 2.030 (br s, 1H) 2.540-2.548 (m, 1H) 3.240-3.367 (br d, J=50.8 Hz, 1H) 3.633-3.668 (m, 1H) 3.777-3.823 (m, 1H) 4.446 (br s, 1H) 6.309-6.332 (br d, J=9.2, 1H). [M+1]$^+$=447.58.

Step 6: Synthesis of Compound 12-7

Compound 12-6 (1.3 g, 2.91 mmol) was dissolved in N,N-dimethylformamide (12 mL), then 1-hydroxybenzotriazole (472.01 mg, 3.49 mmol), 1-(3-dimethylaminopropyl)-3-ethylcarbodiimide (837.07 mg, 4.37 mmol) were added thereto, and the reaction was stirred at 15° C. for 30 min. Hydrochloride of compound BB-1 (747.27 mg, 4.37 mmol) and diisopropylethylamine (1.50 g, 11.64 mmol) were added thereto, and the reaction mixture was reacted at 15° C. for 2 hours. The reaction mixture was added with water (50 mL), extracted twice with ethyl acetate (50 mL), and the organic phases were combined, washed twice with 5% citric acid (30 mL) and washed twice with saturated brine (20 mL), dried over anhydrous sodium sulfate, filtered and evaporated to dryness by rotary evaporation. The residue was purified by column chromatography (dichloromethane:methanol=20:1) to obtain compound 12-7. $^1$H NMR (400 MHz, CDCl$_3$) δ=7.730-7.748 (br d, J=7.2 Hz, 1H), 6.162 (br s, 1H) 7.270 (br s, 1H), 5.569 (br d, 1H), 5.288 (br s, 1H), 4.510-4.567 (m, 1H), 4.430 (br d, 1H), 4.331 (br d, 1H), 4.183-4.208 (br d, J=10 Hz, 1H), 3.322-3.360 (t, J=7.6 Hz, 2H), 2.658-2.666 (m, 1H), 2.459 (m, 2H), 2.017-2.076 (m, 1H), 1.990 (m, 8H), 1.602-1.780 (m, 13H), 1.424 (m, 9H), 1.046 (br s, 1H), 0.976-1.029 (br d, J=21.2 Hz, 3H). [M+1]$^+$=600.76.

Step 7: Synthesis of Compound 12-8

Compound 12-7 (920.00 mg, 1.53 mmol) was dissolved in dichloromethane (18.4 mL), then trifluoroacetic acid (7.89 g, 69.22 mmol) was added thereto, and the reaction mixture was reacted at 15° C. for 1 hour. The reaction mixture was directly evaporated to dryness by rotary evaporation. Compound 12-8 was obtained. [M+1]$^+$=500.64.

Step 8: Synthesis of Compound 12-9

Compound 12-8 (420.00 mg, 840.60 μmol) was dissolved in methanol (8.4 mL), then triethylamine (510.36 mg, 5.04 mmol) was added thereto, and methyl trifluoroacetate (1.29 g, 10.09 mmol) was added thereto, and the reaction mixture was heated to 38° C. and stirred for 16 hours. The reaction mixture was concentrated under reduced pressure, added with ethyl acetate (50 mL) and water (20 mL). The pH of the reaction mixture was adjusted to acidic by adding 3% citric acid, and the mixture was extracted three times by adding ethyl acetate (30 mL), and the organic phases were combined, washed with saturated sodium chloride solution (30 mL), dried over anhydrous sodium sulfate, filtered, and concentrated. The residue was purified by column chromatography (dichloromethane:methanol=10:1) to obtain compound 12-9. $^1$H NMR (400 MHz, CDCl$_3$) δ=7.819-7.832 (br d, J=5.2 Hz, 1H), 7.006-7.176 (m, 2H), 5.636-5.947 (m, 3H), 4.343 (br s, 3H), 3.339-3.477 (m, 3H), 2.666 (br s, 1H), 2.487-2.503 (m, 3H), 2.161-2.186 (m, 3H), 2.000-2.020 (br d, J=8 Hz, 4H), 1.856-1.878 (m, 2H), 1.567-1.652 (m, 10H), 1.003-1.061 (m, 5H). [M+1]$^+$=596.65.

Step 9: Synthesis of Compound 12

Compound 12-9 (390.00 mg, 654.74 μmol) was dissolved in dichloromethane (7.8 mL) and tetrahydrofuran (0.78 mL), cooled to 0° C., then Burgess reagent (390.07 mg, 1.64 mmol) was added thereto, and the reaction mixture was reacted at 15° C. for 1 hour. The reaction mixture was added with water (30 mL), extracted twice with ethyl acetate (30 mL), and the organic phases were combined, added with sodium bicarbonate solution (30 mL) and stirred for 20 min, washed with saturated brine (30 mL), dried over anhydrous sodium sulfate, filtered, and concentrated. The crude product was separated by preparative HPLC (column type: C18 100*30 mm*10 μm; mobile phase: [H$_2$O (NH$_4$HCO$_3$)-acetonitrile]; acetonitrile %: 35%-55%, 8 min) to obtain compound 12. $^1$H NMR (400 MHz, CDCl$_3$) δ=8.23 (br d, J=7.00 Hz, 1H), 6.89-7.04 (m, 1H), 5.77-5.86 (m, 1H), 4.94 (br d, J=9.44, 6.91 Hz, 1H), 4.51 (br d, J=9.26 Hz, 1H), 4.40 (br s, 1H), 4.22-4.35 (m, 1H), 3.05-3.81 (m, 3H), 2.71 (br d, J=3.63 Hz, 1H), 2.39-2.66 (m, 2H), 2.12-2.34 (m, 3H), 1.79-2.09 (m, 6H), 1.61-1.73 (m, 11H), 1.43 (m, 1H), 1.17 (br d, J=6.88 Hz, 1H), 0.98-1.14 (m, 3H). [M+1]$^+$=578.64.

Embodiment 13

13

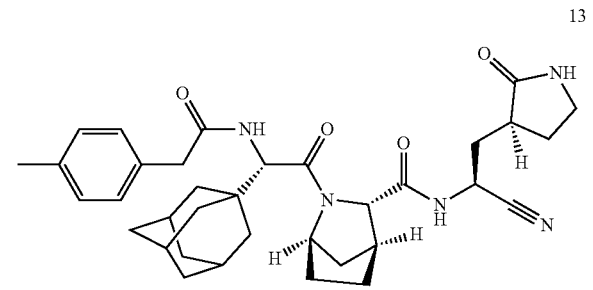

Synthetic route

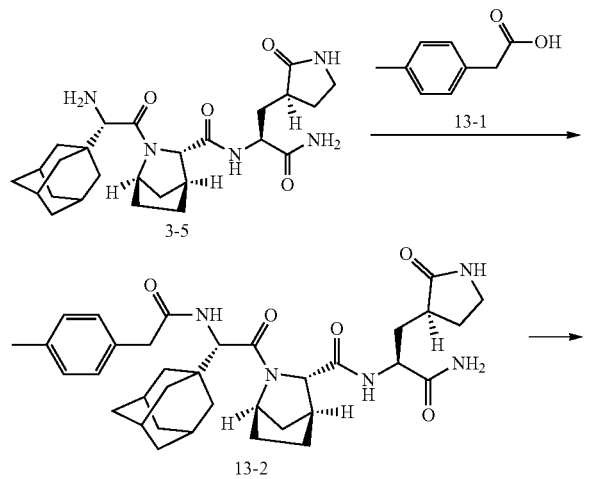

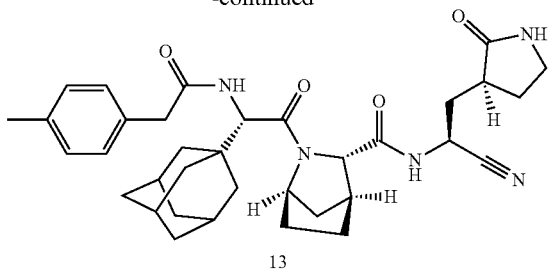

13

Step 1: Synthesis of Compound 13-2

Compound 13-1 (100.50 mg, 669.25 μmol) was dissolved in N,N-dimethylformamide (25 mL), then O-(7-azabenzotriazol-1-yl)-N,N,N,N-tetramethyluronium hexafluorophosphate (293.62 mg, 772.21 μmol) and N,N-diisopropylethylamine (266.14 mg, 2.06 mmol, 358.67 μL) were added thereto, and the reaction mixture was stirred for 0.5 hours. Trifluoroacetate of compound 3-5 (0.25 g) was added thereto, and the reaction mixture was stirred at 20° C. for 16 hours. The reaction mixture was extracted by adding with water (15 mL) and ethyl acetate (30 mL×2), and the organic phases were combined, washed with 5% citric acid (10 mL) and brine (20 mL×4), dried over anhydrous sodium sulfate, filtered, and evaporated to dryness by rotary evaporation. The residue was purified by column chromatography (dichloromethane:methanol=5:1) to obtain compound 13-2. [M+1]$^+$=618.7.

Step 2: Synthesis of Compound 13

Compound 13-2 (0.2 g, 323.74 μmol) was dissolved in dichloromethane (6 mL) and tetrahydrofuran (0.6 mL), and Burgess reagent (115.73 mg, 485.61 μmol) was added thereto, and the reaction mixture was reacted at 15° C. for 1 hour. The reaction mixture was washed with saturated sodium bicarbonate (5 mL), extracted with dichloromethane (10 mL), washed with saturated brine solution (10 mL), dried over anhydrous sodium sulfate, filtered, and concentrated under reduced pressure. The crude product was separated by preparative HPLC (column type: Waters Xbridge Prep OBD C18 150*40 mm*10 μm; mobile phase: [water (NH$_4$HCO$_3$)-acetonitrile]; acetonitrile %: 35%-65%, 8 min), and the fraction was concentrated under reduced pressure to obtain compound 13. [M+1]$^+$=600.7. $^1$H NMR (400 MHz, CDCl$_3$) δ=8.16 (d, J=7.5 Hz, 1H), 7.18 (s, 4H), 4.98 (q, J=7.9 Hz, 1H), 4.62-4.43 (m, 2H), 3.98 (s, 1H), 3.69-3.48 (m, 3H), 3.43-3.27 (m, 2H), 2.37-2.34 (m, 3H), 1.88-1.36 (m, 27H).

Embodiment 14

14

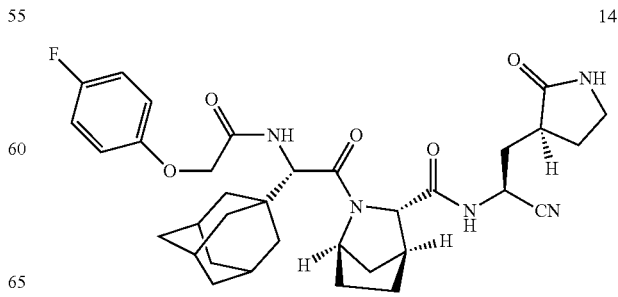

Synthetic route

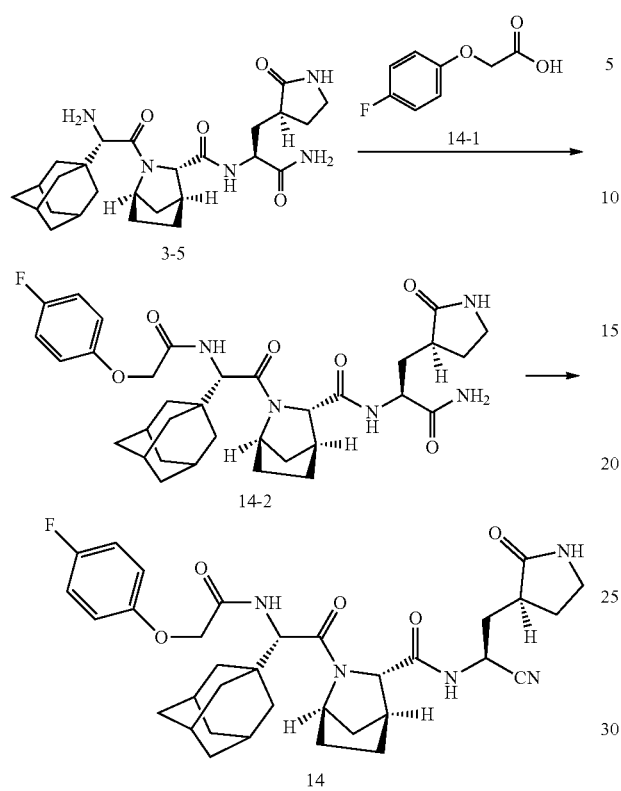

Step 1: Synthesis of Compound 14-2

Compound 14-1 (36.44 mg, 214.16 μmol) was dissolved in N,N-dimethylformamide (10 mL), then O-(7-azabenzotriazol-1-yl)-N,N,N,N-tetramethyluronium hexafluorophosphate (93.96 mg, 247.11 μmol) and N,N-diisopropylethylamine (85.17 mg, 658.95 μmol, 114.78 μL) were added thereto, and the reaction mixture was stirred for 0.5 hours, and trifluoroacetate of compound 3-5 (0.08 g) was added thereto, and the reaction mixture was stirred at 20° C. for 16 hours. The reaction mixture was added with water (15 mL), extracted with ethyl acetate (30 mL×2), and the organic phases were combined, washed with 5% citric acid (10 mL) and brine (20 mL×4), dried over anhydrous sodium sulfate, filtered, and evaporated to dryness by rotary evaporation. The residue was purified by column chromatography (dichloromethane:methanol=5:1) to obtain compound 14-2. [M+1]$^+$=638.7.

Step 3: Synthesis of Compound 14

Compound 14-2 (0.1 g, 156.80 μmol) was dissolved in dichloromethane (3 mL) and tetrahydrofuran (0.3 mL), and Burgess reagent (56.05 mg, 235.21 μmol) was added thereto, and the reaction mixture was reacted at 15° C. for 1 hour. The reaction mixture was washed with saturated sodium bicarbonate (5 mL), extracted with dichloromethane (10 mL), washed with saturated brine solution (10 mL), dried over anhydrous sodium sulfate, filtered, and concentrated under reduced pressure. The crude product was separated by preparative HPLC (column type: Waters Xbridge Prep OBD C18 150*40 mm*10 μm; mobile phase: [water (NH$_4$HCO$_3$)-acetonitrile]; acetonitrile %: 20%-70%, 8 min), and the fraction was concentrated under reduced pressure to obtain compound 14. [M+1]$^+$=620.7. $^1$H NMR (400 MHz, CDCl$_3$) δ=8.23 (br d, J=7.5 Hz, 1H), 7.03-7.03 (m, 1H), 7.21-6.85 (m, 3H), 5.00 (q, J=7.8 Hz, 1H), 4.69-4.40 (m, 3H), 4.04-3.94 (m, 1H), 3.45-3.26 (m, 2H), 2.95-2.79 (m, 1H), 2.66-1.24 (m, 23H).

Embodiment 15

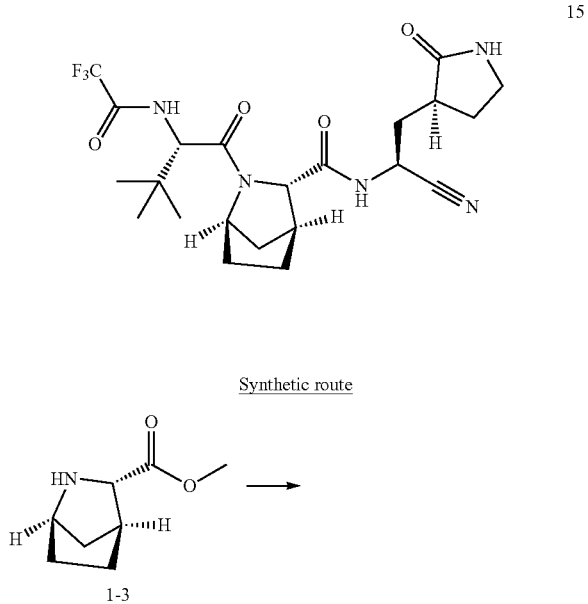

Synthetic route

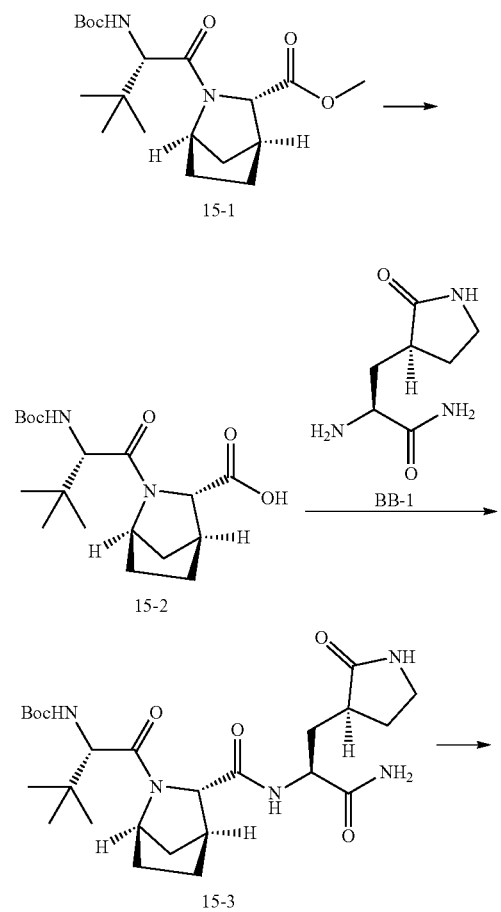

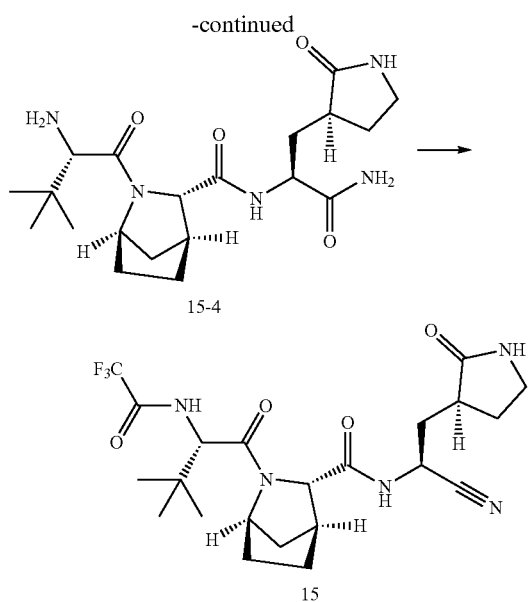

Step 1: Synthesis of Compound 15-1

At 0° C., N-Boc-L-tert-leucine (0.21 g, 1.10 mmol), N,N-diisopropylethylamine (426.49 mg, 3.30 mmol, 574.79 μL), 2-(7-azobenzotriazol-1-yl)-N,N,N,N-tetramethyluronium hexafluorophosphate (627.38 mg, 1.65 mmol) were added to a solution of hydrochloride of compound 1-3 (305.30 mg, 1.32 mmol) in N,N-dimethylformamide (2 mL), and the reaction mixture was reacted at 20° C. for 16 hours. The reaction mixture was poured into 5% citric acid solution to separate the phases, and the aqueous phase was extracted with ethyl acetate (20 mL*2), and the organic phase was dried over anhydrous sodium sulfate, filtered, and concentrated under reduced pressure to obtain a crude product. The crude product was separated by silica gel column chromatography (petroleum ether/ethyl acetate=3:1) to obtain compound 15-1. $^1$H NMR (400 MHz, CDCl$_3$) δ=5.21 (br d, J=9.6 Hz, 1H), 4.48-4.37 (m, 1H), 4.30-4.21 (m, 1H), 4.01-3.95 (m, 1H), 3.68-3.60 (m, 3H), 2.73-2.61 (m, 1H), 1.97-1.87 (m, 1H), 1.79-1.56 (m, 4H), 1.39-1.33 (m, 10H), 0.97 (s, 9H).

Step 2: Synthesis of Compound 15-2

Lithium hydroxide monohydrate (51.25 mg, 1.22 mmol) was added to a solution of compound 15-1 (0.3 g, 814.19 μmol) in tetrahydrofuran (2 mL) and water (1 mL), and the reaction mixture was reacted at 20° C. for 16 hours. The reaction mixture was added with 20 mL of 5% citric acid aqueous solution, and added with 20 mL of ethyl acetate to separate the phases, and the organic phase was dried over anhydrous sodium sulfate, filtered and concentrated to obtain a crude product. Compound 15-2 was obtained. $^1$H NMR (400 MHz, CDCl$_3$) δ=5.24 (d, J=9.9 Hz, 1H), 4.51-4.45 (m, 1H), 4.41-4.33 (m, 1H), 4.18-4.15 (m, 1H), 3.06-2.99 (m, 1H), 1.99-1.89 (m, 1H), 1.85-1.75 (m, 3H), 1.59-1.49 (m, 2H), 1.46-1.42 (m, 9H), 1.05-1.01 (m, 9H).

Step 3: Synthesis of Compound 15-3

At 0° C., hydrochloride of compound BB-1 (196.85 mg, 947.97 μmol), N-methylimidazole (291.87 mg, 3.55 mmol), N,N,N,N-tetramethylchloroformamidinium hexafluorophosphate (265.98 mg, 947.97 μmol) were added to a solution of compound 15-2 (0.28 g, 789.98 μmol) in N,N-dimethylformamide (3 mL), and reacted at 20° C. for 16 hours. The reaction mixture was poured into 20 mL of water, and a mixed solution of dichloromethane and methanol (volume ratio of 10:1) was added for extraction (20 mL*2), and the organic phase was washed with 5% citric acid solution (20 mL*1), dried over anhydrous sodium sulfate, filtered, and concentrated under reduced pressure to obtain a crude product. The crude product was separated by silica gel column chromatography (dichloromethane/methanol=20:1) to obtain compound 15-3. $^1$H NMR (400 MHz, CDCl$_3$) δ=4.71-4.23 (m, 3H), 3.97 (br s, 1H), 3.35 (br d, J=7.1 Hz, 2H), 2.83-2.74 (m, 1H), 2.61-2.31 (m, 2H), 2.09 (br s, 1H), 2.04-1.92 (m, 2H), 1.88-1.64 (m, 4H), 1.57-1.34 (m, 11H), 1.11-0.89 (m, 9H).

Step 4: Synthesis of Trifluoroacetate of Compound 15-4

At 0° C., trifluoroacetic acid (2 mL) was added to a solution of compound 15-3 (0.2 g, 393.99 μmol) in dichloromethane (6 mL), and the reaction mixture was reacted at 20° C. for 2 hours. The reaction mixture was concentrated under reduced pressure to obtain trifluoroacetate of compound 15-4.

Step 5: Synthesis of Compound 15

At 0° C., pyridine (187.07 mg, 2.37 mmol, 190.89 μL), trifluoroacetic anhydride (206.97 mg, 985.43 μmol, 137.07 μL) were added to a solution of trifluoroacetate of compound 15-4 (0.175 g, 394.17 mol) in tetrahydrofuran (2 mL), and the reaction mixture was reacted at 20° C. for 4 hours. The reaction mixture was quenched with 20 mL of water, extracted with ethyl acetate (20 mL*2), and the organic phase was washed with 5% citric acid (20 mL*1), dried over anhydrous sodium sulfate, filtered, and concentrated under reduced pressure to obtain a crude product. The crude product was separated by pre-HPLC (column type: Waters Xbridge BEH C18 100*25 mm*5 μm; mobile phase: [H$_2$O (NH$_4$HCO$_3$)-ACN]; ACN %: 20%-50%, 10 min) to obtain compound 15. $^1$H NMR (400 MHz, CDCl$_3$) δ=9.43-8.31 (m, 1H), 7.11-6.95 (m, 1H), 5.93-5.71 (m, 1H), 4.92-4.76 (m, 1H), 4.72-4.62 (m, 1H), 4.55-4.44 (m, 1H), 4.01-3.89 (m, 1H), 3.48-3.30 (m, 2H), 2.88-2.78 (m, 1H), 2.62-2.38 (m, 2H), 2.34-2.15 (m, 2H), 2.04-1.75 (m, 4H), 1.71-1.58 (m, 3H), 1.57-1.41 (m, 2H), 1.07-0.92 (m, 9H).

Embodiment 16

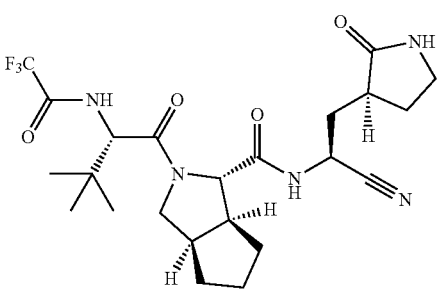

16

Synthetic route

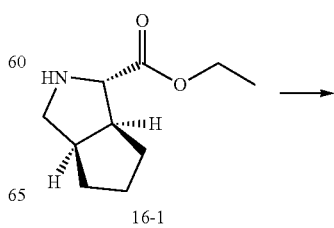

16-1

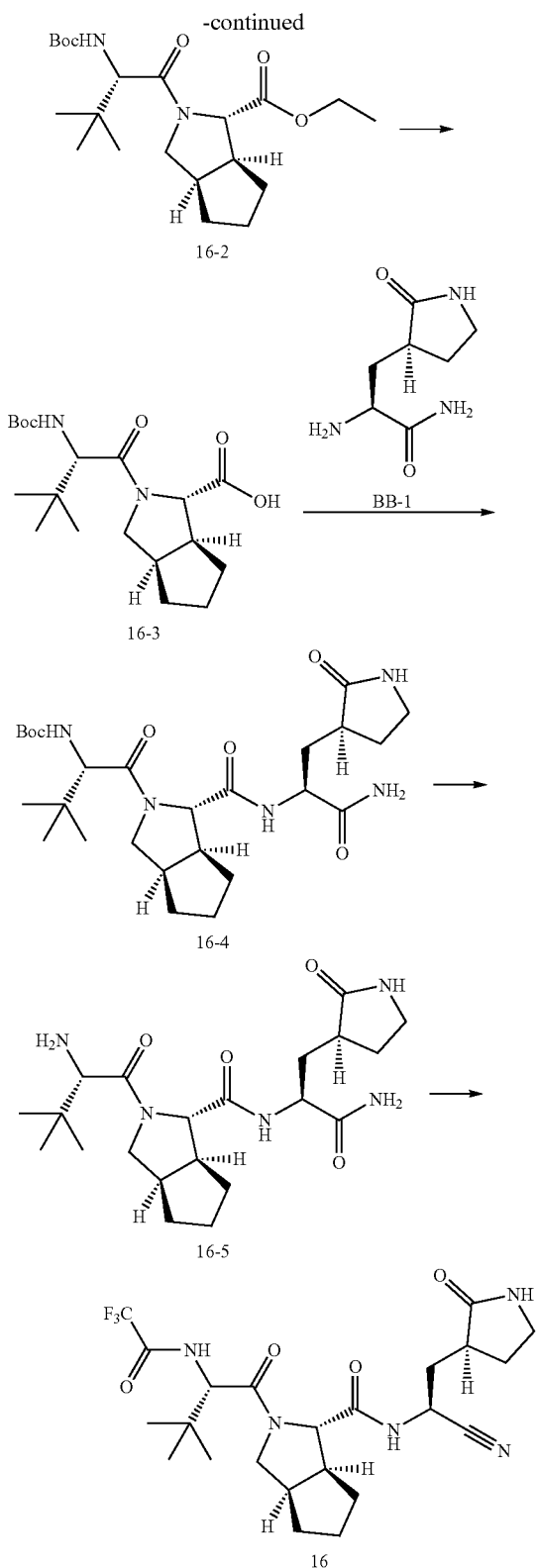

Hydrochloride of compound 16-1 (949.93 mg, 4.32 mmol) was added to N,N-dimethylformamide (10 mL), then 2-(7-azabenzotriazol-1-yl)-N,N,N,N-tetramethyluronium hexafluorophosphate (1.97 g, 5.19 mmol) was added thereto and the reaction was stirred for 0.5 hours, then diisopropylethylamine (1.40 g, 10.81 mmol) and N-Boc-L-tert-leucine (1 g, 4.32 mmol) were added thereto, and the reaction was stirred at 20° C. for 16 hours. The reaction mixture was washed with methyl tert-butyl ether (50 mL), water (20 mL), 3% citric acid (20 mL*2) and saturated sodium chloride solution (20 mL), and the organic phase was dried over anhydrous sodium sulfate, filtered and concentrated under reduced pressure. The residue was purified by silica gel column chromatography (petroleum ether: ethyl acetate=3:1) to obtain compound 16-2. $^1$H NMR (400 MHz, CDCl$_3$) δ=5.27-5.18 (m, 1H), 4.36 (d, J=4.1 Hz, 1H), 4.33-4.28 (m, 1H), 4.23-4.13 (m, 2H), 3.89-3.80 (m, 1H), 3.79-3.70 (m, 1H), 2.77-2.61 (m, 2H), 1.98-1.82 (m, 2H), 1.80-1.70 (m, 1H), 1.69-1.60 (m, 2H), 1.54-1.47 (m, 1H), 1.46-1.41 (m, 9H), 1.29-1.25 (m, 3H), 1.06-1.00 (m, 9H).

Step 2: Synthesis of Compound 16-3

Compound 16-2 (0.2 g, 504.39 μmol) was added to tetrahydrofuran (3 mL), and a solution of lithium hydroxide monohydrate (63.50 mg, 1.51 mmol) in water (1.5 mL) was added thereto, and the reaction was stirred at 20° C. for 16 hours. The crude product was neutralized with 3% citric acid solution (20 mL), extracted with ethyl acetate (30 mL), and the organic phase was washed with saturated sodium chloride solution (10 mL), dried over anhydrous sodium sulfate, filtered and concentrated under reduced pressure. Compound 16-3 was obtained without purification. $^1$H NMR (400 MHz, CD$_3$OD) δ=4.32-4.25 (m, 2H), 3.90-3.81 (m, 2H), 2.85-2.67 (m, 2H), 2.01-1.86 (m, 2H), 1.79-1.50 (m, 5H), 1.44 (s, 9H), 1.06-1.00 (m, 9H).

Step 3: Synthesis of Compound 16-4

Compound 16-3 (0.35 g, 949.88 μmol), hydrochloride of compound BB-1 (197.25 mg, 949.88 μmol) were added to N,N-dimethylformamide (4 mL), cooled to 0° C., then 1-methylimidazole (272.95 mg, 3.32 mmol) and N,N,N,N-tetramethylchloroformamidinium hexafluorophosphate (399.78 mg, 1.42 mmol) were added thereto, and the reaction was gradually warmed to 20° C. and stirred for 16 hours. The reaction mixture was washed with ethyl acetate (50 mL), water (20 mL), 3% citric acid (20 mL*2) and saturated sodium chloride solution (20 mL), and the organic phase was dried over anhydrous sodium sulfate, filtered and concentrated under reduced pressure. The residue was purified by silica gel column chromatography (dichloromethane: methanol=20:1) to obtain compound 16-4. $^1$H NMR (400 MHz, CDCl$_3$) δ=8.15-7.87 (m, 1H), 7.24-7.14 (m, 1H), 6.19-5.95 (m, 1H), 5.81-5.55 (m, 1H), 5.44-5.24 (m, 1H), 4.51-3.72 (m, 5H), 3.49-3.27 (m, 2H), 2.86-2.64 (m, 2H), 2.55-2.26 (m, 2H), 1.97-1.75 (m, 5H), 1.73-1.55 (m, 3H), 1.51-1.36 (m, 10H), 1.06-0.90 (m, 9H).

Step 4: Synthesis of Trifluoroacetate of Compound 16-5

Compound 16-4 (0.31 g, 594.27 μmol) was added to dichloromethane (3 mL), and trifluoroacetic acid (1 mL) was added thereto, and the reaction was stirred at 20° C. for 2 hours. The reaction mixture was concentrated under reduced pressure. Trifluoroacetate of compound 16-5 was obtained. [M+1]$^+$=422.30

Step 5: Synthesis of Compound 16

Trifluoroacetate of compound 16-5 (240 mg, 448.13 μmol) was added to tetrahydrofuran (3 mL), cooled to 0° C., then pyridine (212.68 mg, 2.69 mmol) was added thereto, and trifluoroacetic anhydride (235.30 mg, 1.12 mmol) was added dropwise thereto, and the reaction was gradually warmed to 20° C. and stirred for 1 hour. The reaction mixture was washed with ethyl acetate (50 mL), water (10 mL), 3% citric acid (20 mL*2) and saturated sodium chloride solution (10 mL), and the organic phase was dried over anhydrous sodium sulfate, filtered and concentrated under reduced pressure. The residue was purified by silica gel column chromatography (dichloromethane:methanol=20:1) to obtain compound 16. $^1$H NMR (400 MHz, DMSO-d$_6$) δ=8.74-8.25 (m, 2H), 7.30-7.12 (m, 1H), 4.99-4.83 (m, 1H), 4.60-4.47 (m, 1H), 4.21-4.14 (m, 1H), 3.92-3.82 (m, 1H), 3.65-3.57 (m, 1H), 3.25-3.09 (m, 2H), 2.80-2.70 (m, 1H), 2.62-2.54 (m, 1H), 2.46-2.38 (m, 1H), 2.28-2.14 (m, 2H), 1.94-1.55 (m, 7H), 1.47-1.36 (m, 1H), 1.02 (s, 9H).

Biological Test:

Experimental Embodiment 1: Evaluation of the In Vitro Anti-Novel Coronavirus Mpro Protease Activity of the Test Compound 1. Experimental Materials:
1.1 Reagents and Consumables:

TABLE 1

Names and brands of reagents and consumables

| | Name of reagent and consumable | Brand |
|---|---|---|
| 1 | Tris | Sigma |
| 2 | EDTA | Sigma |
| 3 | NaCl | Sigma |
| 4 | 384 well plate | Perkin Elmer |
| 5 | Dimethyl sulfoxide (DMSO) | Sigma |
| 6 | Substrate (Dabcyl-KTSAVLQSGFRKM-(Edans)) (SEQ ID NO: 1) | GenScript |
| 7 | SARS-CoV-2 Mpro | WuXi AppTec |
| 8 | GC376 | TargetMol |

1.2 Instruments

TABLE 2

Instruments and brands

| | Instrument | Brand |
|---|---|---|
| 1 | SpectraMax M2e microplate reader | Molecular Devices |
| 2 | Echo 655 liquid workstation | Labcyte |
| 3 | Tabletop high-speed centrifuge | Eppendorf |

2. Experimental Method:

The compound was dissolved in DMSO, and diluted in a 3-fold gradient with Echo655 according to the concentration requirements to 10 concentration points, and duplicate tests were set at each concentration, and the diluted solution was added to a 384-well plate. Mpro protein and substrate were diluted with test buffer (100 mM NaCl, 20 mM Tris-HCl, 1 mM EDTA), and Mpro protein was added to the 384-well test plate, incubated with the compound for 30 min at room temperature, and then the substrate was added thereto, and the test concentration of Mpro protein was 25 nM, and the test concentration of substrate was 25 M. After incubating for 60 minutes in a 30° C. constant temperature incubator, the fluorescence signal value of Ex/Em=340 nm/490 nm was detected by microplate reader. At the same time, the background well containing the substrate and compound but not containing Mpro protein was detected as control.

3. Data Analysis:
1) The inhibition rate was calculated using the following formula:

Inhibition rate %=[(compound−BG$_{compound}$)−(ZPE−BG$_{ZPE}$)]/[(HPE−BG$_{HPE}$)−(ZPE−BG$_{ZPE}$)]*100%

HPE: 100% inhibition control, containing 25 nM Mpro protein+25 μM substrate+1 μM GC376
ZPE: No-inhibition control, containing 25 nM Mpro protein+25 μM substrate, not containing compound
Compound: Test compound well, containing 25 nM Mpro protein+25 μM substrate+compound
BG: Background control well, containing 25 μM substrate+compound, not containing Mpro protein 2) Log (agonist) vs. response—variable slope nonlinear fitting analysis was carried out on the inhibition rate data (inhibition rate %) of the compound by using GraphPad Prism software, and the IC$_{50}$ value of the compound was obtained.

TABLE 3

In vitro anti-novel coronavirus Mpro protease activity of test compounds

| Compound number | IC$_{50}$ (nM) |
|---|---|
| 2 | 249 |
| 3 | 21 |
| 4 | 53 |
| 5 | 35 |
| 6 | 135 |
| 7 | 62 |
| 9 | 25 |
| 10 | 17 |
| 11 | 5.4 |
| 12 | 17 |
| 13 | 75 |
| 14 | 119 |
| 15 | 94 |
| 16 | 43 |

Conclusion: The compounds of the present disclosure have good anti-novel coronavirus Mpro protease activity in vitro.

Experimental Embodiment 2: Evaluation of In Vitro Anti-Coronavirus Activity of Compounds by Cytopathic Model 1. Experimental Materials
1.1 Reagents and Consumables

TABLE 4

Names and brands of reagents and consumables

| | Name of reagent and consumable | Brand |
|---|---|---|
| 1 | MEM medium | Sigma |
| 2 | L-Glutamine | Gibco |
| 3 | Non-essential amino acid | Gibco |
| 4 | Double antibody (Penicillin-Streptomycin Solution) | HyClone |
| 5 | Fetal bovine serum (FBS) | ExCell |
| 6 | Phosphate buffered saline (DPBS) | Corning |
| 7 | 0.25% Trypsin | Gibco |
| 8 | CellTiter Glo cell activity assay kit | Promega |
| 9 | Remdesivir | MCE |
| 10 | 96-well plate | Grenier |

1.2 Instruments

TABLE 5

Instruments and brands

| | Instrument | Brand |
|---|---|---|
| 1 | Microplate reader | BioTek |
| 2 | Cell counter | Beckman |
| 3 | CO$_2$ incubator | Thermo |

1.3 Cells and Viruses

MRC5 cells and coronavirus HCoV OC43 were purchased from ATCC.

MRC5 cells were cultured in MEM (Sigma) medium supplemented with 10% fetal bovine serum (Excell), 1% double antibody (Hyclone), 1% L-glutamine (Gibco) and 1% non-essential amino acids (Gibco). MEM (Sigma) medium supplemented with 5% fetal bovine serum (Excell), 1% double antibody (Hyclone), 1% L-glutamine (Gibco) and 1% non-essential amino acid (Gibco) was used as the experimental culture medium.

2. Experimental Method

TABLE 6

Virus test methods used in this study

| Virus (strain) | Cell | Compound treatment time (day)/endpoint method | Control compound | Detection reagent |
| --- | --- | --- | --- | --- |
| HCoV OC43, 100TCID$_{50}$/well | 20,000 MRC5 cells/well | 5/CPE | Remdesivir | CellTiter Glo. |

Cells were inoculated into a 96 microwell plate at a certain density (Table 6) and culture overnight in an incubator at 5% $CO_2$ and 37° C. On the second day, the compound was added after doubling dilution (8 concentration points, duplicate wells), with 50 µL per well. Then the diluted virus was added to the cells at 100 TCID$_{50}$ per well, 50 µL per well. Cell control (cell without compound treatment or virus infection), virus control (cell infected with virus without compound treatment) and culture medium control (only culture medium) were set. The final volume of the culture medium in this experiment was 200 µL, and the final concentration of DMSO in the culture medium was 0.5%. Cells were cultured in a 5% $CO_2$, 33° C. incubator for 5 days. Cell viability was detected using the cell viability assay kit CellTiter Glo (Promega). Cytotoxicity experiments were performed under the same conditions as antiviral experiments, but without virus infection.

3. Data Analysis:

The antiviral activity and cytotoxicity of the compound were represented by the inhibition rate (%) and cell viability (%) of the compound on the cytopathic effect caused by the virus at different concentrations, respectively. The calculation formula is as follows:

Inhibition rate (%)=(reading value of test well−average value of virus control)/(average value of cell control−average value of virus control)×100

Cell viability (%)=(reading value of test well−average value of culture medium control)/(average value of cell control−average value of culture medium control)×100

GraphPad Prism was used to perform nonlinear fitting analysis on the inhibition rate and cell viability of the compound, and the half effective concentration ($EC_{50}$) and half cytotoxic concentration ($CC_{50}$) of the compound were calculated.

TABLE 7

Evaluation of anti-coronavirus activity of compounds in vitro by cytopathic model

| Compound number | $EC_{50}$ (nM) | $CC_{50}$ (nM) |
| --- | --- | --- |
| 2 | 697 | >10000 |
| 3 | 62 | >10000 |
| 4 | 141 | >10000 |
| 5 | 205 | >10000 |
| 11 | 3.5 | >10000 |
| 15 | 191 | >10000 |
| 16 | 83 | >10000 |

Conclusion: The compounds of the present disclosure have good in vitro anti-coronavirus activity at the cellular level, and have no cytotoxicity.

Embodiment 3: Anti-Novel Coronavirus Activity and Toxicity Test 3.1: Cell Source and Type of New Coronavirus Nuclear viruses were obtained from African green monkey kidney (Vero) cells from the American Type Culture Collection (ATCC), Cat. No. CCL-81. Cells were cultured in Dulbecco's Modified Eagle's Medium (DMEM, WelGene) supplemented with 10% fetal bovine serum (Gibco) and 1% double antibody (Gibco). DMEM medium supplemented with 2% fetal bovine serum (Gibco) and 1% double antibody (Gibco) was used as the experimental culture medium.

Novel coronavirus βCoV/KOR/KCDC03/2020 strain was provided by Korea Centers for Disease Control and Prevention (KCDC), Serial No. NCCP43326.

3.2: Experimental Process

Cell Plating

After the Vero cells were digested by trypsin, the Vero cells were diluted to 480,000 cells per mL with experimental culture medium. The diluted cells were added to a 384-well cell test plate with 25 µL and 12,000 cells per well using an automatic liquid separator. Cells were cultured overnight in a 5% $CO_2$ and 37° C. incubator.

Compound Treatment and Viral Infection

On the second day, the compound and CP-100356 were diluted with DMSO, and the diluted compound was added to the test cell wells using a liquid workstation. Then, 25 µL of SARS-CoV-2 virus diluted with the experimental culture medium was added to each well, with MOI=0.0125. Cell control (cells without compound treatment or virus infection) and no compound treatment control (cell infected with virus without compound treatment with 0.5% DMSO), and CP-100356 control (cell infected with virus, treated with 2 µM CP-100356) were set. The final volume of cell culture medium in each well was 50 µL. Cells were cultured in a 5% $CO_2$ and 37° C. incubator for 24 hours.

Immunofluorescence Staining (1) After 24 hours of virus infection, 17 µL of 16% paraformaldehyde was added to each well. Then the virus was left at room temperature for 30 minutes;

(2) the supernatant was aspirated and the plate was washed twice with DPBS;

(3) 25 µL of 0.25% Tritonx-100 was added to each well and left at room temperature for 20 minutes;

(4) 0.25% TritonX-100 was aspirated, and DPBS was used to wash the plate twice;

(5) 25 µL of diluted primary antibody (1:3000-fold diluted) was added to each well and incubated at 37° C. for 1 hour;

(6) the primary antibody was aspirated and DPBS was used to wash the plate twice;

(7) 25 µL of diluted secondary antibody Alexa Fluor 488-labeled sheep anti-rabbit IgG (1:2000-fold dilution) and 2.5 µg/mL (1:4000-fold dilution) of Hoechst 33342 were added to each well and incubated for 1 hour at 37° C.;

(8) the secondary antibody and Hoechst were aspirated, and the plate was washed twice with DPBS;

(9) high-content imaging analyzer Operetta was used to read the plate, and the instrument was set as: 488/405 emission, 20× objective, 5 fields of view per well.

Data Analysis

Columbus software was used to quantitatively analyze the total number of cells (the number of cells stained by Hoechst) and the number of cells infected by the new coronavirus (the number of cells labeled with Alexa Fluor 488) in the images read by the high-content imaging analyzer. The ratio of infected cells and the total number of cells were used to analyze the antiviral activity and cytotoxicity of the compounds. The calculation formula is as follows:

Inhibition rate (%)=100−(ratio of infected cells in test wells−average ratio of infected cells in cell control wells)/(average ratio of infected cells in control wells without compound treatment−average ratio of infected cells in cell control wells)×100

Cell viability (%)=total number of cells in test wells/average total number of cells in control wells without compound treatment×100

XLfit 4 software was used for nonlinear fitting analysis of the inhibitory activity and cell viability of the compounds, and the $IC_{50}$ and $CC_{50}$ values of the compounds were calculated. The fitting method was "Sigmoidal dose-response". The calculation formula of $IC_{50}$ and $CC_{50}$ is: Y=Bottom+(Top Bottom)/(1+($IC_{50}$/X)Hillslope).

TABLE 8

Evaluation of anti-coronavirus activity of compounds in vitro by wild-type novel coronavirus

| Compound number | $EC_{50}$ (nM) | $CC_{50}$ (nM) |
|---|---|---|
| 3 | 35 | >5000 |
| 4 | 30 | >5000 |
| 5 | 20 | >5000 |
| 9 | 19 | >5000 |
| 11 | 3.5 | >5000 |

Conclusion: The compounds of the present disclosure have good anti-novel coronavirus activity in vitro.

Experimental Embodiment 4: Pharmacokinetics Test of Mice

In this study, C57BL/6J male mice were selected as test animals, and LC/MS/MS method was used to quantitatively measure the plasma concentration of the test compound 11 at different time points after oral administration and injection in mice, so as to evaluate the pharmacokinetic characteristics of the test drug in mice.

The test compound dissolved in 30% PEG400+70% normal saline was administered to mice (overnight fasting, 6-8 weeks old) by intragastric administration. 25 µL of blood was collected at 0.083, 0.25, 0.5, 1, 2, 4, 8, 12 and 24 hours after administration, respectively, and placed in commercial anticoagulation tubes pre-added with EDTA-K2, centrifuged at 4° C., 3200 g for 10 min to obtain plasma, and after the plasma sample was treated, the plasma concentration was determined by LC-MS/MS method.

TABLE 9

Pharmacokinetic parameters of compound 11 in mice

| PK parameter | i.v. @ 3 mpk | p.o. @ 10 mpk |
|---|---|---|
| $C_{max}$ (nM) | NA | 1855 |
| $T_{max}$ (h) | NA | 0.25 |
| $T_{1/2}$ (h) | 0.2 | NA |
| $Vd_{ss}$ (L/kg) | 0.9 | NA |
| CL(mL/min/kg) | 68.5 | NA |
| $AUC_{0-last}$ (nM · h) | 1447 | 1519 |

NA means not present;

NA means not present;
Conclusion: The compounds of the present disclosure are cleared quickly in mice, resulting in low exposure of the compounds, and about 30% bioavailability for oral absorption.

Experimental Embodiment 5: Pharmacokinetic Test of the Compound of the Present Disclosure in Combination with Ritonavir In this study, C57BL/6J male mice were selected as test animals, and the LC/MS/MS method was used to quantitatively measure the plasma concentrations of mice in combination with Ritonavir at different time points, so as to evaluate the pharmacokinetic characteristics of the test drug in mice.

Firstly, 10 mpk of Ritonavir was administered to mice by intragastric administration at −12 h and 0 h, and then the test compound was dissolved in 30% PEG400+70% normal saline solution and administered to mice by intragastric administration (overnight fasting, 6 to 8 weeks old). 25 µL of blood was collected at 0.083, 0.25, 0.5, 1, 2, 4, 8, 12 and 24 hours after administration to animals, placed in a commercial anticoagulant tube pre-added with EDTA-K2, and centrifuged at 4° C., 3200 g for 10 min to obtain plasma. After the plasma samples were treated, the plasma concentration was determined by LC-MS/MS method.

TABLE 10

Pharmacokinetic parameters of compound 11 in combination with Ritonavir in mice

| PK parameter | p.o.@ 10 mpk |
|---|---|
| $C_{max}$ (nM) | 10090 |
| $T_{max}$ (h) | 0.5 |
| $AUC_{0-last}$ (nM · h) | 28683 |

Conclusion: After the compound of the present disclosure is used in combination with Ritonavir, the exposure is increased by nearly 20 times compared with single drug.

Experimental Embodiment 6: Tissue Distribution Test in Rats

In this study, SD male rats were selected as test animals, and the drug concentrations of test compounds in plasma and lungs of rats at different time points were quantitatively measured by LC/MS/MS method to evaluate the pharmacokinetic characteristics of test drugs in rats.

Firstly, 10 mpk of Ritonavir was administered to rats by intragastric administration at −12 h and 0 h, and 30 mpk of the test compound was dissolved in 10% Solutol+30% PEG 400+2% Tween 80+$H_2O$ 58% solution and administered to rats by intragastric administration (overnight fasting). 40 µL of blood was collected from the saphenous vein of rats at 0.25, 1 and 6 hours after administration, placed in an anticoagulant tube added with EDTA-K2, centrifuged at 4° C., 3200 g for 10 min to obtain plasma, and some animals were killed at 0.25, 1 and 6 hours respectively to collect lung tissue. After the plasma samples were treated, the plasma concentration was determined by LC-MS/MS method.

TABLE 11

Pharmacokinetic parameters of compound 11 in rats

| Tissue concentration and ratio at each time point | Lung/plasma (nM) | Ratio |
|---|---|---|
| 0.25 h | 15800/2860 | 5.5/1 |
| 1 h | 18450/5490 | 3.2/1 |
| 6 h | 7850/4875 | 1.6/1 |
| AUC(0-6 h) (h · nmol/L) | 76840/29371 | 2.6/1 |

Conclusion: After the compound of the present disclosure is used in combination with Ritonavir, there is higher exposure in the lungs in rats.

What is claimed is:

1. A compound represented by formula (I") or a pharmaceutically acceptable salt thereof,

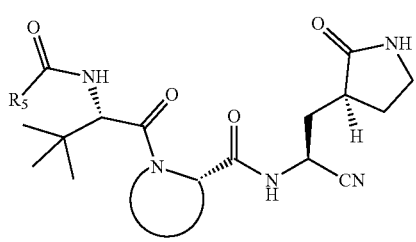
(I")

wherein,
$R_5$ is selected from $C_{1-3}$ haloalkyl;
the structural moiety

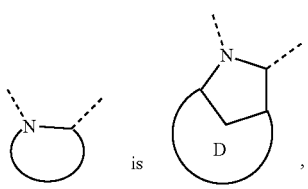

and the

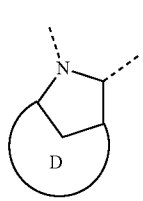

is optionally and independently substituted by 1, 2 or 3 $R_{a'}$;
ring D is selected from $C_{4-8}$ cycloalkyl, $C_{5-8}$ cycloalkenyl and 5- to 8-membered heterocycloalkyl, and the $C_{4-8}$ cycloalkyl is optionally substituted by 1 or 2 $R_{a'}$;
$R_{a'}$ is each independently selected from F and methyl;
the heterocycloalkyl contains 1, 2 or 3 heteroatoms or heteroatom groups independently selected from O, S, N and NH.

2. The compound or the pharmaceutically acceptable salt thereof according to claim 1, wherein the compound is represented by formula (I'),

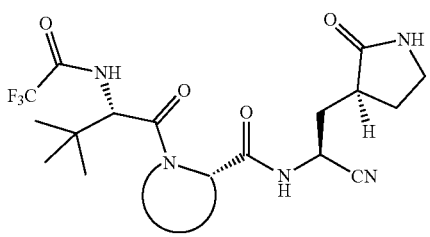
(I')

wherein,
the structural moiety

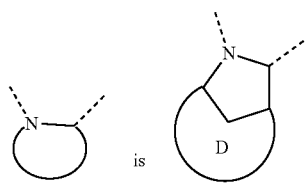

and the

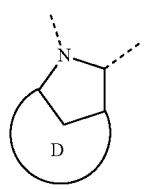

is optionally and independently substituted by 1, 2 or 3 $R_{a'}$;
ring D is selected from $C_{4-8}$ cycloalkyl, $C_{5-8}$ cycloalkenyl and 5- to 8-membered heterocycloalkyl, and the $C_{4-8}$ cycloalkyl is optionally substituted by 1 or 2 $R_{a'}$;
$R_{a'}$ is each independently selected from F and methyl;
the heterocycloalkyl contains 1, 2 or 3 heteroatoms or heteroatom groups independently selected from O, S, N and NH.

3. The compound or the pharmaceutically acceptable salt thereof according to claim 2, wherein, the structural moiety

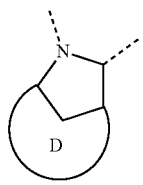

is selected from

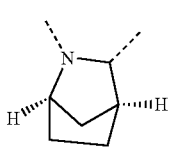 and 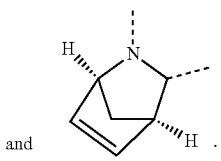.

4. The compound or the pharmaceutically acceptable salt thereof according to claim 2, wherein the structural moiety

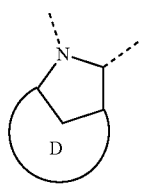

is selected from,

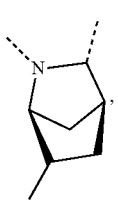, 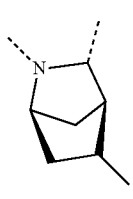, 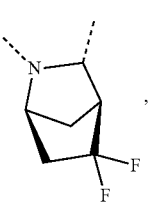,

, and 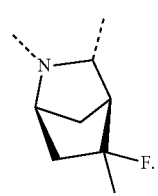.

5. The compound or the pharmaceutically acceptable salt thereof according to claim 2, wherein the compound is selected from:

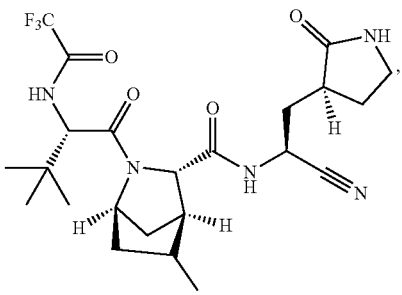,

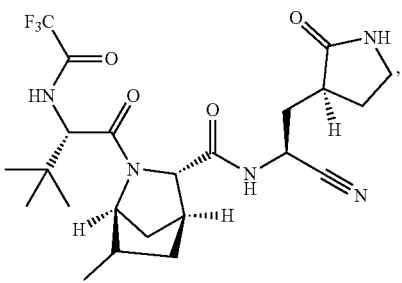,

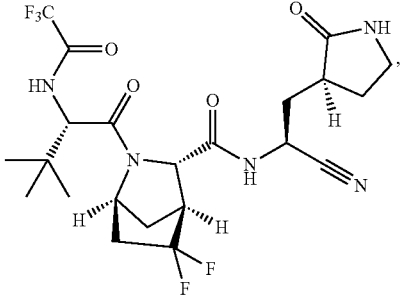,

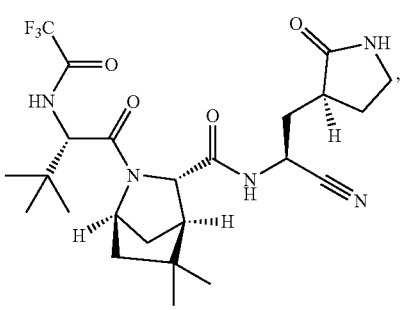,

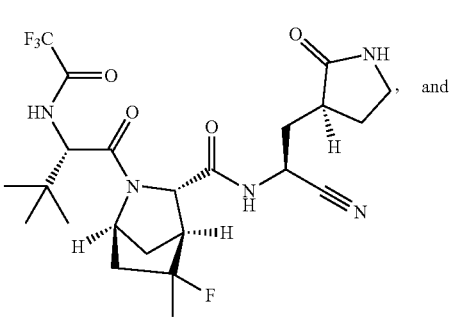 and

-continued

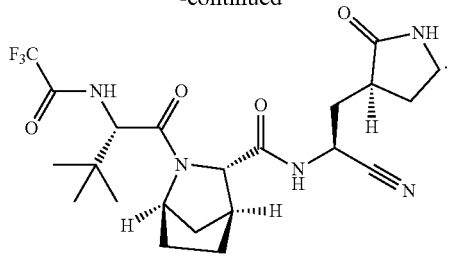

6. A pharmaceutical composition, comprising the compound or the pharmaceutically acceptable salt thereof according to claim 3 optionally a pharmaceutically acceptable excipient.

7. A method for the treatment of a disease related to 3CL protease in a subject in need thereof, comprising: administering the compound or the pharmaceutically acceptable salt thereof according to claim 2 to the subject, wherein the disease related to 3CL protease is coronavirus infection.

8. The method according to claim 7, wherein the coronavirus infection is infection with COVID-19.

* * * * *

```
                        SEQUENCE LISTING

Sequence total quantity: 1
SEQ ID NO: 1            moltype = AA  length = 13
FEATURE                 Location/Qualifiers
MOD_RES                 1
                        note = modified with Dabcyl
MOD_RES                 13
                        note = modified with Edans
source                  1..13
                        mol_type = protein
                        organism = synthetic construct
SEQUENCE: 1
KTSAVLQSGF RKM                                                               13
```